United States Patent
Cincotta

(10) Patent No.: US 10,137,132 B2
(45) Date of Patent: *Nov. 27, 2018

(54) PARENTERAL FORMULATIONS OF DOPAMINE AGONISTS

(71) Applicant: VeroScience, LLC, Tiverton, RI (US)

(72) Inventor: Anthony H. Cincotta, Tiverton, RI (US)

(73) Assignee: VeroScience, LLC, Tiverton, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/272,130

(22) Filed: May 7, 2014

(65) Prior Publication Data

US 2014/0249136 A1    Sep. 4, 2014

Related U.S. Application Data

(63) Continuation of application No. 12/144,620, filed on Jun. 23, 2008, now Pat. No. 8,741,918.

(60) Provisional application No. 61/020,930, filed on Jan. 14, 2008, provisional application No. 60/945,562, filed on Jun. 21, 2007.

(51) Int. Cl.
| | |
|---|---|
| *A01N 43/42* | (2006.01) |
| *A61K 31/44* | (2006.01) |
| *A01N 43/58* | (2006.01) |
| *A01N 43/60* | (2006.01) |
| *A61K 31/55* | (2006.01) |
| *A61K 9/00* | (2006.01) |
| *A61K 9/06* | (2006.01) |
| *A61K 9/20* | (2006.01) |
| *A61K 9/24* | (2006.01) |
| *A61K 9/70* | (2006.01) |
| *A61K 31/00* | (2006.01) |
| *A61K 31/135* | (2006.01) |
| *A61K 31/485* | (2006.01) |
| *A61K 31/4985* | (2006.01) |
| *A61K 45/06* | (2006.01) |
| *A61K 47/32* | (2006.01) |
| *A61K 47/38* | (2006.01) |

(52) U.S. Cl.
CPC ........... *A61K 31/55* (2013.01); *A61K 9/0019* (2013.01); *A61K 9/0056* (2013.01); *A61K 9/06* (2013.01); *A61K 9/209* (2013.01); *A61K 9/2018* (2013.01); *A61K 9/7007* (2013.01); *A61K 31/00* (2013.01); *A61K 31/135* (2013.01); *A61K 31/485* (2013.01); *A61K 31/4985* (2013.01); *A61K 45/06* (2013.01); *A61K 47/32* (2013.01); *A61K 47/38* (2013.01)

(58) Field of Classification Search
USPC ....................................................... 514/288
See application file for complete search history.

(56) References Cited

U.S. PATENT DOCUMENTS

| | | |
|---|---|---|
| 4,659,715 A | 4/1987 | Meier et al. |
| 4,783,469 A | 11/1988 | Meier et al. |
| 4,791,125 A | 12/1988 | Clark |
| 4,798,846 A | 1/1989 | Glen et al. |
| 5,006,526 A | 4/1991 | Meier et al. |
| 5,344,832 A | 9/1994 | Cincotta et al. |
| 5,468,755 A | 11/1995 | Cincotta |
| 5,496,803 A | 3/1996 | Meier et al. |
| 5,554,623 A | 9/1996 | Cincotta et al. |
| 5,565,454 A | 10/1996 | Cincotta |
| 5,585,347 A | 12/1996 | Meier et al. |
| 5,626,860 A | 5/1997 | Cincotta et al. |
| 5,635,512 A | 6/1997 | Cincotta et al. |
| 5,654,313 A | 8/1997 | Cincotta et al. |
| 5,668,155 A | 9/1997 | Cincotta et al. |
| 5,679,685 A | 10/1997 | Cincotta et al. |
| 5,688,794 A | 11/1997 | Meier et al. |
| 5,696,128 A | 12/1997 | Cincotta et al. |
| 5,700,795 A | 12/1997 | Cincotta et al. |
| 5,700,800 A | 12/1997 | Cincotta et al. |
| 5,712,265 A | 1/1998 | Cincotta et al. |
| 5,714,519 A | 2/1998 | Cincotta et al. |
| 5,716,932 A | 2/1998 | Meier et al. |
| 5,716,933 A | 2/1998 | Meier et al. |
| 5,716,957 A | 2/1998 | Cincotta et al. |
| 5,716,962 A | 2/1998 | Cincotta et al. |
| 5,719,160 A | 2/1998 | Cincotta et al. |
| 5,731,287 A | 3/1998 | Meier et al. |
| 5,731,312 A | 3/1998 | Cincotta et al. |
| 5,741,503 A | 4/1998 | Cincotta et al. |
| 5,744,477 A | 4/1998 | Cincotta et al. |

(Continued)

FOREIGN PATENT DOCUMENTS

| | | |
|---|---|---|
| CN | 1678313 | 10/2005 |
| JP | 1997301892 A | 11/1997 |

(Continued)

OTHER PUBLICATIONS

Dotto et al. (Clinical Pharmacokinetics of Cabergoline. Clinical Pharmacokinetics. 2003; 42(7):633-45).*

Hisahara et al. (Review Article Dopamine Receptors and Parkinson's Disease International Journal of Medicinal Chemistry vol. (2011), 16 pages).*

Hamilton (Involvement Response Toof The Adrenal Glands in the Hypotensive Bromocriptine in Spontaneously Hypertensive Rats. Br. J. Pharmac. (1981 ), 72, 419-425).*

(Continued)

*Primary Examiner* — Layla Soroush
(74) *Attorney, Agent, or Firm* — Fish & Richardson P.C.

(57) ABSTRACT

This invention relates to stable pharmaceutical compositions for parenteral administration comprising dopamine agonists and peripheral acting agents useful for treatment of metabolic disorders or key elements thereof. The parenteral dosage forms exhibit long stable shelf life and distinct pharmacokinetics.

10 Claims, 8 Drawing Sheets

(56) References Cited

U.S. PATENT DOCUMENTS

| | | | |
|---|---|---|---|
| 5,750,519 A | 5/1998 | Cincotta et al. | |
| 5,756,513 A | 5/1998 | Cincotta et al. | |
| 5,760,047 A | 6/1998 | Cincotta et al. | |
| 5,792,748 A | 8/1998 | Cincotta et al. | |
| 5,830,895 A | 11/1998 | Cincotta et al. | |
| 5,854,255 A | 12/1998 | Cincotta et al. | |
| 5,866,584 A | 2/1999 | Cincotta et al. | |
| 5,872,127 A | 2/1999 | Cincotta et al. | |
| 5,872,133 A | 2/1999 | Cincotta et al. | |
| 5,877,183 A | 3/1999 | Cincotta | |
| 5,902,811 A | 5/1999 | Cincotta | |
| 5,905,083 A | 5/1999 | Cincotta et al. | |
| 6,004,972 A | 12/1999 | Cincotta et al. | |
| 6,071,914 A | 6/2000 | Cincotta et al. | |
| 6,075,020 A | 6/2000 | Cincotta et al. | |
| 6,121,276 A | 9/2000 | El-Rashidy | |
| 6,855,707 B2 | 2/2005 | Cincotta | |
| 7,258,871 B2 | 8/2007 | Horowski et al. | |
| 7,888,310 B2 | 2/2011 | Cincotta | |
| 8,021,681 B2 | 9/2011 | Cincotta | |
| 8,137,992 B2 | 3/2012 | Cincotta | |
| 8,137,993 B2 | 3/2012 | Cincotta | |
| 8,137,994 B2 | 3/2012 | Cincotta | |
| 8,431,155 B1 | 4/2013 | Cincotta et al. | |
| 8,613,947 B2 | 12/2013 | Cincotta et al. | |
| 8,741,918 B2 | 6/2014 | Cincotta | |
| 8,821,915 B2 | 9/2014 | Cincotta | |
| 8,877,708 B2 | 11/2014 | Cincotta | |
| 9,192,576 B2 | 11/2015 | Cincotta et al. | |
| 9,205,084 B2 | 12/2015 | Cincotta | |
| 9,352,025 B2 | 5/2016 | Cincotta | |
| 9,415,005 B2 | 8/2016 | Cincotta | |
| 2001/0016582 A1 | 8/2001 | Cincotta et al. | |
| 2002/0187985 A1 | 12/2002 | Cincotta | |
| 2003/0212085 A1 | 11/2003 | McCall et al. | |
| 2004/0077679 A1 | 4/2004 | Cincotta | |
| 2004/0081678 A1 | 4/2004 | Cincotta | |
| 2004/0180088 A1 | 9/2004 | Dudhara et al. | |
| 2004/0214887 A1 | 10/2004 | Dasseux et al. | |
| 2004/0220190 A1 | 11/2004 | Cincotta | |
| 2005/0054652 A1 | 3/2005 | Cincotta | |
| 2005/0054734 A1 | 3/2005 | Cincotta | |
| 2005/0215558 A1 | 9/2005 | Cincotta | |
| 2005/0220855 A1 | 10/2005 | Horowski et al. | |
| 2005/0232989 A1 | 10/2005 | Piene et al. | |
| 2006/0057207 A1 | 3/2006 | Ziegler et al. | |
| 2006/0111348 A1* | 5/2006 | Kampen | A61K 31/519 514/227.8 |
| 2006/0239928 A1 | 10/2006 | Heit et al. | |
| 2007/0191371 A1 | 8/2007 | Bennett et al. | |
| 2007/0225379 A1 | 9/2007 | Carrara et al. | |
| 2007/0275060 A1 | 11/2007 | Befumo et al. | |
| 2007/0292479 A1 | 12/2007 | Podhaisky et al. | |
| 2008/0200453 A1 | 8/2008 | Cincotta | |
| 2008/0293735 A1 | 11/2008 | Cincotta | |
| 2009/0137598 A1 | 5/2009 | Cincotta | |
| 2009/0143390 A1 | 6/2009 | Cincotta | |
| 2010/0035886 A1 | 2/2010 | Cincotta et al. | |
| 2013/0197005 A1 | 8/2013 | Cincotta | |
| 2013/0274246 A1 | 10/2013 | Cincotta | |
| 2014/0051685 A1 | 2/2014 | Cincotta | |
| 2014/0249136 A1 | 9/2014 | Cincotta | |
| 2014/0342975 A1 | 11/2014 | Cincotta | |
| 2015/0011554 A1 | 1/2015 | Cincotta et al. | |
| 2015/0024995 A1 | 1/2015 | Cincotta | |
| 2015/0335641 A1 | 11/2015 | Cincotta | |
| 2016/0038424 A1 | 2/2016 | Cincotta et al. | |
| 2016/0324848 A1 | 11/2016 | Cincotta | |

FOREIGN PATENT DOCUMENTS

| | | | |
|---|---|---|---|
| JP | 2002539163 A | 11/2002 | |
| RU | 2467743 | 11/2012 | |
| WO | WO 1993/012701 | 7/1993 | |
| WO | WO 1994/015211 | 7/1994 | |
| WO | WO 1995/018614 | 7/1995 | |
| WO | WO 1996/000396 | 1/1996 | |
| WO | WO 1997/006786 | 2/1997 | |
| WO | WO 1997/041873 | 11/1997 | |
| WO | WO 1998/031368 | 7/1998 | |
| WO | WO 2000/032171 | 6/2000 | |
| WO | 200054774 A1 | 9/2000 | |
| WO | WO 2004/010946 | 2/2004 | |
| WO | WO 2005/016321 | 2/2005 | |
| WO | 2006103417 A1 | 10/2006 | |
| WO | WO 2006/128022 | 11/2006 | |
| WO | WO 2006128022 A2 * | 11/2006 | A61K 9/0056 |
| WO | 2007085498 A1 | 8/2007 | |
| WO | WO 2007/140191 | 12/2007 | |

OTHER PUBLICATIONS

"Alternative Routes of Drug Administration—Advantages and Disadvantages (Subject Review)," American Academy of Pediatrics-Committee on Drugs, Pediatrics, Jul. 1997, 100(1):143-152.

Benes et al., "Transmucosal, oral controlled—release, and transdermal drug administration in human subjects: a crossover study with melatonin," Journal of Pharmaceutical Sciences, Oct. 1997, 86(10):1115-1119.

Office Action issued in EP Application No. 10190054.6, dated Sep. 25, 2015, 9 pages.

Pijl et al., "Bromocriptine: a novel approach to the treatment of type 2 diabetes," Emer. Treat. Tech., Aug. 2000, 23(8):1154-1161.

Shojaei, "Buccal mucosa as a route for systemic drug delivery: a review," Journal of Pharmacy and Pharmaceutical Sciences, Jan. 1998, 1(1):15-30.

Zhang et al., "Inhibitory effects of bromocriptine on vascular smooth muscle cell proliferation," Atherosclerosis, Jan. 1997, 133(1):37-44.

Aelling et al., Comparative pharmacokinetic investigations with tritium-labeled ergot alkaloids after oral and intravenous administration in man Int J Clin Pharmacol, vol. 15, pp. 106-112, 1977.

Ansel et al., 1995, Pharmaceutical Dosage Forms and Drug Delivery Systems, Sixth edition, Williams & Wilkins, pp. 78-81.

Ciccarelli et al., Double blind randomized study using oral or injectable bromocriptine in patients with hyperprolactinaemia, Clinical Endocrinol, vol. 40, pp. 193-198, 1994.

Cicinelli et al., Nasal spray administration of bromocriptine: pharmacology and effect on serum prolactin level in puerperal women, Gynecol Endocrinol, vol. 10, pp. 391-396, 1996.

Cicinelli et al., Nasal spray bromocriptine: Effects on serum prolactin in puerperal women, Acta Obstet Gynecol Scand 75:730-733, 1996.

Cicinelli et al., Nasal spray vs oral administration of bromocriptine: Pharmacology and effect on serum prolactin in puerperal woman, J Endocrinol Invest, vol. 19, pp. 427-432, 1996.

Degim et al., Transdermal administration of bromocriptine, Biol Pharm Bull, vol. 26, pp. 501-505, 2003.

Durant, S. et al., Bromocriptine-Induced Hyperglycemia in Nonobese Diabetic Mice: Kinetics and Mechanisms of Action; The Review of Diabetic Studies, vol. 4, pp. 185-194, 2007.

Durif et al., Efficacy of sublingual apomorphine in Parkinson's disease, J Neurol Neurosurg Psych, vol. 53, p. 1105, 1990.

Fluckiger, E., Editorial Note, 1992, Experiential, 48:248.

Haase et al. Control of prolactin-secreting macroadenomas with parenteral, long-acting bromocriptine in 30 patients treated for up to 3 years, Clinical Endocrinology, vol. 38, Issue 2, pp. 165-176, 1993.

Humbert et al., Human pharmacokinetics of dihydroergotamine administered by nasal spray, Clin Pharmacol Ther, vol. 60, pp. 265-275, 1996.

International Preliminary Report on Patentability for counterpart International Application PCT/US2009/000268 dated Jul. 20, 2010.

International Search Report for counterpart International Application PCT/US2009/000268 dated Apr. 7, 2010.

Jaspers et al., Long term treatment of acromegalic patients with repeatable parenteral depot-bromocriptine, Clin Investig, vol. 71, pp. 547-551, 1993.

(56) References Cited

OTHER PUBLICATIONS

Katz et al., Successful treatment of a prolactin-producing pituitary macroadenoma with intravaginal bromocriptine mesylate: A novel approach to intolerance of oral therapy, Obstet Gynecol, vol. 73, pp. 517-520, 1989.
Kharkevich, DA, Pharmacology (textbook), Moscow, Gaotar-Media (2006), pp. 39 and 44.
Meier et al., Timed bromocriptine administration reduces body fat stores in obese subjects and hyperglycemia in type II diabetics, 1992, Experientia, 48:248-253.
Ondo et al., A novel sublingual apomorphine treatment for treatment for patients with fluctuating Parkinson's disease, Movement Disorders, vol. 14, pp. 664-668, 1999.
Reavill et al., Metabolite involvement in bromocriptine-induced circling behaviour in rodents, J. Pharm. Pharmacol., vol. 32, pp. 278-284, 1980.
Suresh et al., Intranasally delivered microdoses of bromocriptine (BCR) effectively reduces serum prolactin levels in hyperprolactinaemic patients, Current Sci, vol. 68, pp. 528-531, 1995.
Tsagarakis et al., Effectiveness of a long-lasting injectable form of bromocriptine in patients with prolactin and growth hormone secreting macroadenomas, Clinical Endocrinol, vol. 42, pp. 593-599, 1995.
Valente et al., Metabolite involvement in Bromocriptine-induced prolactin inhibition in rats, J Pharmacol Expt Therapeutics, vol. 282, pp. 1418-1424, 1997.
Vermesh et al., Vaginal Bromocriptine: Pharmacology and Effect on Serum Prolactin in Normal Women, Obstet Gynecol vol. 72, pp. 693-697, 1988.
Pietz et al., "Paper Subcutaneous apomorphine in late stage Parkinson's disease: a long term follow up," J Neurol Neurosurg Psychiatry1998;65:709-716).
English translation of relevant portions of Office Action dated Feb. 3, 2015 in corresponding Japanese Application No. 2014-13265.
English translation of relevant portions of Office Action dated Feb. 3, 2015 in corresponding Japanese Application No. 2014-13266.
Armentero et al., "Dopamine Receptor Agonists Media europrotection in malonate-Induced striatal lesion in the Rat," Experimental Neurology, Dec. 2002, 178(2):301-305.
Arteriosclerosis/atherosclerosis Definition-Diseases and Condition, by Mayo Clinic staff, May 2014, accessed on Oct. 8, 2014; available at http://www.mayoclinic.org/diseases-conditions/arteriosclerosis-atherosclerosis/basics/definition/con-20026972, 9 pages.
Breen et al., "Insulin increases reendothelialization and inhibits cell migration and neointimal growth after arterial injury," Arterioscler Thromb Vase Biol. 2009, 29:1060-1066.
Bruemmer et al., "Thiazolidinedione regulation of smooth muscle cell proliferation," The American Journal of Medicine, Dec. 8, 2003, 115(BA):87S-92S.
Dai et al., "LOX-1, a bridge between GLP-1 and mitochondrial ROS generation in human vascular smooth muscle cells," Biochemical and Biophysical Research Communications, 2013, 437:62-66.
Dios et al., "Troglitazone, but not rosiglitazone, inhibits na/h exchange activity and proliferation of macrovascular endothelial cells," Journal of Diabetes and its Complications, 2001, 15:120-127.
Dormandy et al., "Secondary prevention of macrovascular events in patients with type 2 diabetes in the PROactive Study (PROspective pioglitazone Clinical Trial in macrovascular events): a randomised controlled trial," Lancet, Oct. 8, 2005, 366:1279-89.
Dubey et al., "Pioglitazone attenuates hypertension and inhibits growth of renal arteriolar smooth muscle in rats," American Physiological Society, 1993, R726-R732.
Duckworth et al., "Glucose control and vascular complications in veterans with type 2 diabetes," The New England Journal of Medicine, Jan. 8, 2009, 360:129-139.
Ervinna et al., "Anagliptin, a dpp-4 inhibitor, suppresses proliferation of vascular smooth muscles and monocyte inflammatory reaction and attenuates atherosclerosis in male apo e-deficient mice," Endocrinology, Mar. 2013, 145(3):1260-1270.
Fukuda et al., "Troglitazone inhibits growth and improves insulin signaling by suppression of angiotensin ii action in vascular smooth muscle cells from spontaneously hypertensive rats," Atherosclerosis, 2002, 163:229-239.
Gaziano et al., "Effect of bromocriptine-qr (a quick-release formulation of bromocriptine mesylate) on major adverse cardiovascular events in type 2 diabetes subjects," J Am Heart Assoc, 2012, 1:doi:10.1161/JAHA.112.002279, 11 pages.
Gaziano et al., "Randomized clinical trial of quick-release bromocriptine among patients with type 2 diabetes on overall safety and cardiovascular outcomes," Diabetes Care, Jul. 2010, 33:1503-1508 (12 total pages).
Gerstein et al., "Effects of intensive glucose lowering in type 2 diabetes," The New England Journal of Medicine, Jun. 12, 2008, 358:2545-59.
Gerstein, "Basal insulin and cardiovascular and other outcomes in dysglycemia," The New England Journal of Medicine, Jul. 26, 2012, 367:319-328.
Goto et al., "Exendin-4, a glucagon-like peptide-1 receptor agonist, reduces intimal thickening after vascular injury," Biochemical and Biophysical Research Communications, 2011, 405:79-84.
Gouni-Berthold et al., "Troglitazone and rosiglitazone inhibit the low density lipoprotein-induced vascular smooth muscle cell growth," Exp Clin Endocrinol Diabetes, 2001, 109:203-209.
Ha et al., "High glucose induces connective tissue growth factor expression and extracellular matrix accumulation in rat aorta vascular smooth muscle cells via extracellular signal-regulated kinase ½," Korean J Physiol Pharmacol, Aug. 2013, 17:307-314.
Hara et al., "Central dopaminergic function in stroke prone spontaneously hypertensive rats effects of chronic treatment with lisuride on the impaired swimming ability," Database Accession No. PREV198376013141 and Folia Pharmacologica Japonica, 1982, 80(5):395-394 (Abstract only—2 pages).
Hasko et al., "Modulation of lipopolysaccharide-induced tumor necrosis factor-$\alpha$ and nitric oxide production by dopamine receptor agonists and antagonists in mice," Immunology Letters, 1996, 49(3):143-147.
Home et al., "Rosiglitazone evaluated for cardiovascular outcomes in oral agent combination therapy for type 2 diabetes (record): a multicentre, randomised, open-label trial," Lancet, Jun. 20, 2009, 373:2125-35.
Hsueh et al., "Insulin signaling in the arterial wall," Am J Cardiol, 1999, 84:21J-24J.
Kuo et al., "Hypothalamic neuropeptide Y (NPY) and the attenuation of hyperphagia in streptozotocin diabetic rats treated with dopamine D1/D2 agonists," British Journal of Pharmacology, 2006, 148:640-647.
Lan et al., "Vascular fibrosis in atherosclerosis," Cardiovascular Pathology, 2013, 22:4101-407.
Lightell et al., "Loss of canonical insulin signaling accelerates vascular smooth muscle cell proliferation and migration through changes in p27kip1 regulation," Endocrinology, Feb. 2011, 152(2):651-658.
Lusis, "Atherosclerosis," Nature, 407(6801): 233-241, Sep. 14, 2000.
NCBI Reference Sequence XP-002587257, Hypothetical Protein BRAFLDRAFT-61678 (Branchiostoma floridae), Accession No. XP_002587257, GI No. 260784404, dated Oct. 8, 2009, (retrieved from the Internet: Feb. 23, 2015), 2 pages.
O'Neill et al., "Dopamine D2 receptor agonists protect against ischaemia induced hippocampal neurodegeneration in global cerebral ischaemia," European Journal of Pharmacology, Jul. 3, 1998, 352(1):37-46.
Park et al., "The inhibition of insulin-stimulated proliferation of vascular smooth muscle cells by rosiglitazone is mediated by the akt-mtor-p70s6k pathway," Yonsei Med J, 2008, 49(4):592-600.
Patel et al., "Intensive blood glucose control and vascular outcomes in patients with type 2 diabetes," The New England Journal of Medicine, Jun. 6, 2008, 358:2560-72.
Pijl and Meinders, "Modulation of monoaminergic neural circuits: potential for the treatment of type 2 diabetes mellitus," Treat Endocrine, 2002, 1(2):71-78.

(56) References Cited

OTHER PUBLICATIONS

Ratner et al., "Cardiovascular safety of exenatide BID: an integrated analysis from controlled clinical trials in participants with type 2 diabetes," Cardiovascular Diabetology, 2011, 10:22, 10 pages.
Schaper et al., "Peripheral vascular disease and Type 2 diabetes mellitus," Diabetes Metab Res Rev, 2000, 16(Suppl 1) S11-S15.
Schobel et al., "Effects of bromocriptine on cardiovascular regulation in healthy humans," Hypertension, 25(5):1075-1082, May 1995.
Scirica et al., "Saxagliptin and cardiovascular outcomes in patients with type 2 diabetes mellitus," The New England Journal of Medicine, Oct. 3, 2013, 369(14):1317-1326.
Stout, "Insulin as a mitogenic factor: role in the pathogenesis of cardiovascular disease," The American Journal of Medicine, Feb. 21, 1991, 90 (suppl 2A-62S-65S).
Takasawa, "Inhibition of dipeptidyl peptidase 4 regulates microvascular endothelial growth induced by inflammatory cytokines," Biochemical and Biophysical Research Communications, 2010, 401:7-12.
Turner, "Intensive blood-glucose control with sulphonylureas or insulin compared with conventional treatment and risk of complications in patients with type 2 diabetes (UKPDS 33)," UK Prospective Diabetes Study D (UKPDS) Group, The Lancet, Sep. 12, 1998, 352:837-853.
White et al., "Alogliptin after acute coronary syndrome in patients with type 2 diabetes," The New England Journal of Medicine, Oct. 3, 2013, 369(14):1327-1335.
Zou et al., "Protein-protein coupling/uncoupling enables dopamine d2 receptor regulation of AMPA receptor-mediated excitotoxicity," The Journal of Neuroscience, Apr. 27, 2005, 25(17):4385-4395.
First Office Action issued in CN Application No. 200880025452.8, dated Apr. 19, 2012, 11 pages (with English translation).
Second Office Action issued in CN Application No. 200880025452.8, dated Mar. 28, 2013, 15 pages (with English translation).
Third Office Action issued in CN Application No. 200880025452.8, dated Feb. 10, 2014, 8 pages (with English translation).
Fourth Office Action issued in CN Application No. 200880025452.8, dated Jan. 22, 2015, 14 pages (with English translation).
Office Action in CN Application No. 201180035790.1, dated Nov. 20, 2013, 20 pages.
Extended European Search Report issued in EP Application No. 08768002.1, dated Jul. 8, 2010, 7 pages.
Communication Pursuant to Article 94(3) EPC issued in EP Application No. 08768002.1, dated.Apr. 20, 2011, 4 pages.
Communication Pursuant to Article 94(3) EPC issued in EP Application No. 08768002.1, dated Jan. 15, 2014, 7 pages.
Extended European Search Report issued in EP Application No. 08742225.9, dated Oct. 15, 2010, 12 pages.
Communication Pursuant to Article 94(3) EPC issued in EP Application No. 08742225.9, dated Dec. 23, 2014, 4 pages.
First Examination Report issued in in Application No. 7696/DELNP/2009, dated Jan. 7, 2015, 2 pages.
Opposition filed by Indian Pharmaceutical Alliance against corresponding Indian Patent Application No. 7696/DELNP/2009 (owned by VeroScience, LLC), Jan. 3, 2011, 38 pages.
Office Action issued in JP Application No. 2010-510366, dated Oct. 4, 2013, 5 pages (with English tmnslation).
Office Action issued in JP Application No. 2014-018636, dated Mar. 10, 2015, 8 pages (with English tmnslation).
Office Action issued in MX Application No. MX/a/2009/012919, dated Sep. 19, 2011, 3 pages (with English translation).
Office Action issued in MX Application No. MX/a/2009/012919, dated Jun. 5, 2012, 6 pages (with English tmnslation).
Office Action issued in MX Application No. MX/a/2009/012919, dated Feb. 11, 2013, 7 pages (with English translation).
Office Action issued in MX Application No. MX/a/2009/012919, dated Sep. 3, 2013, 7 pages (with English translation).
Non-final Office Action issued in U.S. Appl. No. 12/077,552, dated Jul. 7, 2011, 10 pages.
Final Office Action issued in U.S. Appl. No. 12/077,552, dated Apr. 10, 2012, 12 pages.
Final Office Action issued in U.S. Appl. No. 12/077,552, dated Jul. 16, 2013, 13 pages.
Non-final Office Action issued in U.S. Appl. No. 12/077,552, dated Feb. 10, 2014, 10 pages.
Final Office Action issued in U.S. Appl. No. 12/077,552, dated Oct. 22, 2014, 22 pages.
Non-final Office Action issued in U.S. Appl. No. 12/077,552, dated Sep. 15, 2015, 31 pages.
International Preliminary Report on Patentability issued in International Application No. PCT/US2008/006899, dated Dec. 1, 2009, 7 pages.
International Preliminary Report on Patentability issued in International Application No. PCT/US2008/003849, dated Oct. 6, 2009, 7 pages.
International Search Report and Written Opinion issued in International Application No. PCT/US2008/006899, dated Aug. 29, 2008, 7 pages.
International Search Report and Written Opinion issued in International Application No. PCT/US2008/003849, dated Jun. 20, 2008, 7 pages.
Burns and Caine, "Disposition of Dopaminergic Ergot Compounds Following Oral Administration," Lisureide and Other Dopamine Agonists, 1983, 87-94.
Cannon, "Dopamine agonists: Structure-activity relationships," In: Progress in Drug Research, 1985, 29: 303-413.
Colao et al., "Dopamine receptor agonists for treating prolactinomas," 2002, Expert Opin. Investig. Drugs, 11: 787-800.
Goetz et al., "DA Agonists—Ergot derivatives: Bromocriptine," Movement Disorders, 2002, 17: S53-S67.
Loew et al., "Effects on the Central Nervous System," In: Ergot Alkaloids and Related Compounds, 1978, 422-531.
Mantegani et al., "Ergoline derivatives: receptor affinity and selectivity," II Farmaco, 1999, 54: 288-296.
Markstein et al., "Structure Activity Relationship and Theraputic Uses of Dopaminergic Ergots," Neurochem. Int., 1992, 20: 211S-214S.
Schojaei et al., "Buccal Mucosa as a route for systemic drug delivery: A Review," J. Pharm. Pharmaceutical Science, 1998, 1(1):15-30.
Office Action in Australian Application No. 2009205641, dated Jul. 3, 2013, 4 pages.
Office Action in Australian Application No. 2009205641, dated Sep. 25, 2014, 4 pages.
Notice of Acceptance in Australian Application No. 2009205641, dated Nov. 28, 2014, 3 pages.
Office Action in Australian Application No. 2015201255, dated Nov. 23, 2015, 4 pages.
Notice of Acceptance in Australian Application No. 2015201255, dated May 4, 2016, 2 pages.
Office Action in Canadian Application No. 2749611, dated Mar. 17, 2015, 3 pages.
Office Action in Canadian Application No. 2749611, dated Nov. 27, 2015, 3 pages.
Office Action in Chinese Application No. 200980108993.1, dated Aug. 18, 2011, 7 pages (with English translation).
Office Action in Chinese Application No. 200980108993.1, dated Aug. 23, 2012, 8 pages (with English translation).
Office Action in Chinese Application No. 200980108993.1, dated Apr. 24, 2013, 8 pages (with English translation).
Office Action in Chinese Application No. 200980108993.1, dated Nov. 26, 2013, 4 pages (with English translation).
Office Action in Chinese Application No. 200980108993.1, dated Sep. 2, 2014, 9 pages (with English translation).
Office Action in Chinese Application No. 200980108993.1, dated Feb. 25, 2016, 6 pages (with English translation).
European Search Report issued in Application No. 10190054.6, dated Mar. 22, 2011, 10 pages.
Office Action in European Application No. 10190054.6, dated Sep. 25, 2015, 9 pages.
Office Action in Israeli Application No. 207001, dated Jan. 21, 2013, 4 pages (with English translation).
Office Action in Israeli Application No. 207001, dated Jan. 28, 2014, 5 pages (with English translation).

(56) References Cited

OTHER PUBLICATIONS

Office Action in Israeli Application No. 207001, dated Feb. 22, 2016, 5 pages (with English translation).
Office Action in Indian Application No. 2989/KOLNP/2010, dated Oct. 9, 2015, 2 pages.
Office Action in Japanese Application No. 2010-543138, dated Jul. 30, 2013, 7 pages (with English translation).
Office Action in Japanese Application No. 2010-543138, dated Apr. 15, 2014, 2 pages (with English translation).
Office Action in Japanese Application No. 2014-13265, dated Jan. 26, 2016, 4 pages (with English translation).
Decision to Grant in Japanese Application No. 2014-13265, dated Apr. 26, 2016, 6 pages (with English translation).
Office Action in Japanese Application No. 2014-13266, dated Feb. 3, 2015, 4 pages (with English translation).
Office Action in Japanese Application No. 2014-13266, dated Jan. 26, 2016, 4 pages (with English translation).
Decision to Grant in Japanese Application No. 2014-13266, dated Apr. 26, 2016, 6 pages (with English translation).
Office Action in Mexican Application No. MX/a/2010/007741, dated Feb. 13, 2012, 4 pages (with English translation).
Office Action in Mexican Application No. MX/a/2010/007741, dated Oct. 3, 2012, 4 pages (with English translation).
Office Action in Mexican Application No. MX/a/2010/007741, dated Jun. 14, 2013, 6 pages (with English translation).
Office Action in Mexican Application No. MX/a/2010/007741, dated Mar. 4, 2014, 6 pages (with English translation).
Office Action in Mexican Application No. MX/a/2010/007741, dated Dec. 1, 2014, 6 pages (with English translation).
Office Action in Mexican Application No. MX/a/2010/007741, dated Dec. 14, 2015, 29 pages (with English translation).
Office Action in Russian Application No. 2010134158, dated Feb. 8, 2013, 9 pages (with English translation).
Office Action in Russian Application No. 2010134158, dated Jun. 27, 2013, 12 pages (with English translation).
Restriction Requirement in U.S. Appl. No. 12/144,620, dated Mar. 1, 2011, 10 pages.
Office Action in U.S. Appl. No. 12/144,620, dated Jun. 9, 2011, 14 pages.
Office Action in U.S. Appl. No. 12/144,620, dated Jan. 27, 2012, 22 pages.
Notice of Allowance in U.S. Appl. No. 12/144,620, dated Mar. 31, 2014, 8 pages.
Restriction Requirement in U.S. Appl. No. 12/402,694, dated Mar. 3, 2011, 11 pages.
Office Action in U.S. Appl. No. 12/402,694, dated Sep. 1, 2011, 31 pages.
Office Action in U.S. Appl. No. 12/402,694, dated May 17, 2012, 36 pages.
Office Action in U.S. Appl. No. 12/402,694, dated Dec. 5, 2014, 37 pages.
Office Action in U.S. Appl. No. 12/402,694, dated Dec. 18, 2015, 27 pages.
Restriction Requirement in U.S. Appl. No. 13/799,138, dated May 16, 2013, 5 pages.
Office Action in U.S. Appl. No. 13/799,138, dated Oct. 18, 2013, 39 pages.
Office Action in U.S. Appl. No. 13/799,138, dated Apr. 7, 2014, 37 pages.
Office Action in U.S. Appl. No. 13/799,138, dated May 13, 2015, 52 pages.
Office Action in U.S. Appl. No. 13/799,138, dated Sep. 29, 2015, 52 pages.
Notice of Allowance in U.S. Appl. No. 13/799,138, dated Apr. 14, 2016, 10 pages.
Restriction Requirement in U.S. Appl. No. 14/272,130, dated Oct. 2, 2015, 6 pages.
Office Action in U.S. Appl. No. 14/272,130, dated Apr. 13, 2016, 38 pages.

* cited by examiner

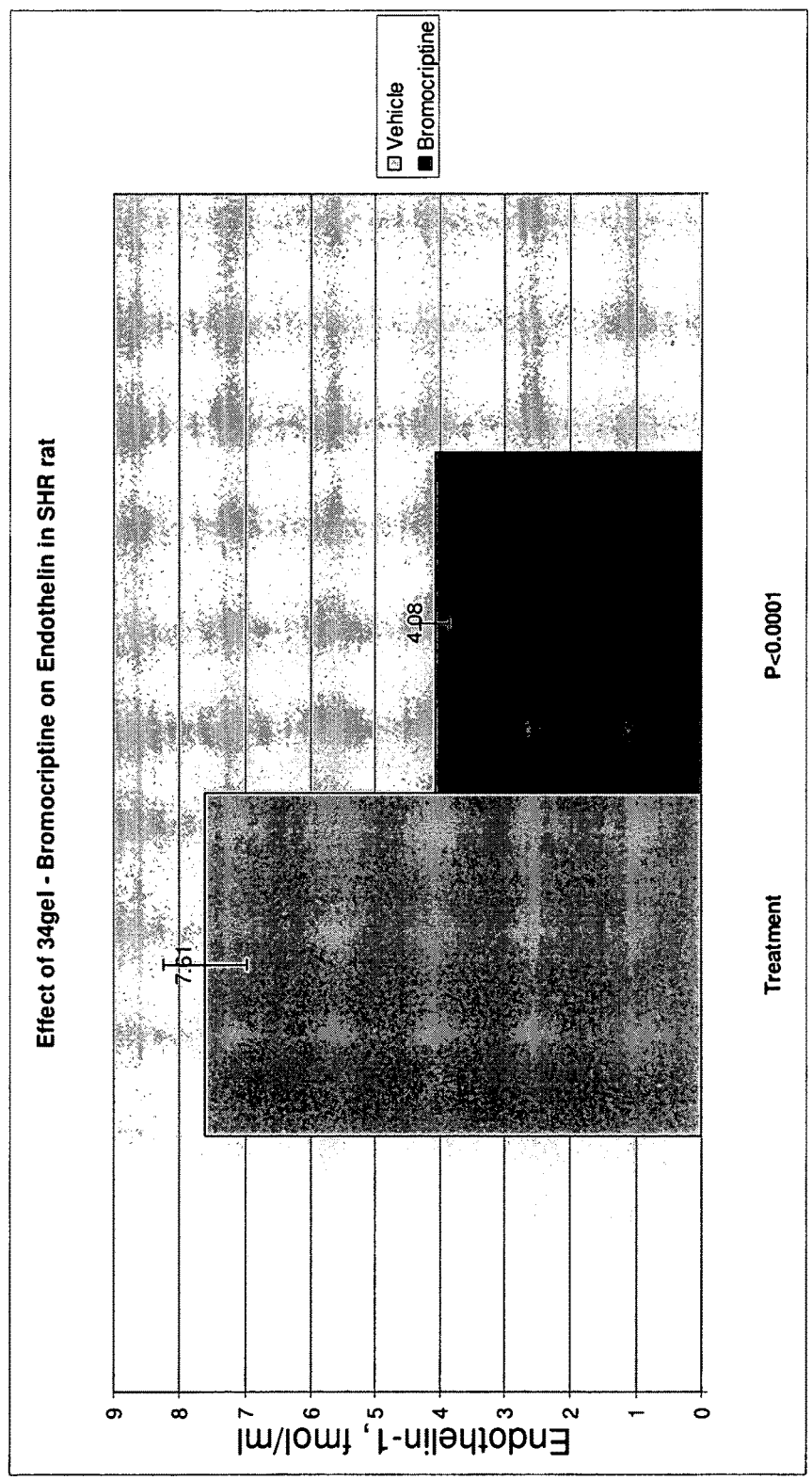

PARENTERAL FORMULATIONS OF DOPAMINE AGONISTS

CROSS REFERENCE TO RELATED APPLICATIONS

This application is a continuation of U.S. patent application Ser. No. 12/144,620 filed on Jun. 23, 2008 which claims priority under 35 U.S.C. § 119(e) of provisional applications No. 60/945,562, filed Jun. 21, 2007 and 61/020,930 filed Jan. 14, 2008. Each of the foregoing applications is hereby incorporated herein by reference in its entirety.

FIELD OF THE INVENTION

This invention relates to pharmaceutical parenteral dosage formulations comprising dopamine agonists, alone or in combination with peripheral acting agents useful for treatment of metabolic disorders, and to processes for preparing such formulations and methods of treatment using such formulations.

BACKGROUND OF THE INVENTION

Dopamine agonists are useful in the treatment of various diseases such as migraine headache, Parkinson's disease, acromegaly, hyperprolactinemia, prolactinoma, galactorrhea, amenorrhea, and metabolic disorders. It has been typically preferred to administer dopamine agonists in tablet and capsule forms. Administration of dopamine agonists via the gut, however, is subject to several problems.

Dopamine agonists absorbed via the gastric or intestinal mucosa of the gastrointestinal (GI) tract, for example, typically undergo extensive "first-pass" metabolism and destruction by the viscera, primarily the liver, resulting in a very small percentage of an administered dose reaching the systemic circulation. First-pass metabolism results from inactivation of orally administered drug in the gut and liver, before the drug reaches the systemic circulation for delivery to other organs and tissues of the body. Consequently, oral doses of compounds for medicinal use that are subject to first pass metabolism for medicinal use must be high enough to account for the substantial initial loss of drug, so that sufficient amounts of the drugs reach the systemic circulation to produce a therapeutic benefit.

Absorption of dopamine agonists via the gastric or intestinal mucosa may also be problematic because dopamine agonists and their metabolites may cause undesirable side effects (e.g., nausea, vomiting, abdominal pain, constipation, and diarrhea). The need to use increased dosages to account for first-pass metabolism in order to achieve therapeutic effectiveness increases the probability of undesirable GI side effects.

First-pass metabolism and visceral exposure can be substantially avoided by parenteral drug dosage forms that provide for administration and the substantial absorption of dopamine agonists through a route or routes other than the gastric and/or intestinal mucosa. Parenteral drug dosage forms also beneficially provide a mechanism for reducing the overall therapeutic dopamine agonist dosage amount, inasmuch as there is no necessity to overcome first-pass metabolism.

Production of stable parenteral formulations comprising ergot derivative dopamine agonists is particularly challenging, however, because ergot derivatives are extremely labile to light and water. Thus, ergot derivatives must be formulated in a manner that avoids light and prevents hydration.

Further, formulations useful for treating metabolic disorders or the key elements thereof require production of a particular pharmacokinetic profile that takes into account daily fluctuations in the levels of various hormones. That is, many of the hormones involved in metabolic disorders exhibit a daily circadian rhythm of fluctuating serum levels. Such hormones include adrenal steroids, e.g., the glucocorticosteroids, notably cortisol, and prolactin, a hormone secreted by the pituitary gland. These daily rhythms provide useful indices for understanding and treating metabolic diseases. For example, peak concentration of prolactin occurs at different times of day in lean and fat animals.

The normal daily prolactin level profile of a healthy human is highly regular and reproducible, characterized by a low and relatively constant day level followed by a sharp night-time peak, returning to a low level by daytime. See U.S. Pat. No. 5,679,685 the contents of which are incorporated herein by reference. Altering the prolactin profile of a subject having a metabolic disorder or key element thereof to resemble that of a healthy subject of the same species and sex can provide therapeutic benefit to the subject. Dopamine agonists are useful agents for treatment of metabolic disease and/or key elements of metabolic disease and can be used to reset daily prolactin profiles in subjects with metabolic disease and/or exhibiting key elements thereof to that of healthy humans.

Administration of dopamine agonists can act centrally to readjust towards "normal" those aberrant neuroendocrine events controlling peripheral metabolism in subjects with metabolic disease. Dopamine agonist therapy thus can impact etiological factors in the development and maintenance of metabolic disorders including, but not limited to, those associated with obesity, type 2 diabetes, pre-diabetes, cardiometabolic risk and/or metabolic syndrome. Because of its unique central mechanism of action, this therapy may be effectively combined with various peripheral acting agents that target specific peripheral biochemistry operative in manifesting particular elements of metabolic disease that may not be fully alleviated by dopamine agonist therapy, such as HMGCoA reductase inhibitors to reduce elevated plasma cholesterol, anti-hypertensives to reduce blood pressure by mechanisms different from those of dopamine agonist therapy, and anti-diabetes agents that augment the resetting effect of dopamine agonists on glucose metabolism such as postprandial insulin secretagouges or insulin itself, anti-inflammatory agents, and anti-coagulative agents.

There is a need in the art for improved formulations for administering dopamine agonists, particularly for the treatment of metabolic diseases. Accordingly, the improved formulations suitable for administering parenteral dopamine agonists disclosed herein avoid problems and improve methods for effectively treating metabolic disease associated with prior art formulations. The formulations disclosed herein avoid problems such as, e.g., first-pass metabolism and production of undesirable side effects and influences on efficacy due to ingestion of the drug.

SUMMARY OF THE INVENTION

The present invention is directed to formulations for administering dopamine agonists, including formulations comprising one or more dopamine agonist and one or more peripheral acting agent, and methods of using such formulations to treat metabolic disorders.

In one embodiment, the invention provides a dosage form comprising an active agent comprising one or more dopamine agonists and a pharmaceutically acceptable excipient, said dosage form being suitable for parenteral administration and exhibiting a pharmacokinetic profile with a plasma $T_{max}$ from about 1 to about 90 minutes after administration, a plasma drug concentration of at least 50% $C_{max}$ for a duration of about 90 to about 360 minutes, and a decrease in plasma level that may approximate first order elimination kinetics.

In another embodiment, the invention provides a method for treating a metabolic disorder or at least one key element thereof, comprising administering to a subject in need thereof a therapeutically effective amount of a dosage form comprising an active agent comprising one or more dopamine agonists and a pharmaceutically acceptable excipient, said dosage form being suitable for parenteral administration and exhibiting a pharmacokinetic profile with a plasma $T_{max}$ from about 1 to about 90 minutes after administration, a plasma drug concentration of at least 50% $C_{max}$ for a duration of about 90 to about 360 minutes, and a decrease in plasma level that may approximate first order elimination kinetics.

In another embodiment, the invention provides a method of reducing elevated plasma norepinephrine levels comprising administering to a subject in need thereof a therapeutically effective amount of a dosage form comprising an active agent comprising one or more dopamine agonists and a pharmaceutically acceptable excipient, said dosage form being suitable for parenteral administration and exhibiting a pharmacokinetic profile with a plasma $T_{max}$ from about 1 to about 90 minutes after administration, a plasma drug concentration of at least 50% $C_{max}$ for a duration of about 90 to about 360 minutes, and a decrease in plasma level that may approximate first order elimination kinetics.

In another embodiment, the invention provides a method of reducing diurnal plasma prolactin levels while maintaining an increase in nocturnal plasma prolactin levels relative to diurnal plasma prolactin levels comprising administering to a subject in need thereof a therapeutically effective amount of a dosage form comprising an active agent comprising one or more dopamine agonists and a pharmaceutically acceptable excipient, said dosage form being suitable for parenteral administration and exhibiting a pharmacokinetic profile with a plasma $T_{max}$ from about 1 to about 90 minutes after administration, a plasma drug concentration of at least 50% $C_{max}$ for a duration of about 90 to about 360 minutes, and a decrease in plasma level that approximates first order elimination kinetics.

In another embodiment, the invention provides a method for reducing elevated cardiovascular-related inflammatory factors or cardiovascular disease or key elements of cardiovascular disease, comprising administering to a subject in need thereof a therapeutically effective amount of a dosage form comprising an active agent comprising one or more dopamine agonists and a pharmaceutically acceptable excipient, said dosage form being suitable for parenteral administration and exhibiting a pharmacokinetic profile with a plasma $T_{max}$ from about 1 to about 90 minutes after administration, a plasma drug concentration of at least 50% $C_{max}$ for a duration of about 90 to about 360 minutes, and a decrease in plasma level that may approximate first order elimination kinetics.

In one embodiment, the invention provides a dosage form comprising an active agent comprising one or more dopamine agonists and a pharmaceutically acceptable excipient, said dosage form being suitable for parenteral administration and exhibiting a pharmacokinetic profile with a plasma $T_{max}$ from about 5 to about 90 minutes after administration, a post $C_{max}$ level of about one-half $C_{max}$ within about 30 to about 150 minutes of $T_{max}$, a post $C_{max}$ level of about one-half $C_{max}$ for a duration of about 90 to about 360 minutes, and a decrease in plasma level that may approximate first order elimination kinetics.

In another embodiment, the invention provides a method for treating a metabolic disorder or key element thereof by administration of a parenteral dosage form containing one or more dopamine agonists wherein elevated plasma norepinephrine and prolactin levels are reduced and a nocturnal plasma prolactin level is increased relative to the newly established average diurnal circulating level of prolactin.

BRIEF DESCRIPTION OF THE DRAWINGS

FIG. 8 is a graph showing the effect of 7 day parenteral treatment with the 34 Gel formulation (10 mg/kg) on endothelin-1 levels in the SHR rat model.

DETAILED DESCRIPTION OF THE INVENTION

Figure 1:
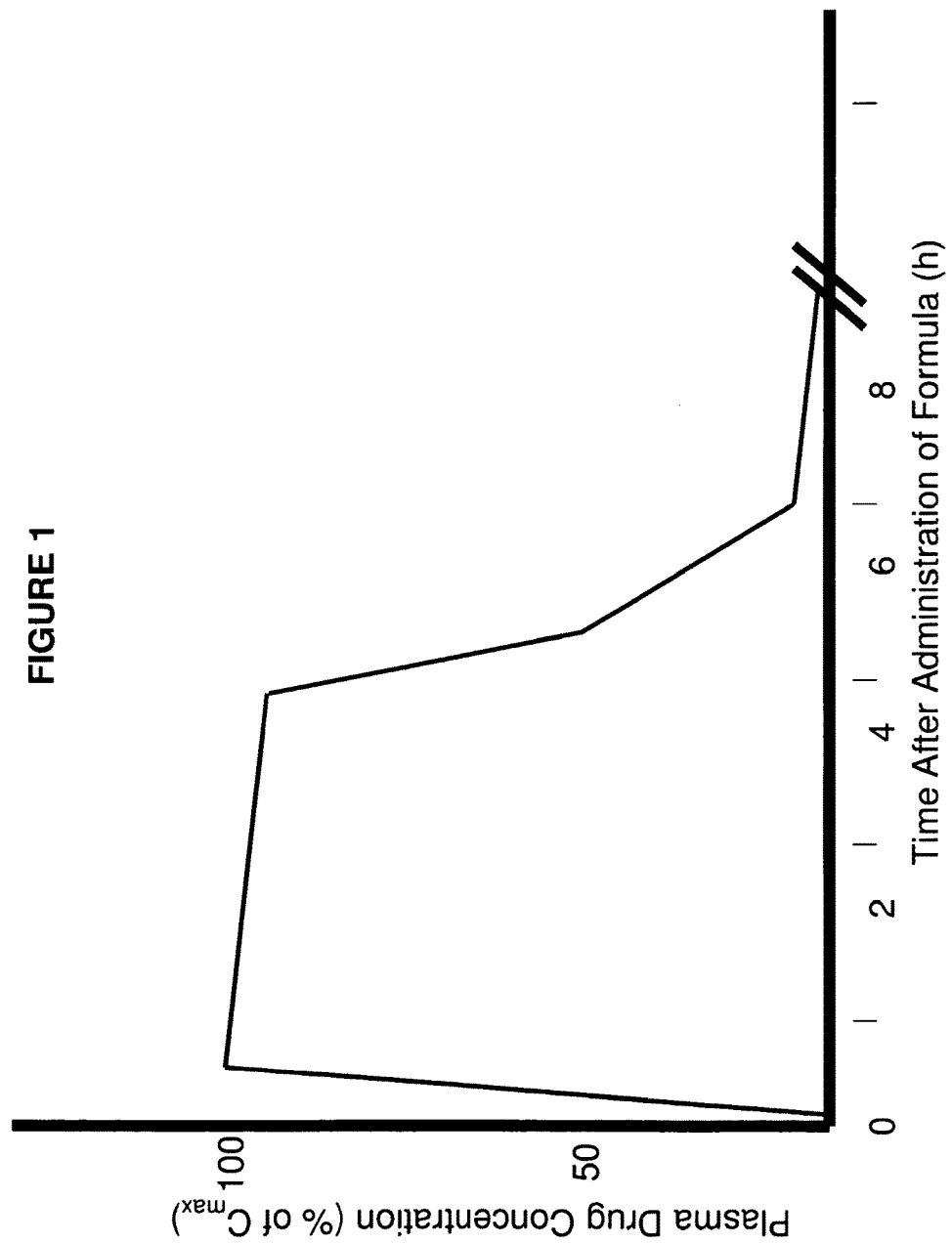
FIG. 1 is a graph showing a pharmacokinetic profile of a parenteral dosage formulation according to the present invention for administering a dopamine agonist.

Disclosed herein are parenteral dosage forms suitable for administering, e.g., one or more dopamine agonist alone or in combination with one or more anti-hypertensive, anti-hypercholesterolemic, anti-hypertriglyceridemic, anti-inflammatory, anti-coagulative, or anti-hyperglycemic agent. The dosage forms exhibit physiological attributes, e.g., a pharmacokinetic profile that induces certain neuroendocrine effects and enables treatment of metabolic disorders and/or key elements thereof. The dosage forms comprise an active agent or active agents and one or more excipients.

The dosage forms are particularly suited for treatment of metabolic disorders and/or key elements of these disorders including but not limited to, type 2 diabetes, prediabetes (impaired fasting glucose or impaired glucose tolerance), metabolic syndrome or indices (key elements) thereof (increased waist circumference, increased fasting plasma glucose, increased fasting plasma triglycerides, decreased fasting high density lipoprotein level, increased blood pressure), insulin resistance, hyperinsulinemia, cardiovascular disease (or key elements thereof such as arteriosclerosis, coronary artery disease, peripheral vascular disease, or cerebrovascular disease), congestive heart failure, obesity, elevated plasma norepinephrine, elevated cardiovascular-related inflammatory factors, hyperlipoproteinemia, atherosclerosis, hyperphagia, hyperglycemia, hyperlipidemia, and hypertension or high blood pressure, increased plasma postprandial triglyceride or free fatty acid levels, increased cellular oxidative stress or plasma indicators thereof, increased circulating hypercoagulative state, renal disease including renal insufficiency.

The dosage forms comprising dopamine agonist(s) and a peripheral targeting agent(s) could be applied to specific patient populations as needed, for example, dopamine agonist+ HMGCoA reductase formulations for hyprecholesterolemic-type 2 diabetics or dopamine agonist+ anti-hypertensive medication for very hypertensive-type 2 diabetics, and other combinations. Moreover, this combination dopamine agonist+ peripheral targeting agent therapy could be of further unique value and utility if it were within a singular formulation that would allow for the appropriate dosing of each of the components. In effect, such a formulation(s) could be the "poly pill" the medical and pharmaceutical communities have been seeking to treat the multiple abnormalities associated with common metabolic diseases of type 2 diabetes, obesity, metabolic syndrome and/or cardiometabolic risk with a single-dosage, once-daily medicinal. Parenteral formulations would allow for optimal, low dosing of the dopamine agonist(s) as described herein as well as, in certain embodiments, for HMGCoA reductase inhibitors that also undergo first-pass hepatic metabolism.

The combination parenteral formulations according to this invention also provide the ability to tailor metabolic disease therapy on a subject by subject basis that includes a central acting "resetting" component that addresses global metabolic disease (hypertension, dyslipidemia, and hyperglycemia) with any of several peripheral acting agents that address specific targets of metabolic disease (either hypertension, dyslipidemia, or hyperglycemia) as the need may be on an individual patient basis. At the same time, the combination parenteral formulations according to this invention also allow for the administration of smaller doses of dopamine agonists and/or peripheral acting agents, and thus to mitigate or avoid altogether side-effects that may be associated with administration of the dopamine agonists and the peripheral acting agents. For example, by having the peripheral anti-hypertensive agent reach peak concentrations a few hours after the dopamine agonist, the potential for orthostatic hypotension as well as syncope, or loss of consciousness, is reduced or avoided. In another example, for combinations with HMGCoA reductase inhibitors, lower dosages of both the dopamine agonist and HMGCoA reductase inhibitor can be used since both are subject to first pass hepatic metabolism (and for ergot-related dopamine agonists both actually utilize the same cytochrome P450-3A pathway for metabolism). If the HMGCoA reductase inhibitor is released after the dopamine agonist then there is less chance of competitive interaction at the liver for metabolism, a beneficial circumstance as this allows for better prediction of circulating dose for each compound. This will reduce the potential side effects on muscle pain that can be observed with each of these agents. In a further example, for combinations of dopamine agonists with insulin secretagogues (e.g., continuous or, preferably, post-prandial insulin secretagogues), such formulations allow for once-daily dosing—the formulations according to this invention facilitate the immediate release of insulin, followed by another release of insulin four hours later, thus facilitating insulin release at the proper times after breakfast and lunch, while at the same time minimizing the risk of hypoglycemia, a serious consideration with all anti-diabetes medications.

The parenteral dosage forms disclosed herein have desirable properties relative to oral dosage forms, including improved effectiveness of a delivered drug in treating metabolic disease and/or key elements of metabolic disease, administration of smaller amounts of dopamine agonist or dopamine agonists to achieve therapeutic effect, reduced circulating levels of active metabolites of the drug, increased ratio of circulating level of drug to metabolites, improved therapeutic index (i.e., drug effect/drug side effect), elimination of first-pass metabolism, and avoidance of gastrointestinal side effects due to drug interaction with dopamine agonist binding sites within the gut. Additionally, dosage forms disclosed herein have the advantage that they can be self-administered by patients without close medical supervision.

Use of the compositions described herein to treat metabolic disease accomplishes improved results relative to an equivalent dosage of orally administered dopamine agonists. In one aspect, smaller dosages of parental formulations can produce an effective dose equivalent to higher dosages of oral formulations of the same dopamine agonist(s). In another aspect, administration of smaller dosages of dopamine agonists results in reduced amounts of dopamine agonist(s) metabolites, particularly in the case of ergot-related dopamine agonists. In still another aspect, administration of parenteral formulations results in reduced production of metabolites thought to have biological activities that counteract the activities of the parent compound as compared to administration of oral formulations having the same amount of active agent. The inventors of the present application have also surprisingly found that dopamine agonists used in the treatment of metabolic disease, when used at the appropriate dosages and at pre-determined times of day as described herein are more effective when the active metabolite levels are reduced. Thus, parenteral dosage forms have a greater comparative therapeutic effectiveness relative to equi-molar circulating concentrations of the oral dosage forms in part because of the reduced relative levels of active metabolites.

Accordingly, a parenteral dosage form of dopamine agonist(s) that produces an equivalent $T_{max}$ level as that of an oral formulation of dopamine agonist(s) can increase the relative dopamine agonist parent/metabolite ratio in the circulation and, thus, improve the effectiveness of the dopamine agonist(s) in treating metabolic disease relative to an equivalent $T_{max}$ level of orally administered dopamine agonist(s). For example, a therapeutically effective amount of dopamine agonist(s) administered via an oral dosage form for treatment of metabolic disease is 1 mg per day and will produce 100 μg of agonist(s) and 900 μg of metabolites (due to first-pass metabolism) in the circulation. By contrast, a parenteral dosage form may achieve the same "effective" dose of dopamine agonist(s) in the circulation resulting from the administration of 120 μg of dopamine agonist(s) since there is little or no first-pass metabolism of the drug and only about 20 μg of metabolites are produced over time. Accordingly, the ratio of drug/metabolite is 100/900 for the oral administration and 100/20 for the parenteral formulation. Thus, the counteractive effects of the metabolites on the metabolic activity of the parent compound(s) are reduced, particularly when administered as described herein.

In another aspect, the dosage forms disclosed herein are stable, remaining suitable for administration over a prolonged period in storage. Irreversible agglomeration in the dosage forms disclosed herein is eliminated or reduced, even in storage for some months.

Active dopamine agonist agents for inclusion in dosage forms disclosed herein include, for example and without limitation, non-ergot and ergot-related derivatives. Active dopamine agonist agents include $D_1$ dopamine receptor agonists and/or $D_2$ dopamine receptor agonists. In certain embodiments a $D_1$ dopamine agonist is administered to a subject in need of treatment. In other embodiments a $D_2$ dopamine agonist is administered to a subject in need of treatment. In yet other embodiments of the present invention, a $D_1$ dopamine agonist is administered in conjunction with a $D_2$ dopamine agonist to a subject in need of treatment.

Active peripheral acting agents for inclusion in dosage forms disclosed herein include, without limitation, anti-hypertensive, anti-inflammatory, anti-coagulative, anti-hypercholesterolemic, anti-hypertriglyceridemic, and/or anti-hyperglycemic agents. In certain embodiments, an active peripheral acting agent is an HMGCoA reductase inhibitor.

The dosage forms disclosed herein may comprise, consist essentially of, or contain $D_1$ dopamine receptor agonist, alone or in combination with a $D_2$ dopamine receptor agonist, and further optionally in combination with one or more active peripheral acting agent.

As used herein the terms "conjoined" treatment or administration or treatment or administration "in conjunction" mean that a subject receives at least a first amount of a first active agent and a second amount of a second active agent. Active agents may be administered in a single formulation or dosage form or in separate dosage forms. Agents administered in separate dosage forms may be administered at the same time or at different times. For example a $D_1$ agonist and $D_2$ agonist can be administered at the same time (in the same dosage form or in two or more divided dosage forms) or sequentially at different times and in different dosage forms.

Therapeutically effective amounts of $D_1$ agonist for humans and vertebrates when administered parenterally alone (not conjoined to a $D_2$ agonist) are typically within the range of about 1.0 μg/kg/day to about 10.0 mg/kg/day. Preferably, the therapeutically effective amounts of $D_1$ agonist for humans and vertebrates when administered alone are typically within the range of about 1.0 μg/kg/day to about 7.0 mg/kg/day. More preferably, the therapeutically effective amounts of $D_1$ agonist for humans and vertebrates when administered alone are typically within the range of about 1.0 μg/kg/day to about 5.0 mg/kg/day. Most preferably, the therapeutically effective amounts of $D_1$ agonist for humans and vertebrates when administered alone are typically within the range of about 2.0 μg/kg/day to about 3.0 mg/kg/day.

Therapeutically effective amounts of $D_2$ agonist for humans and vertebrates when administered parenterally alone (not conjoined to a $D_1$ agonist) are typically within the range of about 0.5 μg/kg/day to about 300 μg/kg/day. Preferably, the therapeutically effective amounts of $D_2$ agonist for humans and vertebrates when administered alone are typically within the range of about 0.5 μg/kg/day to about 250 μg/kg/day. More preferably, the therapeutically effective amounts of $D_2$ agonist for humans and vertebrates when administered alone are typically within the range of about 0.5 μg/kg/day to about 200 μg/kg/day. Most preferably, the therapeutically effective amounts of $D_2$ agonist for humans and vertebrates when administered alone are typically within the range of about 1.0 μg/kg/day to about 150 μg/kg/day.

Where therapeutically effective amounts of $D_1$ and $D_2$ agonist(s) for humans and vertebrates are administered parenterally in conjunction, about 15% less of each of the $D_1$ and $D_2$ agonist(s) may be used. Preferably, where therapeutically effective amounts of $D_1$ and $D_2$ agonist(s) for humans and vertebrates are administered parenterally in conjunction about 17% less of each of the $D_1$ and $D_2$ agonist(s) are used. More preferably, where therapeutically effective amounts of $D_1$ and $D_2$ agonist(s) for humans and vertebrates are administered parenterally in conjunction about 20% less of each of the $D_1$ and $D_2$ agonist(s) are used. Most preferably where therapeutically effective amounts of $D_1$ and $D_2$ agonist(s) for humans and vertebrates are administered parenterally in conjunction about at least 25% less of each of the $D_1$ and $D_2$ agonist(s) are used.

A dopamine agonist in a non-colloidal form is typically compounded to a particle size ($d_{90}$) in the range of about 5 to 175 μm. Preferably, the dopamine agonist in the non-colloidal form is compounded to a particle size in the range of about 5 to 150 μm. More preferably, the dopamine agonist in the non-colloidal form is typically compounded to a particle size in the range of about 5 to 125 μm. Most preferably, the dopamine agonist in the non-colloidal form can be compounded to a particle size of about 10 to 100 μm.

A dopamine agonist in colloidal form is typically compounded to a particle size in the range of about 0.1 to 5.0 μm. Preferably, the dopamine agonist in colloidal form is typically compounded to a particle size in the range of about 0.1 to 3.0 μm. More preferably, the dopamine agonist in colloidal form is typically compounded to a particle size in the range of about 0.1 to 2.0 μm. Most preferably, the dopamine agonist in colloidal form is typically compounded to a particle size in the range of about 0.1 to 1.0 μm.

A $D_1$ dopamine agonist activates or potentiates $D_1$ dopamine receptors or $D_1$-like receptors such as $D_1$ and $D_5$ dopamine receptors. The $D_1$ agonist is also a selective agonist for the $D_1$ receptor over the $D_2$ receptor (i.e., the compound has a lower $K_i$ or $EC_{50}$ for the $D_1$ receptor than the $D_2$ receptor). In one embodiment, the $D_1$ agonist is a weak agonist (e.g., $K_i$ or $EC_{50}$ of greater than 1 μM or 1 mM) or a partial agonist (binding affinity less than that of endogenous dopamine for D2 sites) or is not a $D_2$ agonist (e.g., $K_i$ or $EC_{50}$ of greater than 10 mM).

$D_1$ dopamine agonists that are capable of activating or potentiating $D_1$ dopamine receptors are well known in the art. Examples of $D_1$ agonists include, without limitation, dopamine, apomorphine, SKF38393, dihydrexidine, SKF 75670, SKF 82957, SKF 81297, SKF 82958, SKF 82598, A77636, A68930, and SKF 82526 (fenoldopam), and racemic trans-10,11-dihydroxy 5,6,6a,7,8,12b-hexahydro and related benzazepine analogs, and those $D_1$ agonists disclosed in the references cited herein. A preferred $D_1$ dopamine agonist is SKF 38393 or apomorphine. See e.g., U.S. Pat. No. 6,855,707, the contents of which are incorporated herein by reference.

$D_2$ dopamine agonists activate or potentiate $D_2$ dopamine receptors (e.g., $D_2$, $D_2$ short and $D_2$ long receptors, $D_4$, and $D_4$ dopamine receptors). In one embodiment, the $D_2$ agonist is a selective agonist for the $D_2$ receptor over the $D_1$ receptor. In a further embodiment, the $D_2$ agonist is a weak $D_1$ agonist or is not a $D_1$ agonist. Examples of $D_2$ dopamine agonists are well known in the art.

Ergot-related $D_2$ agonists include, for example and without limitation, 2-bromo-α-ergocriptine (bromocriptine), terguride, dihydroergotoxine (hydergine), erfotoxine, 6-methyl 8 β-carbobenzyloxy-aminoethyl-10-α-ergoline, 8-acylaminoergoline, 6-methyl-8-α-(N-acyl)amino-9-ergoline, lisuride, dihydro-alpha-ergocriptine, dihydro-alpha-ergotoxine, 6-methyl-8-α-(N-phenyl-acety)amino-9-ergoline, ergocornine, 9,10-dihydroergocornine, any D-2-halo-6-alkyl-8-substituted ergoline, and D-2-bromo-6-methyl-8-cyanomethyl-ergoline. Of these bromocriptine or lisuride or ergot-related compounds with little or no serotonin 5HT2B receptor agonist activity is most preferred.

Examples of non-ergot-related dopamine D2 agonists include, without limitation, ropinirole, piribedil, apomorphine, quinelorane, and talipexole.

Examples of peripheral acting agents are, without limitation, substances that exhibit and anti-hypertensive, anti-inflammatory, anti-hypercholesterolemic, anti-hypertriglyceridemic, and/or anti-hyperglycemic effect.

Anti-hyptertensive agents include, for example and without limitation, agents that are angiotensin converting enzyme (ACE) inhibitors, angiotensin II receptor blockers (ARBs), calcium channel blockers, β-blockers, α-blockers, and diuretics. Examples of anti-hypertensive agents include, for example and without limitation, bumetanide, ethacrynic acid, furosemide, torsemide, chlortalidone, epitizide, hydrochlorothiazide, chlorothiazide, bendroflumethiazide, indapamide, metolazone, amiloride, triamterene, spironolactone, atenolol, metoprolol, nadolol, oxprenolol, pindolol, propranolol, timolol, doxazosin, phentolamine, indoramin, phenoxybenzamine, prazosin, terazosin, tolazoline, bucindolol, carvedilol, labetalol, clonidine, methyldopa, amlodipine, felodipine, isradipine, nifedipine, nimodipine, nitrendipine, diltiazem, verapamil, captopril, enalapril, fosinopril, lisinopril, perindopril, quinapril, ramipril, trandopril, benzapril, candesartan, eprosartan, irbesartan, losartan, olmesartan, telmisartan, valsartan, spironolactone, sodium nitroprusside, guanabenz, guanethidine, and reserpine.

Anti-hypercholesterolemic agents include, for example and without limitation, HMGCoA reductase inhibitors agents (statins) and agents that block cholesterol absorption. Examples of anti-hypercholesterolemic agents include, for example and without limitation, atorvastatin, cerivastatin, fluvastatin, lovastatin, mevastatin, pravastatin, pitavastatin, rosuvastatin, simvastatin, cholestyramine, sitosterol, ezetimibe, gemfibrozil, clofibrate, nicotinic acid, colestipol, and colesevelam. Preferred statin agents are atorvastatin, cerivastatin, fluvastatin, lovastatin, mevastatin, pravastatin, pitavastatin, rosuvastatin, and simvastatin.

Anti-hypertriglyceridemic agents include, for example and without limitation, fibrates. Examples of anti-hypertriglyceridemic agents include, for example and without limitation, gembfibrozil, clofibrate, bezafibrate, and walnut oil.

Anti-hyperglycemic agents include, for example and without limitation, agents that are biguanides, insulin secretagouges, and insulin sensitizers. Examples of anti-hyperglycemic agents include, for example and without limitation, insulin, sulfonylurea-based medications, metformin, repaglinide, nateglinide, glucosidase inhibitors, thiazolidinediones, GLP-1 analogs, and DPP IV inhibitors.

Dosage forms can include a dopamine agonist or dopamine agonists formulated to achieve either faster or slower release of the drug into the blood stream. Dosage forms are solid or free-flowing.

The term "solid" as used herein refers to a substance that is solid or semi-solid at room temperature. Hence, as used herein, a "solid" substance may become liquid at, e.g., body temperature.

In certain embodiments, dosage forms can be formulated to have a biphasic release of active component, e.g., a fast release (a/k/a immediate release) phase and a slow release (a/k/a delayed release) phase. The faster and slower release of the active agent may be separated physically, by dividing components having different compositions, wherein each composition is characterized by faster or slower dissolution. In another embodiment, fast and slow release phases are accomplished in a single, combined dosage form which may comprise, e.g., an outer layer that is characterized by fast dissolution and an inner layer that is characterized by slower dissolution.

In other embodiments, a dosage form may comprise a dissolved dopamine agonist that is characterized by fast dissolution and a colloidal suspension of dopamine agonist that is characterized by slower dissolution. Inclusion of a dopamine agonist having a small particle size of about 0.02 to about 5.0 μm in a colloidal suspension promotes rapid dissolution and absorption. However, the rapid dissolution and absorption of the dopamine agonist having a small particle size of about 0.02 to about 5.0 μm in a colloidal suspension is slower than a dopamine agonist already in solution. Preferably, small particle size dopamine agonist is about 0.1 to about 3.0 μm. More preferably, small particle size dopamine agonist is about 0.1 to about 2.0 μm. Most preferably, small particle size dopamine agonist is about 0.1 to about 1.0 μm.

Inclusion of dopamine agonist having a larger particle size ($d_{90}$) of greater than about 5.0 μm promotes slower dissolution and absorption. Preferably, inclusion of dopamine agonist having a larger particle size ($d_{90}$) of greater than about 5-150 μm promotes slower dissolution and absorption. More preferably, inclusion of dopamine agonist having a larger particle size ($d_{90}$) of greater than about 5-125 μm promotes slower dissolution and absorption. Most preferably, inclusion of dopamine agonist having a larger particle size ($d_{90}$) of greater than about 10-100 μm promotes slower dissolution and absorption.

In certain embodiments, small and large sized dopamine agonist(s) particles are present in formulations at an approximate ratio of 50/50. More preferably, small and large sized dopamine agonist(s) particles are present in an approximate ratio of 60/40. Most preferably, small and large sized dopamine agonist(s) particles are present in an approximate ratio of 70/30.

In certain embodiments, the small particle size component is 1.0 μm within a tablet or other solid dosage form and the large particle size is 1 to 100 μm.

A prolactin inhibitor (such as bromocriptine) can be administered to a mammalian subject (particularly to a human) at a pre-determined time during a 24-hour period if that subject has abnormally high daytime prolactin levels (at least 1 Standard Error of the Mean (SEM) higher than any of the normal daytime levels for a subject of the same species and sex). The administration and its timing are designed to decrease the subject's abnormally high daytime prolactin levels. However, a prolactin stimulator may need to be administered at a different pre-determined time during a 24-hour period, if the subject has abnormally low night-time prolactin levels, to increase these night-time prolactin levels to be preferably no lower than approximately the normal night-time prolactin levels for the same sex. It is also possible that both a prolactin inhibitor and a prolactin stimulator may need to be administered at different times to the same subject to bring about both a decrease in daytime prolactin levels and an increase in night-time prolactin levels.

Dosage formulations may further comprise, without limitation, one or more of the following: excipients, non-aqueous solvent, pharmaceutically acceptable suspending medium, carriers or diluents, surface active compounds, regulators for adjusting the osmolality, bioadhesives, polymers, permeabilizing agents, stabilizers, anhydrous mucosal tissue irritant-reducing agents, fillers, binders, disintegrants, lubricants, flavoring agents and sweeteners, gelling agents, inert gas, antioxidants, preservatives, wetting agents, surfactants, release controlling agents, dyes, binders, suspending agents and dispersing agents, colorants, film forming agents, plasticizers or any combination of two or more of the foregoing.

Excipients used in dosage forms will vary according to the type of parenteral dosage form. Suitable excipients for dosage forms are well known to those of skill in the art and will vary according to the active agent, mode of administration, and desired release profile of active agent. Non-limiting examples of the suitable excipients for use in formulations are provided below.

The term "pharmaceutically acceptable excipient(s)" is intended to denote any material, which is inert in the sense that it substantially does not have a therapeutic and/or prophylactic effect per se. Such an excipient is added with the purpose of making it possible to obtain a pharmaceutical composition having acceptable technical properties.

Examples of non-aqueous solvents include, without limitation, propylene glycol, glycerol, short-chain substituted or non-substituted alcohols such as ethanol, isopropanol, or propanol. In a certain embodiment, the non-aqueous solvents may include, without limitation, various glycols and/or alcohols alone or in combination, so that therapeutic doses contain non-toxic solvent volumes of, e.g., 0.02 to 0.5 ml.

Examples of pharmaceutically acceptable suspending mediums or matrices include, without limitation, synthetic, semisynthetic or natural oils which can preferably be employed are medium chain length triglycerides with a chain length of from $C_8$ to $C_{10}$ in the carboxylic acid moiety, soybean oil, sesame oil, peanut oil, olive oil, coconut oil, castor oil, sunflower oil, safflower oil or the corresponding hydrogenated oils or mixtures of at least two of the aforementioned oils, bentonite, ethoxylated isostearyl alcohols, polyoxyethylene sorbitol and sorbitan esters, microcrystalline cellulose or derivatives thereof, plant gums, polyetheleneglycols of various size, aluminum metahydroxide, agar-agar and tragacanth, gelatins, or mixtures of two or more of these substances, and the like.

Examples of pharmaceutically acceptable dispersing and suspending agents include, but are not limited to, synthetic and natural gums, such as vegetable gum, tragacanth, acacia, alginate, dextran, sodium carboxymethylcellulose, methylcellulose, polyvinyl-pyrrolidone and gelatin.

Examples of suitable pharmaceutically acceptable carriers or diluents include, but are not limited to, ethanol, water, glycerol, propylene glycol, glycerin, diethylene glycol monoethylether, vitamin A and E oils, mineral oil, PPG2 myristyl propionate, magnesium carbonate, potassium phosphate, silicon dioxide, vegetable oils such as castor oil and derivatives thereof, plant gums, gelatin, animal oils, solketal, calcium carbonate, dibasic calcium phosphate, tribasic calcium phosphate, calcium sulfate, microcrystalline cellulose, powdered cellulose, dextrans, dextrin, dextrose, fructose, kaolin, lactose, mannitol, sorbitol, starch, pregelatinized starch, sucrose, sugar etc.

Examples of surface active compounds include, without limitation, polyalkylene glycols such as polyethylene glycols, polypropylene glycols or ethylene oxide, propylene oxide block copolymers, phospholipids, ethers or esters of saturated or unsaturated fatty alcohols or fatty acids with polyalkylene glycols such as polyethylene glycols or polypropylene glycols, polysorbates such as mono-, di- or tri-esters of saturated or unsaturated fatty acids, particularly preferably oleic acid, lauric acid, palmitic acid or stearic acid, and sorbitol and/or its anhydride, each of which may have up to 20 mol of ethylene oxide units per mole of sorbitol or anhydride, preferably polyethoxysorbitan monolaurate with 20 ethylene oxide units, polyethoxysorbitan monolaurate with 4 ethylene oxide units, polyethoxysorbitan monopalmitate with 20 ethylene oxide units, polyethoxysorbitan monostearate with 20 ethylene oxide units, polyethoxysorbitan monostearate with 4 ethylene oxide units, polyethoxysorbitan tristearate with 20 ethylene oxide units, polyethoxysorbitan monooleate with 20 ethylene oxide units, polyethoxysorbitan monooleate with 5 ethylene oxide units or polyethoxysorbitan trioleate with 20 ethylene oxide units, or a mixture of at least two of the aforementioned surface-active compounds.

Examples of regulators for adjusting the osmolality include, without limitation, water-soluble, physiologically tolerated compounds such as inorganic salts, e.g., alkali metal salts, preferably sodium chloride, sugars, e.g. sucrose or dextrose, sugar alcohols, e.g., mannitol, or polyalkylene glycols, e.g., polyethylene glycols, preferably having a molecular weight of from 1,000 to 8,000 g/mol. It is also possible to use a mixture of at least two representatives of different classes of regulators or at least two representatives of one class of regulators for adjusting the osmolality.

Bioadhesives are included, for example, in adhesive tablets, solutions, colloidal suspensions, gels, ointments, patches, films, pastes, and lozenges. Examples of bioadhesives polymers include, without limitation, Benecel MP814, Kollidon, chitosan, cellulose derivatives, Carbopol 934P, Carbopol 974P, 1Voveou AA-1, carbopole resins, carbomer, xanthan gum, polycarbophil and polyethylene oxide combined with an inert diluent and an active ingredient, and ionic polysaccharides. Several synthetic and semi-synthetic bioadhesive polymers of different molecular weight and variations in degree of substitution include, without limitation, hydroxyethylcellulose, polyvinylalcohol, polyacrylic acid, sodium carboxymethylcellulose, polyvinylpyrrolidone, polyethylene glycols and others. Mucosal adhesion of these bioadhesive formulations is based on the interpenetration of hydrated hydrocolloid chains of the bioadhesive formulation and glycoprotein chains of the oral mucosa.

Examples of suitable film forming agents include, but are not limited to, hydroxypropylmethylcellulose, ethylcellulose and polymethacrylates.

Examples of suitable plasticizers include, but are not limited to, polyethylene glycols of different molecular weights (e.g., 200-8000 Da), plant gums, and propylene glycol and triethyl citrate.

Examples of permeabilizing agents comprise, without limitation, bile salts, fatty acids, fatty acid derivatives, fatty acid esters, such as laureate, myristate and stearate monoesters of polyethylene glycol, enamine derivatives and alpha-keto aldehydes; sodium cholate; sodium glycocholate; sodium deoxycholate; sodium lauryl sulfate; sodium salicylate; sodium ethylenediaminetetraacetic acid (EDTA); aprotinin; azone; sodium 5-methoxysalicylate; 1-oleylazacycloheptan-2-one; and/or silicas with a high affinity for aqueous solvents, such as the precipitated silica better known by the trade mark Syloid®, maltodextrins, β-cyclodextrins, surfactants, chelators, cyclodextrins, chitosan, and lower alcohols.

Examples of stabilizers include, without limitation, citric acid, ascorbic acid, oleic acid, caprylic acid, capric acid, polyvinylpyrrolidone, waxes, block co-polymers, poloxamers, Poloxamer 188 and 407, poloxamines, Poloxamine 908, polyvinyl pyrrolidone, polyvinyl alcohol, gelatine, polysaccharide, hyaluronic acid, chitosan, derivatives of chitosan, polyacryl acid, derivatives of polyacryl acid, polycarbophil, cellulose derivatives, methyl cellulose, hydroxypropyl cellulose, carboxymethyl cellulose, sugar esters, saccharose monostearate, sodium citrate individually, fatty acids, fatty alcohols, alcohols, long chain fatty acid esters, long chain ethers, hydrophilic derivatives of fatty acids, polyvinylethers, polyvinyl alcohols, hydrocarbons, hydrophobic polymers, moisture-absorbing polymers, and combinations thereof.

Examples of anhydrous mucosal tissue irritant-reducing agent include, without limitation, plant oils like but not limited to olive oil, corn oil or mineral oil.

Examples of fillers include, without limitation, microcellulose, e.g., ProSolv; Pharmaburst; Cab-o-sil; and saccharides, e.g., mannitol, lactose, xylitol and mixtures thereof.

Examples of suitable binders include, without limitation, either individually or in combination, such binding agents as sucrose, gelatin, glucose, starch, cellulose materials, polyethylene glycols, povidone, methylcellulose, sodium carboxymethylcellulose, sodium alginate, agar, alginic acid and salts of alginic acid, calcium carrageenan, magnesium aluminum silicate, polyethylene glycol, guar gum, polysaccharide acids, bentonites, polyvinylpyrrolidone (povidone), hydroxymethyl polyvinyl pyrolidone, polymethacrylates (such as Eudragit), methylcellulose, hydroxypropyl methylcellulose (HPMC), hydroxypropyl cellulose (Klucel™), ethyl cellulose (Ethocel™), hydroxypropylmethylcellulose, pregelatinized starch (such as National™ 1511 and Starch 1500), sucrose, lactose, starch paste, povidone polyethylene glycol, Pullulan and corn syrup, waxes, and natural and synthetic gums, such as acacia, tragacanth, vegetable gum, castor oil, microcrystalline cellulose, dextrin, liquid glucose, guar gum, pectin, PEG, povidone, pregelatinized starch etc.

Examples of suitable disintegrants include, without limitation, starches such as maize starch and rice starch, cross-linked N-vinyl-2-pyrrolidone (CLPVP), alginic acid or alginates, microcrystalline cellulose, hydroxypropyl cellulose and other cellulose derivatives, croscarmellose sodium, crospovidone, polacrillin potassium, starch, pregelatinized starch, Pharmablast® carboxymethyl starch (e.g. Primogel® and Explotab®), sodium starch glycolate, and formaldehyde casein. Effervescent disintegrants include without limitation, for example, starch, potassium bicarbonate, and sodium bicarbonate in combination with citric or tartaric acids. The disintegrant is present as an intra-granular disintegrant or extra-granular disintegrant.

Examples of suitable lubricants include, without limitation, sodium oleate, sodium stearate, sodium stearyl fumarate, stearic acid, magnesium stearate, sodium benzoate, sodium acetate, sodium chloride, calcium stearate or other metallic stearate, talc, waxes and glycerides, light mineral oil, PEG, glyceryl behenate, colloidal silica, hydrogenated vegetable oils, corn starch, sodium stearyl fumarate, polyethylene glycols, alkyl sulfates, sodium benzoate, and sodium acetate.

Examples of suitable flavoring agents include, without limitation, menthol, peppermint, vanilla, fruit flavorings, and sweeteners, e.g., aspartame or sodium saccharinate.

Examples of gelling agents include, without limitation, polyvinylpyrrolidone, hydroxypropylmethyl cellulose, plant gums, and the like.

Examples of suitable inert gases include, without limitation, nitrogen, helium, etc.

Examples of additional additives include, but are not limited to, sorbitol, talc, and stearic acid.

Examples of suitable antioxidants include, but are not limited to citric acid, ascorbic acid, ascobyl palmitate, butylated hydroxyanisole, butylated hydroxytoluene (BHT), monothioglycerol, potassium metabisulfite, propylgallate, tocoferol excipients.

Examples of suitable wetting agents include, but are not limited to polysorbate, sodium lauryl sulfate, sorbitan monolaurate, sorbitan monooleate, sorbitan monopalmitate, sorbitan monostearate.

Examples of suitable release controlling agents include, but are not limited to hydroxypropylmethylcellulose, hydroxypropylcellulose, ethylcellulose, hydroxyethylcellulose.

Examples of surfactants include, without limitation, anionic and non-ionic surfactants such as sodium lauryl sulfate, poloxamers (copolymers of polyoxyethylene and polyoxypropylene), natural or synthetic lecitins as well as esters of sorbitan and fatty acids, such as Span® (Commercially available from Sigma-Aldrich Co., St. Louis, Mo.), esters of polyoxyethylenesorbitan and fatty acids, such as Polysorbates or Polysorbate® (Commercially available from Spectrum Chemical, Gardena Calif.), polyoxyethylene stearates, such as Myrj® (Commercially available from Uniqema, New Castle, Del.), polyethoxylated fatty acids such as, e.g., fatty acid mono- or diesters of polyethylene glycol or mixtures thereof such as, e.g., mono- or diesters of polyethylene glycol with lauric acid, oleic acid, stearic acid, myristic acid, ricinoleic acid, and the polyethylene glycol is selected from PEG 4, PEG 5, PEG 6, PEG 7, PEG 8, PEG 9, PEG 10, PEG 12, PEG 15, PEG 20, PEG 25, PEG 30, PEG 32, PEG 40, PEG 45, PEG 50, PEG 55, PEG 100, PEG 200, PEG 400, PEG 600, PEG 800, PEG 1000, PEG 2000, PEG 3000, PEG 4000, PEG 5000, PEG 6000, PEG 7000, PEG 8000, PEG 9000, PEG 1000, PEG 10,000, PEG 15,000, PEG 20,000, PEG 35,000, polyethylene glycol glycerol fatty acid esters, i.e. esters like the above-mentioned but in the form of glyceryl esters of the individual fatty acids; glycerol, propylene glycol, ethylene glycol, PEG or sorbitol esters with e.g., vegetable oils like e.g., hydrogenated castor oil, almond oil, palm kernel oil, castor oil, apricot kernel oil, olive oil, peanut oil, hydrogenated palm kernel oil and the like, polyglycerized fatty acids like e.g., polyglycerol stearate, polyglycerol oleate, polyglycerol ricinoleate, polyglycerol linoleate, propylene glycol fatty acid esters such as, e.g., propylene glycol monolaurate, propylene glycol ricinoleate and the like, mono- and diglycerides like e.g. glyceryl monooleate, glyceryl dioleate, glyceryl mono- and/or dioleate, glyceryl caprylate, glyceryl caprate etc.; sterol and sterol derivatives; polyethylene glycol sorbitan fatty acid esters (PEG-sorbitan fatty acid esters) such as esters of PEG with the various molecular weights indicated above, and the various Tween® series (from ICI America, Inc.); polyethylene glycol alkyl ethers such as, e.g., PEG oleyl ether and PEG lauryl ether; sugar esters like, e.g., sucrose monopalmitate and sucrose monolaurate; polyethylene glycol alkyl phenols like, e.g., the Triton® X or N series (Union Carbide Chemicals & Plastics Technology Corporation); polyoxyethylene-polyoxypropylene block copolymers such as, e.g., the Pluronic® series from BASF Aktiengesellschaft, the Synperonic® series from ICI America, Inc., Emkalyx, Lutrol® from BASF Aktiengesellschaft, Supronic etc.

The amount of compound(s) acting as surfactant is adjusted when employed for such purpose, so as to moderate the solubility, permeability, and bioavailability of dopamine agonist(s). Preferably the ratio of surfactant to dopamine agonist(s) on a mass basis is from about 0.001:1 to about 1:1, more preferably from about 0.005:1 to 0.6:1 and most preferably from about 0.01:1 to about 0.25:1.

Examples of suitable lubricants and/or glidants include, without limitation, either individually or in combination, such lubricants and/or glidants as glyceryl behenate (Compritol™ 888); metallic stearates (e.g., calcium, sodium stearates, or other long chain fatty acid salts); stearic acid; hydrogenated vegetable oils (e.g., Sterotex™); talc; waxes; Stearowet™; boric acid; sodium benzoate and sodium acetate; sodium chloride; DL-Leucine; polyethylene glycols (e.g., Carbowax™ 4000 and Carbowax™ 6000); sodium oleate; sodium benzoate; sodium acetate; sodium lauryl sulfate; sodium stearyl fumarate (Pruv™); and magnesium lauryl sulfate.

Additional examples of suitable anti-adherents or glidants include, without limitation, either individually or in combination, such anti-adherents as talc, cornstarch, DL-Leucine, sodium lauryl sulfate, and metallic stearates.

Suitable examples of preservatives include, without limitation, citric acid, vitamin C, vitamin E, 1,1,1-trichloro-2-methyl-2-propanol, phenylethyl alcohol, sorbic acid, benzyl alcohol, alkylbenzyldimethylammonium chloride with a chain length of from $C_8$ to $C_{18}$ in the alkyl moiety, m-cresol or alkyl-4-hydroxybenzoate.

The term "parenteral dosage form" is defined herein to mean a drug dosage form that provides for the absorption of a substantial amount of the drug through other than the gastric and/or intestinal mucosa of the GI tract.

Routes of parenteral administration include, without limitation, buccal, sublingual, subcutaneous, nasal, oral, otic, ocular, rectal, vaginal, or upper respiratory mucosa, or through the skin or lungs. Accordingly, the dosage forms include, without limitation, injection, oral, otic, ophthalmic, or nasal sprays or drops, sublingual and/or buccal sprays, drops, tablets, solutions, colloidal suspensions, and/or ointments, hard capsule and soft capsules, tablets, coated tablets, or sachets, lozenge, films, chewing gum, chewable tablet, liquid gargle, skin patch, ointment, lotion, or cream, a respiratory inhaler, aerosols, or rectal or vaginal suppository.

Dosage forms may be administered by injection. Injection can be, for example, subcutaneous, intradermal, and/or intraperitoneal.

The pH of the solution or solvent-based dosage forms of the invention should preferably be in the range from pH 3 to pH 9 in order to avoid further risks of cell and tissue damage.

The following dosage forms are provided as non-limiting examples. Dosage forms for nasal administration include nasal sprays and/or drops and/or application of nasal ointments. Dosage forms for sublingual or buccal administration include oral spays, drops, solutions, colloidal suspensions, tablets, ointments, lozenges, films, chewing gums, chewable tablets, and/or liquid gargle. Dosage forms for auricular or ocular administration include sprays, drops, ointments, lotions and/or creams. Dosage forms for rectal administration include suppository, spray, drops, ointment, lotion and/or cream. Dosage forms for vaginal administration include suppository, spray, drops, ointment, lotion and/or cream. Dosage forms for upper respiratory mucosa or pulmonary administration include a respiratory inhaler, e.g., nebulizer. Dosage forms for transdermal administration include skin patches, dermal spray, drops, ointment, lotion and/or cream.

Solid parenteral dosage forms preferably include a the dopamine agonist (prefereably bromocriptine mesylate), an non-acrylic type of mucoadhesive (e.g., PVP, Benecel and not Carbopol®), and citric acid to enhance stability and accelerate release of dopamine agonist. In the absence of citric acid, API was unstable in the acrylic based solutions (50% of the drug decomposed after 90 minutes). Citric acid enhanced the stability of the dopamine agonist preparations.

Preferred routes of administration are, subcutaneous injection, buccal, sublingual, nasal and transdermal. More preferred routes of administration are buccal, sublingual and nasal. Particularly preferred dosage forms include subcutaneous injections, sublingual or buccal dosage forms, and skin patches.

Where the dosage form is to be injected or administered via a liquid carrier (as for example in sublingual administrations) it may be administered using two different vehicles for the two different solutions in one syringe. Such a syringe may have two vessels and ports, each specific to the two solutions. Alternatively, the two different solutions could be combined into one vessel.

Where parenteral administration is subcutaneous, suitable forms for injection may include a hydrophobic or hydrophilic suspension medium.

One embodiment of the formulations disclosed herein therefore comprises suspending the salt of the active ingredient or active ingredients in a hydrophobic pharmaceutically acceptable suspending medium. This hydrophobic suspending medium may preferably be based on pharmaceutically acceptable synthetic, semisynthetic or natural oils or mixtures of at least two of these oils.

The suspending medium is provided preferably in amounts of from 10 to 90% by weight based on the suspending medium.

It is also possible to employ dosage forms via a physiologically tolerated hydrophilic suspending medium and wherein the active ingredient is a salt being a $D_1$ agonist and/or a non-ergot-related $D_2$ agonist. The hydrophilic suspending medium is preferably based on water.

Besides one or more regulators to adjust the osmolality, the dosage forms may further comprise one or more representatives the other aforementioned excipients.

In order to minimize or completely eliminate the risk of cell and tissue damage, the osmolality, i.e., the tonicity of the aqueous dosage forms (if so employed) of the invention which are to be administered parenterally, is preferably adjusted so that they are isotonic or at least approximately isotonic to the physiological osmolality. The osmolality of the dosage forms of the invention which can be administered parenterally is therefore preferably adjusted so that it is in the range from 250 to 400 mOsm/kg, particularly preferably in the range from 260 to 320 mOsm/kg and very particularly preferably in the range from 280 to 300 mOsm/kg.

It is also possible where appropriate to employ a regulator to adjust different properties of the dosage forms. For example, a surface-active compound can also be used to adjust the osmolality of the administration environment (e.g., sublingual or buccal area).

Dosage forms may further comprise one or more physiologically tolerated surface-active compounds.

Parenteral dosage forms are typically administered in volumes from about 0.01 to 0.75 ml. Preferably, the volume to be administered parenterally is from about 0.01 to about 0.5 ml, more preferably from about 0.01 to about 0.3 ml, and most preferably from about 0.01 to about 0.2 ml.

Where the dosage form is to be taken orally, the dosage form is preferably suitable for buccal or sublingual administration of the drug via the mucosa of the oral cavity. More preferably, the dosage form is of the sublingual type suitable for administration of the drug via the mucosa of the oral cavity.

Typically, the buccal dosage form is placed in the buccal cavity between the gum and the cheek, where it dissolves in the subject's saliva, releasing the medicament into the buccal cavity in close proximity to the capillary bed of the oral mucosa. The sublingual dosage form is placed beneath the tongue where it dissolves in the saliva to release the drug in close proximity to the capillary bed of the oral mucosa for transmucosal absorption.

The pharmaceutically active agent in these oral dosage forms enters the blood in the capillary bed by diffusion through the mucosal tissue and is distributed in the bloodstream to the rest of the body. The rate at which the active agent is supplied to the body depends upon, among other things, the rate at which the dosage form dissolves in the mouth. The physical properties of the dosage form determine the degree of contact with the mucosal tissues and consequently the efficiency of the absorption of the medicament.

Where parenteral administration is accomplished via oral administration, absorption through the gastric and/or intestinal mucosa can be substantially prevented by the use of certain components in the formulation such as bioadhesives, permeabilizing agents and stabilizers that prevent and/or reduce the introduction of dopamine agonists into the gastric and/or intestinal mucosa of the GI tract.

In certain embodiments, orally administered (sublingual or buccal) parental dosage forms comprise both rapid and slow soluble components when introduced into the oral cavity as a function of the two distinct formulations within the single dosage form or dosage applicator.

Solid oral dosage forms (comprising fast and slow absorption components) may be characterized by their dissolution times in vitro. Solid oral dosage forms (comprising fast and slow absorption components) typically exhibit a dissolution time of about ten seconds to about 100 minutes. Preferably, oral dosage forms exhibit a dissolution time of about ten seconds to about 50 minutes. More preferably, oral dosage forms exhibit a dissolution time of about 10 seconds to about 30 minutes. Most preferably, oral dosage forms exhibit a fast dissolution time of about 10 seconds to about 20 minutes.

In certain embodiments, an oral dosage form is a film, e.g. a buccal film. The mechanical, bioadhesive, and swelling properties of films are controlled to be suitable for buccal administration. Films for buccal administration are preferably flexible, elastic, soft yet sufficiently strong to withstand breakage due to stress from handling such as unwrapping and mouth action and also exhibit good bioadhesiveness so as to be retained in the mouth for a desired duration. Swelling of films is preferably avoided or limited, to prevent discomfort.

In certain embodiments, an oral dosage form is a sublingual dosage form.

Pharmacokinetic profiles of formulations are controlled by excipients. In certain embodiments a solid dosage formulation consists of at least one dopamine agonist (for both fast and slower absorption), a filler (preferably mannitol, lactose, xylitol and mixtures thereof) or solvent matrix, a binder (e.g., Kollidon) to one or both of two sized dopamine agonist particles, and a disintegrant.

A binder is preferably employed in a minimum quantity to prevent unnecessary reduction in the rate of dissolution for each of the "fast" and "slow" dissolution aspect of the dosage form. Preferred binders are soluble in water. Preferred binders are polyvinyl pyrolidone, hydroxymethyl polyvinyl pyrolidone, and gelatin may also be used.

The proportion of the disintegrant may be 0.1 to 75% of the granule, preferably 1 to 60%, more preferably 1 to 40%.

A minimal proportion of lubricant is preferred, for example up to 1%, preferably about 0.8%. Use of an extra-granular lubricant alone is preferred in order to minimize the hydrophobic properties of the dosage form.

Tablet may include conventional excipients typically present in an amount of about 10% of the total weight. These may include flavoring agents. Flavoring agents when used are typically present up to about 0.5 to 5% by weight of the whole tablet. Sweeteners and further excipients may also include coloring agents, preservatives and fillers.

Preferred fillers are selected from saccharides. Mannitol, lactose, xylitol and mixtures thereof are preferred on account of their solubility and despite the water content of lactose in particular. Mannitol is preferably present in an amount of 20 to 40% w/w, and more preferably present in an amount of 20 to 30% w/w. Lactose is preferably present in an amount of 30 to 60% w/w. Preferred fillers are anhydrous.

In certain transmucosal embodiments, a first active agent of particular particle size is complexed with or administered together with a second agent, e.g., an agent that facilitates penetration of the active agent into a tissue, into cells, or into the blood stream. In one embodiment, an active agent is provided together with a permeation enhancer.

Exemplary agents enhancing uptake of a active agent(s) into cells include fatty acids, derivatives of fatty acids, lipids or complexes of lipids or comprising lipids, e.g., liposomes. Liposomes are hollow spherical vesicles composed of lipids arranged in a similar fashion as those lipids which make up the cell membrane. They may have an internal aqueous space for entrapping water soluble compounds and range in size from 0.05 to several microns in diameter. For example, a liposome delivery vehicle originally designed as a research tool, Lipofectin, has been shown to deliver intact molecules to cells. Liposomes offer several advantages: they are nontoxic and biodegradable in composition; they display long circulation half-lives; and recognition molecules can be readily attached to their surface for targeting to tissues. Lipid aggregates can be formed with macromolecules using, e.g., cationic lipids alone or including other lipids and amphiphiles such as phosphatidylethanolamine. Liposomes comprising cationic lipids are favored for delivery of negatively charged molecules.

Other drug delivery vehicles that can be used include hydrogels, cyclodextrins, biodegradable polymers (surgical implants or nanocapsules), and bioadhesive microspheres.

Agents may also be provided together with a sustained release mechanism, which may include, e.g., polymer microspheres, and other mechanisms known to those skilled in the art to vary the rate of release of an agent. Accordingly, an active agent may be provided together with at least one permeation or permeability enhancer, and/or optionally, may comprise at least one sustained release mechanism and/or at least one bioadhesive. Examples of permeation enhancers include, but not limited to, fatty acids, Cavitron, thiomers, and polyoxyethylene.

Where the dosage form is a transdermal patch, dopamine agonist may be micronized or solvated and added to a dermal delivery system such as commonly used in pharmaceutical "patches" for sustained drug delivery over long periods (hours) of time.

In one embodiment, a gel composition comprising one or more dopamine agonist is applied to the skin of a person having a metabolic disease or exhibiting key elements associated therewith. Oral compositions can be applied in measured quantity as a lotion or ointment. Such compositions may be applied, e.g., to a backing layer to make a dosage form which provides a suitable adhesive means to adhere the dosage form to the subject to be treated. For example, the backing layer can be shaped around the sides of the applied gelled dopamine agonist composition and then extended horizontally. To the underside of the thus formed peripheral ring can be applied a suitable adhesive layer for adhering the dosage unit to the skin of the subject to be treated.

Skin patches may be single-layer drug in adhesive, multi-layer drug in adhesive, reservoir or matrix type patches. The single-layer drug in adhesive patch comprises an adhesive layer that also contains one or more dopamine agonist. In this type of patch the adhesive layer not only serves to adhere the various layers together, along with the entire system to the skin, but is also responsible for the releasing mechanism of the dopamine agonist(s). The adhesive layer is surrounded by a temporary liner and a backing. The multi-layer drug in adhesive patch is similar to the single-layer system in that both adhesive layers are also responsible for the releasing mechanism of the dopamine agonist(s). The multi-layer system is different however in that it adds another layer of drug-in-adhesive, usually separated by a membrane (but not in all cases). This patch may also have a temporary liner-layer and a permanent backing. The reservoir patch is unlike the single-layer and multi-layer systems in that the reservoir transdermal system has a separate drug layer comprising dopamine agonist(s) for two different delivery rates to the skin. The drug layer is a liquid compartment containing a drug solution or suspension separated by the adhesive layer. This patch may have a backing layer. The matrix patch has a drug layer of a semisolid matrix containing a dopamine agonist(s) solution or suspension. The adhesive layer in this patch surrounds the drug layer and may partially overlay it.

Transdermal patches may comprise a gelling agent, preferably saturated or highly saturated with the selected dopamine agonist or dopamine agonists. The gelling agent selected is biocompatible, compatible with the dopamine agonists, and permits the dopamine agonist to be transdermally absorbed.

Also, instead of gelling agent or in addition to a gelling agent, the homogeneous mixture including dopamine agonist can be added to an absorbent which is capable of absorbing the dopamine agonist. A suitable absorbent can be selected from an absorbent cotton, a biocompatible and suitable synthetic fibrous material including spun-bonded materials and other absorbents suggested to those skilled in the art. The final dopamine agonist composition after addition of the gelling agent or absorbent will have a suitable viscosity for use in transdermal therapy.

Where the dosage form is an aerosol formulation, it may be administered using two different vehicles for the two different solutions in one container. Such a container may have two vessels and ports each specific to the two solutions. Alternatively, the two different solutions could be combined into one container.

The term "metabolic disorder" includes disorders associated with aberrant whole-body glucose, lipid and/or protein metabolism of a species and pathological consequences arising there from. These metabolic disorders may or may not be associated with aberrant patterns in the daily levels (and fluctuations) of prolactin secretion.

The "key elements" of these metabolic disorders include but are not limited to, type 2 diabetes, prediabetes (impaired fasting glucose or impaired glucose tolerance), metabolic syndrome or indices (key elements) thereof (increased waist circumference, increased fasting plasma glucose, increased fasting plasma triglycerides, decreased fasting high density lipoprotein level, increased blood pressure), insulin resistance, hyperinsulinemia, cardiovascular disease (or key elements thereof such as arteriosclerosis, coronary artery disease, peripheral vascular disease, or cerebrovascular disease), congestive heart failure, obesity, elevated plasma norepinephrine, elevated cardiovascular-related inflammatory factors, elevated plasma factors potentiating vascular endothelial dysfunction, hyperlipoproteinemia, arteriosclerosis or atherosclerosis, hyperphagia, hyperglycemia, hyperlipidemia, and hypertension or high blood pressure, increased plasma postprandial triglyceride or free fatty acid levels, increased cellular oxidative stress or plasma indicators thereof, increased circulating hypercoagulative state, renal disease including renal failure and renal insufficiency.

The phrase "dissolution profile" as used herein, refers to the dissolution of an agent over time. The dissolution can be measured as the relative amount of agent dissolved over time, the amount of agent dissolved, or the concentration of the dissolved agent at a given time. The preferred method of determining dissolution rate is USP basket method at 100 RPM in 900 ml aqueous buffer 0.01N HCl, at 37° C. Alternative methods are equally acceptable including the USP paddle method and other suitable methods known to those of skill in the art.

As used herein, the term "pharmaceutically acceptable" refers to a biologically or pharmacologically compatible drug component for in vivo use, and preferably means a drug component approved by a regulatory agency of the Federal or a state government or listed in the U.S. Pharmacopoeia or other generally recognized pharmacopoeia for use in animals, and more particularly in humans.

The term "bioavailability" refers to the rate and extent to which a dopamine agonist is absorbed into a biological system from an administered drug product and becomes available at the site of biological action.

As used herein, a "therapeutically effective amount" refers to the amount of an active agent sufficient to treat metabolic disease and/or the key elements of metabolic disease.

Pharmacokinetic Profile & Prolactin

Healthy (normal) subjects, i.e., lean members of a species not suffering from such metabolic disease and/or key elements thereof have highly predictable daily prolactin release profiles. In humans these release profiles are characterized by a low and relatively constant prolactin level during the waking hours (day) followed by a sharp rise to a peak during sleep (night) and subsequent more gradual tapering down to the waking hours level by morning. One or more dopamine agonist can be administered to a subject in need thereof to modify aberrant daily prolactin level rhythms so that they resemble, or more closely approximate in phase and amplitude, the normal diurnal plasma prolactin level rhythms of lean, young and healthy members of the same species and sex. See e.g., U.S. Pat. Nos. 5,468,755; 5,496,803; 5,344,832, 5,585,347, 5,830,895, and 6,855,707 and PCT applications US93/12701 and US95/09061 (the disclosure of which is incorporated herein by reference). Such modulation of prolactin rhythms has been used to treat type 2 diabetes, obesity, insulin resistance, and hyperinsulinemia or hyperglycemia, hyperlipoproteinemia, hyperphagia, obesity, insulin resistance (impaired glucose tolerance), hyperlipidemia, etc.

The parenteral dosage forms of the present invention can produce a particular pharmacokinetic profile of dopamine agonist that is effective in sculpting the patients plasma prolactin profiles by reducing aberrantly elevated diurnal plasma prolactin levels to within low normal daytime levels without extending an equivalent resulting plasma prolactin level into the night-time (or sleep time hours) and thus does not result in equivalent daytime and night-time plasma prolactin levels, thus potentiating treatment of metabolic disorders and/or key elements of metabolic disorders in subjects with such prolactin secretory disorders. It must be appreciated however that "normalization" of the prolactin circadian rhythm is not necessarily a prerequisite for the dopamine agonist induced improvement in metabolism, in and of itself, but rather such "normalization" activity can function to potentiate dopamine agonist induced improvements in metabolic disease and key elements thereof.

The parenteral dosage forms of the present invention can also produce a particular pharmacokinetic profile that is effective in reducing levels of elevated plasma norepinephrine concentration without the dopamine agonist having to be present in the circulation throughout the day. Such influences of the parenteral dosage forms, while not a prerequisite for their activity on metabolic disease, potentiate improvements in metabolic disease and key elements thereof.

Formulations desirably have a pharmacokinetic profile that enhances efficacy of an active agent.

Pharmacokinetic profiles are indicative of the absorption and disposition of active agent(s) and may be defined by plasma concentration data used to assess key pharmacokinetic parameters such as, for example, $T_{max}$, $C_{max}$, AUC, and $t_{lag}$. $T_{max}$ is the time to peak concentration. $C_{max}$ is the peak concentration. AUC is the area under the curve (AUC). $t_{lag}$ is the absorption lag time.

The process of absorption can be seen as increasing the amount of a compound or dose x introduced into a system. Absorption studies seek to define the rate of input, dx/dt, of the dose x. For example, a constant rate infusion, R, of a drug might be 1 mg/hr, while the integral over time of dx/dt is referred to as the extent of drug input, x(t), i.e., the total amount of drug x administered up to that particular time t. Complex absorption profiles can be created by the use of controlled, extended, delayed or timed release of drugs from a dosage form.

Disposition is further subdivided into the study of the absorption, distribution, metabolism and elimination or excretion of a drug, collectively referred to as ADME.

The processes of disposition can be seen as the clearing, or disposing of drug. Generally, the disposition process distributes the drug within the system, converts or metabolizes the drug, and eliminates the drug or metabolites of the drug by passing them via the urine, feces, sweat, exhalation or other routes of elimination.

In one embodiment, the parenteral dosage forms of the present invention provide for the maintenance of a nocturnal rise in plasma prolactin level (a neuroendocrine physiological event) in obese/insulin resistant or type 2 diabetic subjects.

The ADME criteria influence the levels and kinetics of drug exposure to the tissues and hence influence the performance and pharmacological activity of a drug. Before an active agent can exert a pharmacological effect in tissues, it has to be absorbed into the bloodstream. The active agent must then be distributed to its effector site(s), most often via the bloodstream. Active agents begin to be metabolized as soon as they enter the body. Compounds and their metabolites need to be excreted from the body via excretion, usually through the kidneys (urine) or in the feces. Unless excretion is complete, accumulation of foreign substances can adversely affect normal metabolism.

In one embodiment, a dosage form exhibits a pharmacokinetic profile with a $T_{max}$ about 1 to about 90 minutes or about 5 to about 90 minutes after administration, a plasma drug concentration of at least 50% $C_{max}$ for a duration of about 90 to about 360 minutes, and a decrease in plasma level that may approximate first order elimination kinetics.

In another embodiment, a dosage form exhibits a pharmacokinetic profile with a $T_{max}$ about 1 to about 90 minutes or about 5 to about 90 minutes after administration, a plasma drug concentration of at least 50% $C_{max}$ for a duration of about 180 to about 360 minutes, and a decrease in plasma level that may approximate first order elimination kinetics.

In a another embodiment, a dosage form exhibits a pharmacokinetic profile with a $T_{max}$ about 1 to about 90 minutes or about 5 to about 90 minutes after administration, a plasma drug concentration of about 70 to 100% $C_{max}$ for a duration of about 90 to about 360 minutes, and a decrease in plasma level that may approximate first order elimination kinetics.

In a preferred embodiment, a dosage form exhibits a pharmacokinetic profile with a $T_{max}$ about 1 to about 90 minutes or about 5 to about 90 minutes after administration, a plasma drug concentration of at least 70 to 100% $C_{max}$ for a duration of about 180 to about 360 minutes, and a decrease in plasma level that may approximate first order elimination kinetics.

In another embodiment, a dosage form exhibits a pharmacokinetic profile with a $T_{max}$ about 1 to about 90 minutes or about 5 to about 90 minutes after administration, a post $C_{max}$ level of about 35-65% of $C_{max}$ within about 30-150 minutes after $T_{max}$, followed by a post $C_{max}$ level of about one-half $C_{max}$ for about 60 to 420 minutes, followed by a decrease in plasma level that may approximate first order elimination kinetics.

Preferably, a pharmacokinetic profile has a $T_{max}$ about 15 to about 90 minutes after administration, a post $C_{max}$ level of about 35-65% of $C_{max}$ within about 30-90 minutes after $T_{max}$, followed by a post $C_{max}$ level of about one-half $C_{max}$ for about 60 to 360 minutes, followed by a decrease in plasma level that may approximate first order elimination kinetics.

In another embodiment, a dosage form exhibits a pharmacokinetic profile having a plasma $T_{max}$ about 15 to about 60 minutes after administration, a post $C_{max}$ level of about one-half $C_{max}$ within about 30 to about 150 minutes of $T_{max}$ followed by a post $C_{max}$ level of about one-half $C_{max}$ for a duration of about 90 to about 360 minutes, followed by a decrease in plasma level that may approximate first order elimination kinetics.

In yet another embodiment, a dosage form exhibits a pharmacokinetic profile with a plasma $T_{max}$ about 10 to about 60 minutes after administration, a post $C_{max}$ level of about one-half $C_{max}$ within about 30 to about 150 minutes of $T_{max}$, a post $C_{max}$ level of about one-half $C_{max}$ for a duration of about 90 to about 240 minutes, and a decrease in plasma level that may approximate first order elimination kinetics.

In one embodiment, a dosage form exhibits a pharmacokinetic profile with a plasma $T_{max}$ about 5 to about 60 minutes after administration, a plasma $T_{max}$ 10 to 60 minutes after administration, a plasma $T_{max}$ 10 to 90 minutes after administration, a plasma $T_{max}$ 15 to 90 minutes after administration, or a plasma $T_{max}$ 15 to 60 minutes after administration.

In one embodiment, a dosage form exhibits a pharmacokinetic profile with 90% of the active agent cleared from plasma within about 240 to about 480 minutes from the end of the post $C_{max}$ level.

In one embodiment, a dosage form exhibits a pharmacokinetic profile with substantially all of the active agent cleared from plasma within about 5 hours following the end of the plasma plateau.

In one embodiment, a dosage form exhibits a pharmacokinetic profile wherein the post-$C_{max}$ plateau is sustained for about 2 to about 8 hours.

In one embodiment, more than about 10% of the total active agent of a dosage form is absorbed into the plasma. In another embodiment, more than about 35% of the total active agent of a dosage form is absorbed into the plasma.

In one embodiment, a permeability enhancer is combined in one portion of the dosage form with a sustained release mechanism in another portion of the dosage form to allow for the quick peak followed by the sustained "tail" of the pharmacokinetic profile of the formulation.

The above described pharmacokinetic profiles allow for a peak of dopamine agonist into the circulation that can be used to impact a circadian neuro-oscillator system (e.g., suprachiasmatic nucleus) in the brain to positively influence its regulation of metabolism via output control over other metabolism regulatory centers in the brain to thereby improve peripheral metabolism immediately followed by a sustained lower level of release of dopamine agonist into the circulation for a determined period of time that can directly influence other metabolism regulatory centers in the brain to improve metabolism.

Some of the above described pharmacokinetic profiles allow for a pulsed peak of dopamine agonist into the circulation that can be used to impact a circadian neuro-oscillator system (e.g., suprachiasmatic nucleus) in the brain followed by a sustained lower level of release of dopamine agonist into the circulation for a determined period of time.

When used at the appropriate dosages and pre-determined times of day in an individual with metabolic disease, the above described pharmacokinetic profiles can mimic the natural daily pattern of brain dopamine in metabolic control centers within the brain of a healthy normal individual of the same species and thereby improve metabolic disease.

Figure 2:
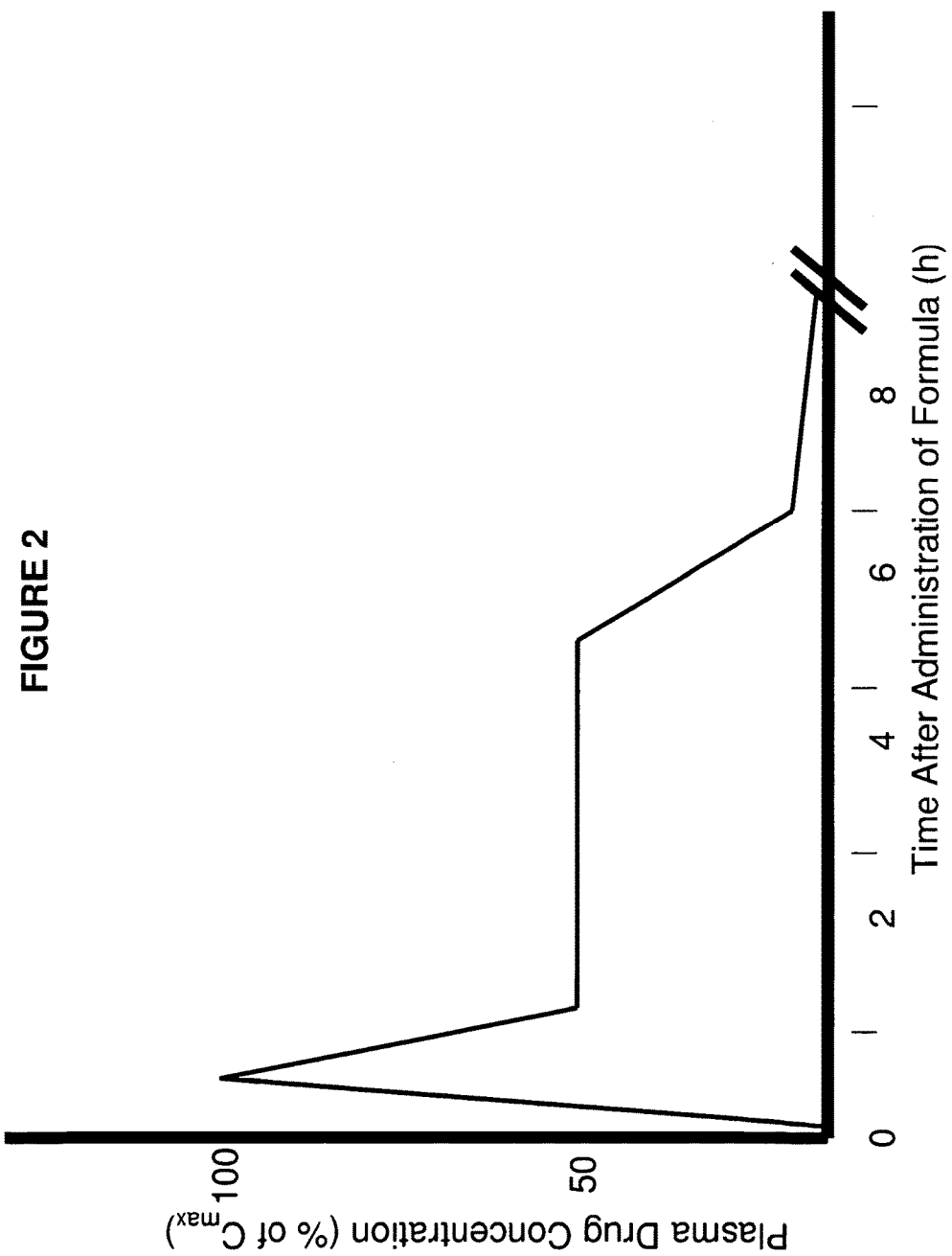
FIG. 2 is a graph showing another pharmacokinetic profile of a parenteral dosage formulation according to the present invention for administering a dopamine agonist.
Figure 3:
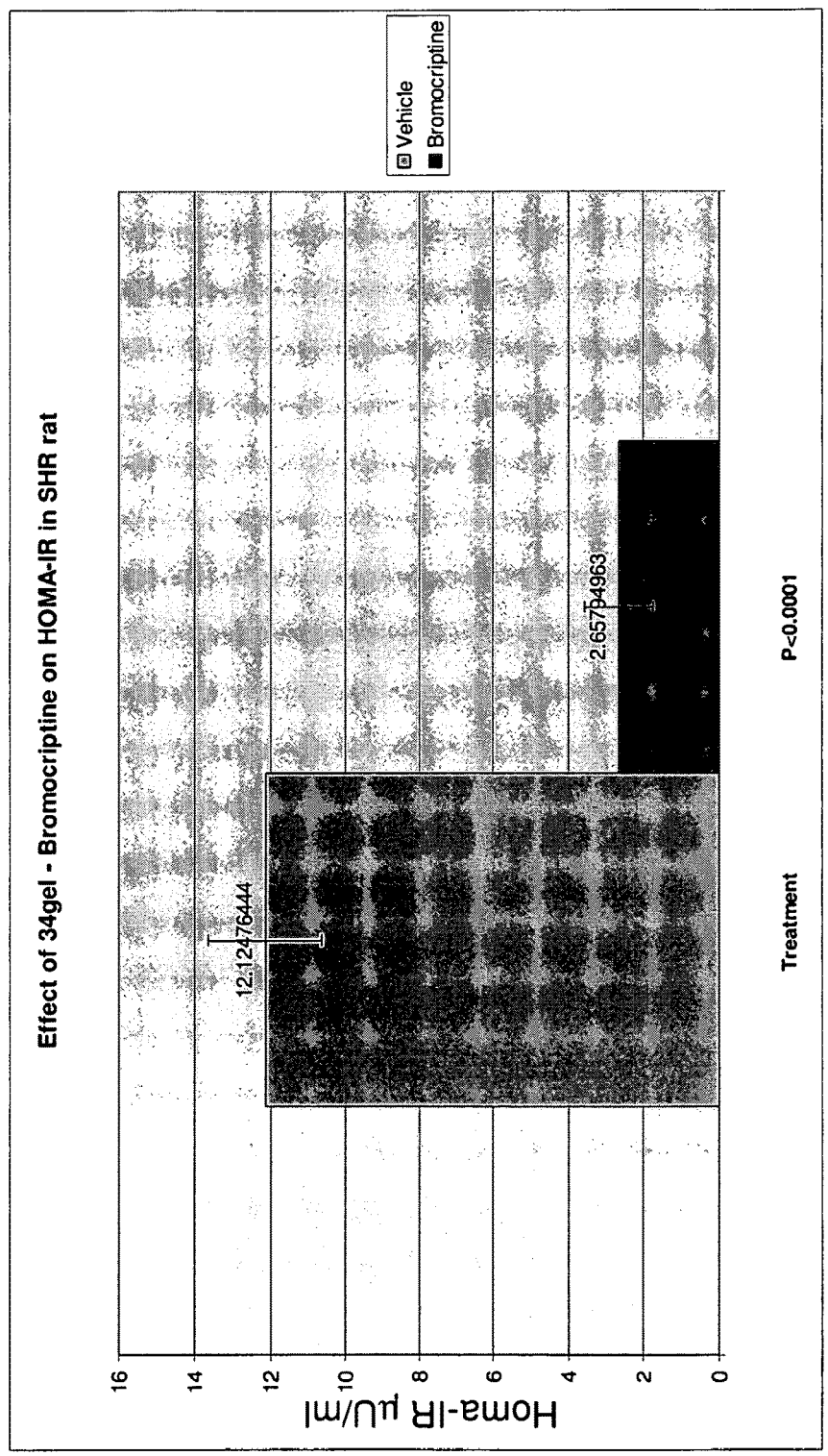
FIG. 3 is a graph showing the effect of 7 day parenteral treatment with the 34 Gel formulation (10 mg/kg) on insulin resistance (HOMA-IR) in the SHR rat model.
Figure 4:
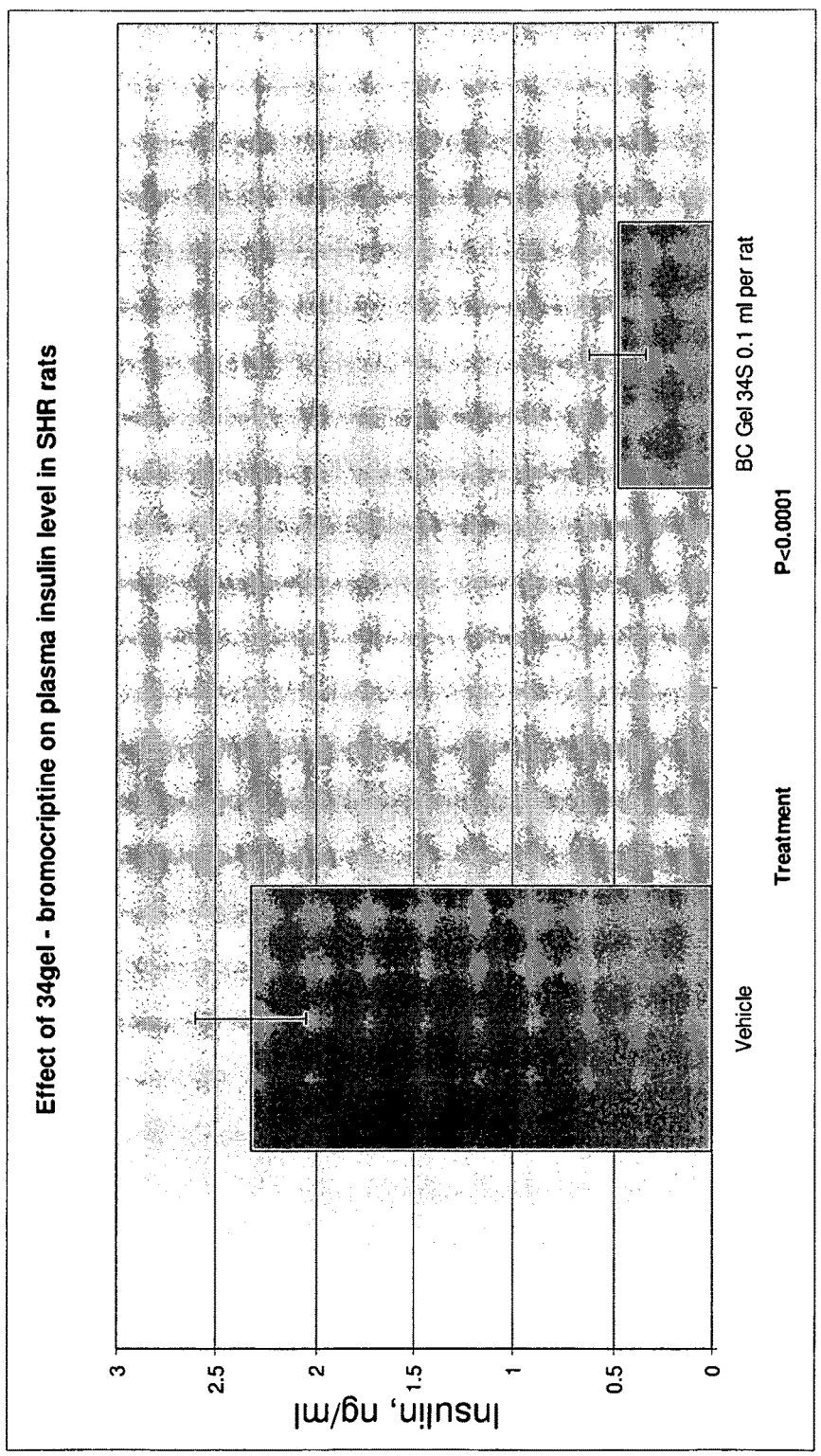
FIG. 4 is a graph showing the effect of 7 day parenteral treatment with the 34 Gel formulation (10 mg/kg) on plasma insulin levels in the SHR rat model.
Figure 5:
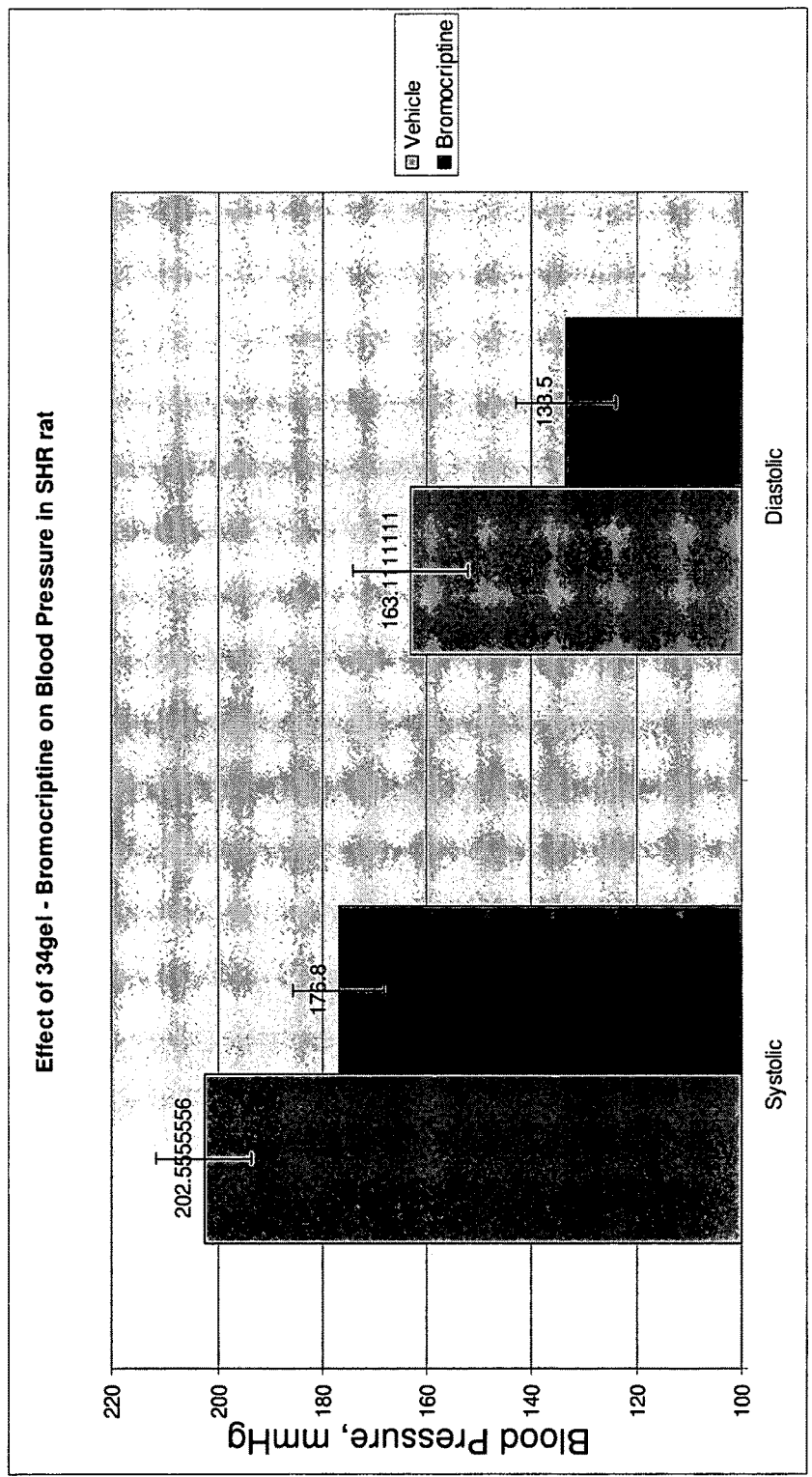
FIG. 5 is a graph showing the effect of 7 day parenteral treatment with the 34 Gel formulation (10 mg/kg) on blood pressure in the SHR rat model.

Thus, a dosage form according to the present invention may exhibit a pharmacokinetic profile having a plasma $T_{max}$ followed by a post $C_{max}$ level of at least that is 70 to 100% for a sustained period of time prior a decrease in plasma level that may approximate first order elimination kinetics. See e.g., FIG. 1. Alternatively, a dosage form according to the present invention may exhibit a pharmacokinetic profile having a plasma $T_{max}$, followed by a post $C_{max}$ level that decreases over time to about one-half $C_{max}$, a decreased level and that is then sustained for a period of time prior to a decrease in plasma level that may approximate first order elimination kinetics. See e.g., FIG. 2.

When one or more dopamine agonist is administered with a peripheral acting agent, the one or more dopamine agonist and the peripheral acting agent may, have the same pharmacokinetic profile or substantially similar or similar pharmacokinetic profiles, e.g., any of the pharmacokinetic profiles set forth above. Alternatively, when one or more dopamine agonist is administered with a peripheral acting agent, the one or more dopamine agonist and the peripheral acting agent may, have different pharmacokinetic profiles. In certain embodiments, for example, the one or more dopamine agonist has a pharmacokinetic profile set forth above and a peripheral acting agent has a pharmacokinetic profile having a $T_{max}$ between 0-90 min with a plasma level concentration of greater than or equal to about 25% of $C_{max}$ from the time of $T_{max}$ through 12 hours post $T_{max}$.

The particular pharmacokinetic profile produced by a dosage form according to the present invention will vary, in part, based on the amount of active agent included in the dosage formulation.

In certain embodiments, a dosage form includes bromocriptine as the active agent and exhibits one of the foregoing pharmacokinetic profiles, more preferably with a $C_{max}$ of 25-400 pg/ml.

Moreover, it will be appreciated by those skilled in the art that the desired in vitro dissolution rate, and/or the in vivo plasma concentration of dopamine agonists over time, may be obtained by selecting one or more forms of dopamine agonist, i.e., selecting one or more salt forms, crystalline forms (including one or more polymorphic forms) or amorphous forms for use in the immediate or controlled release compositions of the present invention.

Administration

The amount of the dopamine agonist(s) to be administered to a patient may vary depending for example on the weight of the patient, and the nature or severity of the metabolic disease or the key elements thereof. An effective amount of the dopamine agonist(s) may be administered in one or more dosage forms, either simultaneously or at different times, and a dopamine agonist may be administered either separately or in conjunction with other dopamine agonist(s).

Preferably, the dosage forms may be administered in a single daily dose of about 0.01 to about 50.0 mg of active agent. The preferred range is 0.02 to 50 mg of active agent, the more preferred range is 0.02 to 25 mg of active agent and the most preferred range is 0.1 to 25 mg of active agent.

Conjoined administration of one or more dopamine $D_1$ agonist with one or more $D_2$ agonist results in synergistic effects in improvement of one or more metabolic indices related to glucose or lipid metabolism, and thus an improved modification or regulation of at least one of glucose and lipid metabolism.

The administration of the $D_2$ agonist is preferably timed. The $D_2$ agonist can be administered at a pre-determined time.

The administration of the $D_1$ agonist is preferably timed. The $D_1$ agonist is administered at a pre-determined time. Because the $D_1$ agonist amplifies the effect of the conjoined $D_2$ agonist, it is advantageous to administer the $D_1$ agonist at or about the time of administration of the conjoined $D_2$ agonist(s), such that the activity period of the $D_1$ agonist in the bloodstream of the treated subject overlaps (in fact preferably overlaps as much as possible) with the activity period of the conjoined $D_2$ agonist(s). The duration of the post-$T_{max}$ plasma plateau level of the D1 agonist may persist for a period of time longer than that of the D2 agonist. For convenience of administration and in order to promote subject compliance, the $D_1$ agonist can be administered at the same time as the conjoined $D_2$ agonist(s).

Preferably, the dosage form(s) are administered once daily. More preferably, the dosage form(s) are administered once daily in the morning. Most preferably, the dosage form(s) are administered once daily at a pre-determined time for bioavailability in the morning at a point after the peak in plasma prolactin level.

Dosage forms are preferably administered in the morning from about 0400 to about 1200 hours. More preferably, the dosage forms are administered in the morning from about 0500 to about 1200 hour. Most preferably, the dosage forms are administered in the morning from about 0500 to about 1000 hour.

For treating vertebrates, dosages of dopamine agonists are typically administered over a period ranging from about 10 days to about 180 days, or longer (e.g., greater than or equal to 1 year). However, patients, e.g., patients in particularly poor physical condition, or those of advanced age, may require longer, or even continuous, treatment. A treatment duration exceeding six months or even continuous treatment may be desirable, even when not required.

Administration of $D_1$ and $D_2$ agonists typically lead to improvement of at least one condition or indices indicative of a metabolic disorder. Thus, in some embodiments administration of $D_1$ and $D_2$ agonist lead to a reduction of one or more of a metabolic disorder and/or key elements thereof such as body fat deposits, body weight, plasma or blood glucose, circulating insulin, plasma triglycerides (TG), plasma free fatty acids (FFA), cardiometabolic risk factors such as cardiovascular-related inflammatory factors, potentiators of vascular endothelial dysfunction, and hypercoagulative substances including but not limited to PAI-1 or fibrinogen, blood clotting rate or potential, neuroendocrine factors potentiating insulin resistance, blood pressure, renal dysfunction and/or insufficiency, and food consumption.

In other embodiments, the parenteral dosage forms of the present invention provide for one or more of the following metabolic physiological events in metabolic syndrome, obese, obese/insulin resistant, prediabetic, or type 2 diabetic subjects: (1) improvement of hyperglycemia, hypertriglyceridemia, impaired fasting glucose, glucose intolerance, or insulin resistance; (2) improvement in hypertension; (3) reduction of physiological indices of cardiovascular inflammation, endothelial dysfunction, hypercoagulation or blood clotting; and/or (4) reduction of body fat stores or body weight or both (5) improvement of renal function or (6) improvement of cardiac function.

In a certain embodiment, the parenteral dosage forms allow for a nocturnal (0200-0600 hour) increase in plasma prolactin of at least 35% greater than the average diurnal (0700-1900 hour) circulating level of the hormone following early morning administration of such dopamine agonist pharmaceutical preparation measured at least 6 months after the initiation of such treatment.

In a certain embodiment, the elevated (at least 15% greater than average for a normal healthy individual of the same age and sex) plasma norepinephrine levels are reduced by at least 10% by such treatment. In one embodiment, elevated plasma norepinephrine levels are reduced by at least 15%.

In a certain embodiment, nocturnal plasma prolactin levels are at least 35% greater than the average diurnal circulating level of prolactin following such dopamine agonist treatment when measured at 6 months from the initiation of the treatment.

In a certain embodiment, the parenteral dosage forms do not produce untoward GI effects, e.g., nausea, vomiting, abdominal pain, constipation, and/or diarrhea, in more than 15% of the treated population.

In a certain embodiment, the dosage form includes bromocriptine and other ergot derivatives and produces a circulating concentration of metabolites that is no greater than about 50% of that metabolite concentration produced by an oral dose of bromocriptine (or other ergot derivatives) that produces the same circulating level of bromocriptine (or other ergot derivatives).

Preparation of Dosage Forms

Water and light can accelerate the degradation of ergot-type compounds by photooxidation, photoreduction, redox reactions involving water (e.g., breakdown of bromocriptine into bromocriptinine upon excessive water or humidity exposure). Thus, the preparation of stable parenteral dosage forms comprising ergot-related dopamine agonists should be conducted to minimize exposure to light and absorption of water.

Where the production of the dosage forms of the invention which can be administered parenterally has not taken place under aseptic conditions, a final sterilization can be carried out by conventional methods known to the skilled worker, for example by autoclaving or sterile filtering. The suspensions of the invention which can be administered parenterally have preferably been produced under aseptic conditions.

Other formulation techniques may be performed using techniques well known in the art. The following examples of such techniques are illustrative and are not intended to be limiting.

Magnesium stearate and stearic acid should be added last to formulations and blended for 2 min. Magnesium should be avoided for the preparation of ergot-related dopamine agonist formulations inasmuch as magnesium greatly decreases their stability.

Particular dosage forms may be prepared using procedures well known in the art. The following are non-limiting guidelines for preparing certain types of dosage forms:

Injectable or Liquid Dosage Form

A dopamine agonist is dissolved in non-aqueous solvent or is in colloidal suspension of small aggregate size in vessel one and dopamine agonist in colloidal suspension of larger aggregate size than in vessel one (including but not necessarily limited to micronized dopamine agonist) in liquid carrier in vessel two at a total amount of 0.02 to 50.0 mg.

Vessel one may contain varying amounts of non-aqueous solvent such as ethanol, isopropanol, or propanol at 10 to 50 µl. To this solution a small volume (about 25% of solution volume) of anhydrous mucosal tissue irritant-reducing agent such as plant oils like but not limited to olive oil, corn oil or mineral oil is added.

Optionally, the solution in vessel one is then combined with anhydrous permeabilizing agents, bioadhesives, polymers, and/or stabilizers (e.g., antioxidants such as citric acid, or ascorbic acid) to give a final volume of solution of not greater than 100 µl.

Vessel two may contain either aqueous or non-aqueous solvent such as ethanol, isopropanol, or propanol at 10 to 50 µl.

To this solution a small volume (about 25% of solution volume) of anhydrous mucosal tissue irritant-reducing agent such as plant oils like but not limited to olive oil, corn oil or mineral oil is added.

Optionally, the solution in vessel two is then combined with anhydrous permeabilizing agents, bioadhesives, polymers, and/or stabilizers (e.g., antioxidants such as citric acid, or ascorbic acid) to give a final volume of solution of not greater than 100 µl.

Aerosol Dosage Form

Aerosol dosage forms may generally be prepared by adding an inert gas (e.g., nitrogen) to a liquid dosage form.

Aerosol Dosage Form

A dopamine agonist is solubilized in non-aqueous solvent such as anhydrous ethanol in a low humidity environment optionally combined with a mucosal tissue irritant-reducing agent and then placed in one chamber of a metal or hard plastic canister that is pressurized with an inert gas such as nitrogen. The canister is equipped with a mechanism for metered dosing in an aerosol spray form or the like in the range of 5 to 100 µl per dose. Optionally, after solubilization in ethanol as above, permeabilizing agents (such as bile salts, surfactants, fatty acids and derivatives, chelators, cyclodextrins, chitosan, lower alcohols), bioadhesives (such as Carbopol 934P, Carbopol 974P, 1Voveou AA-1, polyvinylpyrrolidone), and/or stabilizers such as polyethylene glycol known in the art to facilitate mucosal delivery of dopamine agonist to the systemic circulation through the mucosal site of administration are added to the dopamine agonist solution. Additionally, a quantity of anhydrous polymer such as polyethylene glycol to improve solubility of the solute components and reduce the ethanol concentration is added to the dopamine agonist-ethanol solution.

In a second separate chamber of the same canister, the dopamine agonist is micronized and added to an appropriate solvent vehicle such as polyethylene glycol to form a colloidal suspension. To such colloidal suspension permeabilizing agents, bioadhesives, and/or stabilizers known in the art that either are soluble in the vehicle or form a colloidal suspension as well are added. Such dopamine agonist suspension is placed in a metal or hard plastic canister for spray administration under inert gas pressurization.

Aerosol Dosage Form

Dopamine agonist is added to solvent at a concentration of 0.1 to 5.0 mg per approximately 10-50 μl of either an aqueous or non-aqueous solvent such as ethanol. To the solution is added a small volume (25% of solution volume) of mucosal tissue irritant-reducing agent such as olive oil or mineral oil. Optionally, mucosal uptake enhancers such as free fatty acid, and/or bioadhesives such as polyvinylpyrrolidone are added to this mixture. The solution is mixed until the dopamine agonist is fully dissolved and then the solution is placed into a light impenetrable device that is pressurized under inert gas such as nitrogen and equipped with a mechanism for metered delivery of 10 to 100 μl spray per dosing to provide a dose of 0.1 to 5.0 mg dopamine agonist.

In a second separate chamber of the same device, dopamine agonist is added to either an aqueous or non-aqueous solvent, such as anhydrous ethanol in a low humidity environment at a concentration of 0.1 to 50.0 mg per approximately 5-25 μl of ethanol. Upon full dissolution of the dopamine agonist into the solvent a polymer such as polyethylene glycol, or long chain fatty acids or plant oil such as olive oil, corn oil, or mineral oil is added to produce an approximate 70/30 solution of ethanol/other agent to adjust the absorption rate of dopamine agonist of this preparation to be different from (slower than) that of the preparation of the other chamber of the canister. To the solution, is added a small volume (25% of solution volume) of mucosal tissue irritant-reducing agent such as olive oil or mineral oil. To this solution are added mucosal uptake enhancers such as free fatty acid, and/or bioadhesives such as polyvinylpyrrolidone. The solution is mixed until the dopamine agonist is fully dissolved or prepared as a colloidal suspension and then the solution is placed into a light impenetrable device that is pressurized under inert gas such as nitrogen and equipped with a mechanism for metered delivery of 10 to 50 μl spray per dosing to provide a dose of 0.1 to 50.0 mg dopamine agonist.

Aerosol or Liquid Dosage Form

Dopamine agonist is micronized to a diameter of between 0.1 and 1.0 μm and then added to a polymer such as polyethylene glycol or to fatty acid, or to a plant oil such as mineral oil or the like to form a colloidal suspension of 0.1 to 5.0 mg of dopamine agonist per 10-50 μl of vehicle. To the suspension a small volume (25% of suspension volume) of mucosal tissue irritant-reducing agent such as olive oil or mineral oil is added. To this suspension mucosal uptake enhancers such as free fatty acid, and/or bioadhesives such as polyvinylpyrrolidone is added. The suspension is placed into a light impenetrable device that is pressurized under inert gas such as nitrogen and equipped with a mechanism for metered delivery of 10 to 100 μl spray per dosing to provide a dose of 0.1 to 5.0 mg dopamine agonist.

In a second separate chamber of the same device, dopamine agonist is added to either an aqueous or non-aqueous solvent such as anhydrous ethanol in a low humidity environment at a concentration of 0.1 to 50.0 mg per approximately 5-25 μl of ethanol. Upon full dissolution of the dopamine agonist into the solvent a polymer such as polyethylene glycol, or long chain fatty acids or plant oil such as olive oil, corn oil, or mineral oil is added to produce an approximate 70/30 solution of ethanol/other agent to adjust the absorption rate of dopamine agonist of this preparation to be different from (slower than) that of the preparation of the other chamber of the canister. To the solution, is added a small volume (25% of solution volume) of mucosal tissue irritant-reducing agent such as olive oil or mineral oil. To this solution are added mucosal uptake enhancers such as free fatty acid, and/or bioadhesives such as polyvinylpyrrolidone. The solution is mixed until the dopamine agonist is fully dissolved or prepared as a colloidal suspension and then the solution is placed into a light impenetrable device that is or is not pressurized under inert gas such as nitrogen and equipped with a mechanism for metered delivery of 10 to 100 μl spray per dosing to provide a dose of 0.1 to 50.0 mg dopamine agonist.

Solid Dosage Form

A solid stable parenteral dosage form of the present invention is prepared that includes: (1) a dopamine agonist having from 0.02 to 50.0 mg of small particle size, and having a relatively larger particle size for slower dissolution and absorption; mixed with an antioxidant such as citric acid (2); the mixture is combined with a carrier such as mannitol and then combined with a disintegrant and bioadhesive such as Benecal or Kollidon CL and an anhydrous polymer as binder such as cellulose or cellulose analogs, polyethyleneglycol, fatty acid, or plant oil; (3) optionally, a small amount of anhydrous mucosal tissue irritant-reducing agent such as olive oil or mineral oil; and (4) optionally, additional anhydrous permeabilizing agents, bioadhesives, and/or stabilizers are added followed by a lubricant such as stearate or castor oil to give a final weight of not greater than 200 mg to produce a rapid dissolving solid dosage form with rapid and slower sustained absorption of dopamine agonist wherein final dosage is between 0.02 and 50.0 mg. These ingredients are preferably added to the mixture in this order.

Solid Dosage Form

A solid stable parenteral dosage form of the present invention is prepared that includes: (1) micronized dopamine agonist of diameter (a) 0.1 to 5.0 μm and (b) 10-200 μm at 0.02 to 50.0 mg total; mixed with an antioxidant such as citric acid (2); the mixture is combined with a carrier such as mannitol and then combined with a disintegrant and bioadhesive such as Kollidon CL and an anhydrous polymer as binder such as cellulose or cellulose analogs, polyethyleneglycol, fatty acid, or plant oil; (3) optionally, a small amount of anhydrous mucosal tissue irritant-reducing agent such as olive oil or mineral oil; and (4) optionally, additional anhydrous permeabilizing agents, bioadhesives, and/or stabilizers are added followed by a lubricant such as stearate or castor oil to give a final weight of not greater than 250 mg to produce a rapid dissolving solid dosage form with rapid and slower sustained absorption of dopamine agonist wherein final dosage is between 0.02 and 50.0 mg. These ingredients are preferably added to the mixture in this order.

Solid Dosage Form

Dopamine agonist is added to either an aqueous or anhydrous solvent such as ethanol in a low humidity environment at a concentration of 0.1 to 50.0 mg per approximately 50-250 µl of solvent. Upon full dissolution of the dopamine agonist into the solvent a polymer such as polyethylene glycol or a fatty acid or a plant oil is added to produce an approximate 70/30 solution of solvent/other agent. To the solution is added a small volume (25% of solvent volume) of mucosal tissue irritant-reducing agent such as olive oil or mineral oil. To this solution are added mucosal uptake enhancers such as free fatty acid, and/or bioadhesives such as polyvinylpyrrolidone. The dopamine agonist-solution may then be combined with a binder or matrix such as plant gum, gelatin, polyvinylpyrrolidone, magnesium stearate, or castor oil providing for rapid dissolution, dried and then formed into one side of a solid dosage form at 0.1 to 50.0 mg per dosage for mucosal delivery.

A second portion of the solid dosage form is comprised of (1) micronized dopamine agonist of diameter 0.1 to 5.0 µm or small particle size dopamine agonist of 10-200 um at 0.02 to 50.0 mg total; mixed with an antioxidant such as citric acid; (2) the mixture is combined with a carrier such as mannitol and then combined with a disintegrant and bioadhesive such as Kollidon CL and an anhydrous polymer as binder such as cellulose or cellulose analogs, polyethyleneglycol, fatty acid, or plant oil; (3) optionally, a small amount of anhydrous mucosal tissue irritant-reducing agent such as olive oil or mineral oil; and (4) optionally, additional anhydrous permeabilizing agents, bioadhesives, and/or stabilizers are added followed by a liquid matrixing agent such as polyvinylpyrrolidone, gelatin, or plant gum that is dried to give a final weight of not greater than 250 mg to produce a rapid dissolving solid dosage form with rapid and slower sustained absorption of dopamine agonist wherein the final dosage is between 0.02 and 50.0 mg. These ingredients are preferably added to the mixture in this order. The two sections of the dosage form are annealed and packaged into an aluminum foil wrap to prevent moisture from entry. Alternatively the two sections are combined, one inside of the other for delivery that effectuates a fast absorption and a slower more sustained absorption.

Solid Dosage Form

Dopamine agonist is micronized to a diameter of between 0.1 and 1.0 µm and then added to an anhydrous polymer such as polyethylene glycol or to fatty acid or to a plant oil to form a colloidal suspension of 0.1 to 1.0 mg of dopamine agonist per 10-25 µl of vehicle. To the suspension is added a small volume (25% of suspension volume) of mucosal tissue irritant-reducing agent such as olive oil or mineral oil. To this suspension are added mucosal uptake enhancers such, as free fatty acid, and/or bioadhesives such as polyvinylpyrrolidone. The dopamine agonist suspension is then combined with a binder or matrix such as plant gum, gelatin, mannitol, polyvinylpyrrolidone, or stearate. The dopamine agonist-colloidal suspension may then be combined with a binder or matrix such as plant gum, gelatin, polyvinylpyrrolidone, stearate, or castor oil providing for rapid dissolution, dried and then formed into one side of a solid dosage form at 0.1 to 50.0 mg per dosage for mucosal delivery.

A second portion of the solid dosage form is comprised of (1) small particle size dopamine agonist of 10-200 µm at 0.02 to 50.0 mg total mixed with an antioxidant such as citric acid; (2) the mixture is combined with a carrier such as mannitol and then combined with a disintegrant and bioadhesive such as Kollidon CL and an anhydrous polymer as binder such as cellulose or cellulose analogs, polyethyleneglycol, fatty acid, or plant oil; (3) optionally, a small amount of anhydrous mucosal tissue irritant-reducing agent such as olive oil or mineral oil; and (4) optionally, additional anhydrous permeabilizing agents, bioadhesives, and/or stabilizers are added followed by a liquid matrixing agent such as polyvinylpyrrolidone, gelatin, or plant gum that is dried to give a final weight of not greater than 250 mg to produce a rapid dissolving solid dosage form with rapid and slower sustained absorption of dopamine agonist wherein the final dosage is between 0.02 and 50.0 mg. These ingredients are preferably added to the mixture in this order. The two sections of the dosage form are annealed and packaged into an aluminum foil wrap to prevent moisture from entry. Alternatively the two sections may be combined, one inside of the other for delivery that effectuates a fast absorption and a slower more sustained absorption.

Transdermal Patch Dosage Form

A solid stable parenteral dosage form of the present invention is prepared that includes: (1) dopamine agonist of dissolved state, single or two different particle sizes at 0.02 to 5.0 µm; (2) nontoxic organic solvent such as ethanol, isopropanol, propanol at 5 to 100 µA and (3) optionally, anhydrous permeabilizing agent such as polyethyleneglycol or fatty acid, or plant oil is added.

The above formulation is then added to a transcutaneous drug delivery system.

The transcutaneous drug delivery system comprises: (1) a rate controlling matrix membrane, of polyethylene, polyurethane, PVC, polyacrylates, polycarbonates, polyvinyls, polystyrenes, polyamides, and derivatives thereof, cellulose, cellulose derivatives, and combinations of the above, the thickness and porosity of which can be adjusted to adjust the diffusion rate of drug from the reservoir; and (2) an adhesive for adhering such drug matrix to the skin such that such adhesive does not physically block the release of drug from the delivery system into the skin; (3) a backing impenetrable to light, moisture, humidity, and the contents of the delivery system; and (4) a removable front impenetrable to light, moisture, humidity, and the contents of the delivery system. The delivery system is further characterized by the ability to have a slow and faster delivery rate to and through the cutaneous tissue for a respectively slow and faster absorption rate in to the body.

Transepithelial Combination Formulation of Dopamine Agonist Plus Peripheral Acting Agent Peripheral acting agents can be added to the slow release component of dopamine agonist formulations. The peripheral acting agent then is released slowly from the formulation to provide a sustained release over an approximate 4-12 hour period of time from administration. In some cases where it may be desirable, the peripheral acting agent may also be added to the fast release component of the dopamine agonist formulation to effectuate a fast release of peripheral acting agent. In still other cases, the peripheral acting agent may be added to both the slow and fast release components of the dopamine agonist formulation to produce a rapid rise in the plasma followed by a sustained peak or near-peak levels for an approximate 4-12 hour period.

The examples listed below demonstrate that manipulations to the components of parenteral dopamine agonist formulations can be made that produce predictable changes in the profile of the peak-plateau bioavailability curve and when administered parenterally exhibit the desired peak-plateau bioavailability curves in vivo. Appropriately timed daily parenteral administration of dopamine agonist formulations, which exhibit the desired peak-plateau bioavailability curve, reduce metabolic disorders in well established animal models of metabolic disease (see Examples 18-21 and FIGS. 3-8). Furthermore, these parenteral formulations of dopamine agonists can be made to be stable to heat and humidity under standard sample bottling conditions (see Example 22).

Several excipients may have an effect on the dissolution profile of the active agent. For example, as the excipients of ProSolv (microcellulose filler) and Benecel (bioadhesive/active agonist release matrix) increase in concentration, they act to slow the dissolution rate of the active agent. Contrariwise, the excipients of citric acid and Pharmaburst accelerate the early and overall dissolution rate of the dopamine agonist, respectively. When additional citric acid is added and the Benecel levels are reduced, the overall dissolution rate of the dopamine agonist maintains the desired early fast dissolution profile followed by a slower constant dissolution. If the citric acid level is further increased (as seen with formulation 11S tablet described below), then surprisingly, the early burst-release of the formulation is markedly enhanced with about 40% released within the first 30 minutes followed by a slower but constant release for the next 210 minutes. Cyclodextrin can be added to improve this release profile while enhancing the absorption characteristics of the formulation, as seen in formulation 12S below.

If one switches the Explotab disintegrant for Pharmaburst, the disintegration time is also accelerated (from about 15 to 5 minutes). This accelerated disintegration is a desirable characteristic for parenteral tablet administration. Also, use of Pharmaburst accelerates the overall dissolution profile of the formulation. Moreover, it can be appreciated that by altering the ratio of Explotab versus Pharmaburst as well as adjusting the Benecel and ProSolv levels in the tablet, an intermediate release profile of dopamine agonist can be achieved. Such hybrid formulations allow for "fine-tuning" of the desired formulation of dopamine agonist to produce the desired PK profile. Adding Efffersoda to Pharmaburst further accelerates the disintegration and dissolution times of the dopamine agonist formulation.

Further Bioadhesive levels can be adjusted in these parenteral formulations to a maximum level of bioadhesive to support the bioadhesion of the active agent while still allowing for a quick burst dissolution of active agent. Increasing the level of bioadhesive results in a slowing of active agent dissolution time, however, reducing bioadhesive levels has no effect on dissolution time. Therefore, the relative amounts of bioadhesive agent, active agent, and other components can be optimized to produce the desired peak-plateau bioavailability profile. It can further be demonstrated that increasing the active agent from 1 to 3 mg per tablet does not alter the dissolution characteristics of the tablet so a range of dosage strengths of parenteral dopamine agonists can be made. Although, upon increasing the active agent level from 1 to 3 mg per tablet in a formulation that contains a cyclodextrin or other permeabilizing agent in conjunction with bioadhesive, it is possible to accelerate the release of active agent by increasing its level relative to the cyclodextrin/bioadhesive level. Within this context, the release profile of the active agent within the tablet can be slowed by switching to a more potent bioadhesive, such as xanthan gum.

EXAMPLES

Procedures

Tablets may be tested for hardness using a Hardness Tester (Model # PAH 01, 500N, Pharma Alliance Group). The force at break point was recorded as the hardness of the tablet, or the crushing strength of the tablet. The values over 4 kg were generally considered acceptable.

Friability testing may be carried out following the USP <1216> guideline using the Key FT-400 model Friability Tester. A minimum of five tablets from are weighed and placed in the tumbler. Tablets are rotated at 25 RPM for approximately 4 minutes (100 rotations). The acceptable qualification corresponded to the USP acceptance criteria requiring weight loss of not more than 1% of the total weight.

Disintegration tests may be carried out following the USP <701> guideline at 37° C. using a VanKel Disintegration Tester, Model 10-91171B operating at 30 rpm and Lauda M6 Circulating Bath. Tablets are placed in the observation cylinder and the basket assembly is attached to the test apparatus. De-ionized water is used as the immersion fluid.

Dissolution tests may be carried out following the USP <711> guideline using a Distek 2100B Dissolution System at 37° C. For each formulation, 13 tablets are tested for dissolution in a total of 450 mL of the immersion media. For HPLC analysis, 100 µl aliquots are used for each observation time point. The concentration of drug was determined with the aid of a calibration curve by quantitation of the API's HPLC peak area. Because of the NAT's finding regarding the instability of the API in phosphate buffers (pH 6.8), which are standards for the dissolution studies mimicking saliva environments. Preferably, dissolution is tested in citric acid buffer, pH 6.0.

HPLC

Typically, all the samples were analyzed immediately after preparation/collection to reduce decomposition of the API. The reverse phase HPLC analysis was carried out using the following conditions:

Set-up: WISP 712 Automatic Injection System (Waters) with WISP Samples Cooling Unit equipped with Waters 484MS Tunable Absorbance Detector and Waters 600E Multisolvent Delivery System; Eppendorf CH-30 Column Heater/TC-50 Controller; and Shodex Solvent Degassing Unit Model KT-375.

HPLC Column: Waters Symmetry Shield RP-18, 4.6×150 mm, 3.5 µM.

Detection wavelength: 300 nm.

Analytical Method: Phase A Water, 95%/Acetonitrile 5%, 0.1% TFA; Phase B Acetonitrile, 0.1% TFA; 20-35% gradient of B over 5 min, followed by 35-40% gradient of B over 15 min. API's retention time was ca.12.3 min.

Calibration Curve: the API's solution in 0.1% citric acid.

Example 1: Acrylic-Based Formulations

The solid parenteral dosage forms 1S-3S were prepared to include:

Formulation

| Excipient | Type/Function | 1S Amt % | 1S mg | 2S Amt % | 2S mg | 3S Amt % | 3S mg |
|---|---|---|---|---|---|---|---|
| Bromocriptine | API | 1.43 | 320.0 | 1.43 | 320.0 | 1.43 | 120.0 |
| Citric Acid, Anhydrous | Solubility Enhancer | 9.99 | 2240.0 | n/a | n/a | n/a | n/a |

-continued

| Excipient | Type/Function | 1S Amt % | 1S mg | 2S Amt % | 2S mg | 3S Amt % | 3S mg |
|---|---|---|---|---|---|---|---|
| Cab-o-Sil/Cabot M-5P, | Fumed Silica/Filler | 0.40 | 89.6 | 0.40 | 89.6 | 0.40 | 33.6 |
| Carbopol ® 974/Noveon | Bioadhesive/ Release Matrix | 9.99 | 2240.0 | 9.99 | 2240.0 | 20.00 | 1680.0 |
| Mg Stearate | Glidant | 1.00 | 224.0 | 1.00 | 224.0 | 1.00 | 84.0 |
| Granular Mannitol | Filler | 77.20 | 17312.0 | 77.20 | 19552.0 | 17.17 | 6282.4 |
| Total | | 100.00 | 22425.6 | 100.00 | 22425.6 | 100.00 | 8200.0 | n/a: not added

A 50 mL tube blender was charged with bromocriptine and Cab-o-Sil. The mixture was agitated at 300 rev/min for 10 minutes. In the case of 1S, citric acid was added and blended for 15 minutes. Carbopol was added and blended for 15 minutes followed by the addition of mannitol and further blending for 30 minutes. The mixture and Mg stearate was pushed separately through a 40 mesh sieve and then mixed together for 2 minutes. The dry granulation mixture was pressed into uniform tablets (5 mm die, 70-75 mg) using the TDP press at 4,000 Psi.

Results

| Tablet Characteristics | 1S | 2S | 3S |
|---|---|---|---|
| Hardness | 5.94 kg | 6.86 kg | Good (Not exp. Tested) |
| Friability | Pass | Pass | Pass |
| Disintegration Time | 30 min | 30 min | 60 min |
| Flowability | Good | Moderate | Poor |
| Tablet Uniformity | Poor-Fair | Poor-Fair | Poor-Fair |

| | Dissolution Profile | | |
|---|---|---|---|
| T, min | 1S % Cumulative Release | 2S % Cumulative Release | 3S % Cumulative Release |
| 0 | 0.00 | 0.00 | 0.00 |
| 30 | 10.47 | 21.70 | 11.92 |
| 60 | 21.47 | 37.62 | 16.28 |
| 90 | 10.96 | 12.63 | 20.91 |
| 150 | n/t | n/t | 23.05 |
| 180 | n/t | n/t | 29.22 |
| 210 | n/t | n/t | 24.77 | n/t: not tested

Examples 2: Hydroxypropyl Methylcellulose/Polyvinyl Pyrrolidone-Based Solid Formulations Hydroxypropyl methylcellulose/Polyvinyl pyrrolidone-based solid formulations dosage forms (4S, 5S) were prepared as follows:

Formulation

| | | 4S | | 5S | |
|---|---|---|---|---|---|
| Excipient | Type/ Function | Amount % | mg | Amount % | mg |
| Bromocriptine | API | 1.43 | 220.00 | 1.43 | 220.00 |
| Cab-o-Sil/ Cabot M-5P, | Fumed Silica/Filler | 0.41 | 62.70 | n/a | n/a |
| Polyvinyl Pyrrolidone (PVP) | Bioadhesion Enhancer | 7.14 | 1100.00 | 7.14 | 1100.00 |
| Benecel MP814 | Hydroxypropylmethylcellulose/ Bioadhesive/ API Release Matrix | 35.72 | 5500.00 | 35.71 | 5500.00 |
| Mg Stearate | Glidant | 1.00 | 154.00 | 1.00 | 154.00 |
| Spray Dried Mannitol | Filler | 54.30 | 8360.00 | 54.71 | 8426.00 |
| Total | | 100.00 | 15396.70 | 100.00 | 15400.00 | n/a: not added

A 50 mL tube blender was charged with bromocriptine and optionally Cab-o-Sil (4S). The mixture was agitated at 300 rev/min for 10 minutes. IPVP was added and blended for 15 min followed by the addition of Benecel and further blending for 20 minutes. Next, mannitol was added and the mixture was blended for 30 minutes. The mixture and Mg stearate were pushed separately through a 40 mesh sieve and then mixed together for 2 minutes. The dry granulation mixture was pressed into uniform tablets (5 mm die, 70-75 mg) using the TDP press at 4,000 Psi.

Example 3: Citric Acid Buffer in the Dissolution Test

The use of citric acid buffer rather than a phosphate buffer was used to test the dissolution rate of formulation 6S. The formulation 6S released 50% of the bromocriptine within the first two hours followed by a decrease in the bromocriptine concentration. The decrease in concentration was not due to degradation of the bromocriptine.

Formulation

| Formulation 6S | | | |
|---|---|---|---|
| Excipient | Type/Function | Amount, % | mg |
| Bromocriptine | API | 1.43 | 220.00 |
| Polyvinyl Pyrrolidone (PVP) | Bioadhesion Enhancer | 5.71 | 880.00 |
| Benecel MP814 | Hydroxypropylmethyl-cellulose/ Bioadhesive/ API Release Matrix | 10.43 | 1606.00 |
| Mg Stearate | Glidant | 1.00 | 154.00 |
| Spray Dried Mannitol | Filler | 61.43 | 9460.00 |
| Cab-o-Sil/Cabot | Fumed Silica/Filler | 10.0 | 1540 |
| Total | | 100.00 | 15400.00 |

A 50 mL tube blender was charged with bromocriptine and PVP. The mixture was agitated at 300 rev/min for 10 min. Cab-o-sil was added and blended for 15 min followed by the addition of Benecel with further blending for 20 min. Next, mannitol was added and the mixture was blended for 30 min. The mixture and Mg stearate were pushed separately through a 40 mesh sieve and then mixed together for 2 min. The dry granulation mixture was pressed into uniform tablets (5 mm die, 70-75 mg) using the TDP press at 4,000 Psi.

Results

| Tablet Characteristics | 6S |
|---|---|
| Hardness | 5.02 kg |
| Friability | Pass |
| Disintegration Time | 30 min |
| Flowability | Poor |
| Tablet Uniformity | Good |

Dissolution:
Immersion Media: Citric Acid Buffer, pH 6.0 (See table below for dissolution profile)

| Dissolution Profile of 6S | |
|---|---|
| T, min | % Cumulative Release |
| 0 | 0.00 |
| 60 | 34.94 |
| 120 | 47.28 |
| 180 | 38.10 |
| 240 | 32.63 |
| 300 | 72.45 |

Examples 4: Additional HPMC/PVP-Based Formulations

Solid parenteral dosage forms (7S-10S) of the present invention were prepared. The formulation 7S displayed good stability within the course of the experiments. It released 50% of the drug after 4 hours and 70% of the drug after 6 h, with an excellent overall release profile. Also, this formulation allowed the manufacture of high quality tablets that had respectable flow properties and uniformity, and low friability. Based on 7S, further experiments explored other strategies to slightly speed up the release of the API and bring it up to the target value of >80% at 4 h. However, increasing levels of the microcrystalline cellulose reduced the release time and could be used to slow the release of buccal formulations of dopamine agonists. In the next iterative round, formulations 9S and 10S were enhanced by citric acid and contained stearic acid as glidant instead of Mg stearate (to reduce decomposition). As compared to 7S, 9S had 1.4% citric acid resulting in accelerated release of the API, 86% at 3 h and 100% at 4 h. 10S contained less HPMC than 7S and released 70% of API at 3 h and 95% at 4 h. Both 95 and 10S had good stability, made excellent tablets, and displayed reduced disintegration time, in the range of 13-15 min.

Formulations

| | 7S | | 8S | | 9S | | 10S | |
|---|---|---|---|---|---|---|---|---|
| Excipient | Amt % | mg | Amt % | mg | Amt % | mg | Amt % | mg |
| Bromocriptine | 1.43 | 220.0 | 1.43 | 220.0 | 1.43 | 220.0 | 1.43 | 220.0 |
| Polyvinyl Pyrrolidone (PVP) | 5.71 | 880.0 | 5.71 | 880.0 | 5.71 | 880.0 | 5.71 | 880.0 |
| Benecel MP814 | 14.71 | 2266.0 | 14.71 | 2266.0 | 7.36 | 1133.0 | 7.36 | 1133.0 |
| Explotab | 10.00 | 1540.0 | 10.00 | 1540.0 | 10.00 | 1540.0 | 10.00 | 1540.0 |
| ProSolv SMCC | 10.00 | 1540.0 | 33.57 | 5170.0 | 10.01 | 1540.0 | 10.01 | 1540.0 |
| Mg Stearate | 1.00 | 154.0 | 1.00 | 154.0 | n/a | n/a | n/a | n/a |
| Steric Acid | n/a | n/a | n/a | n/a | 1.00 | 154.0 | 1.00 | 154.0 |
| Spray Dried Mannitol | 61.43 | 9460.0 | 33.57 | 5170.0 | 1.43 | 220.0 | 64.47 | 9922.0 |
| Citric Acid, Anhydrose | n/a | n/a | n/a | n/a | 63.05 | 9702.0 | n/a | n/a |
| Total | 100.00 | 15400 | 100.00 | 15400 | 100.00 | 15389 | 100.00 | 15389 | n/a: not added

A 50 mL tube blender was charged with bromocriptine and polyvinyl pyrrolidone (PVP) and optionally citric acid (9S). The mixture was agitated at 300 rev/min for 10 min. Explotab was added and blended for 10 min followed by addition of the ProSolv together with Benecel and 15 min of blending. Next, mannitol was added and blended for 30 min. The mixture and separately Mg stearate was pushed through a 40 mesh sieve and then mixed together for 2 min. The dry granulation mixture was pressed into uniform tablets (5 mm die, 70-75 mg) using the TDP press at 4,000 Psi.

Results

| Tablet Characteristics | 7S | 8S | 9S | 10S |
|---|---|---|---|---|
| Hardness | 5.02 kg | n/t | 9.34 kg | 11.46 kg |
| Friability | Pass | Pass | Pass | Pass |
| Disintegration Time | 95 min | 95 min | 12-13 min | 12-13 min |
| Flowability | Good | Good | Excellent | Excellent |
| Tablet Uniformity | Good | Good | Good | Good |

Dissolution
Immersion Media: Citric Acid Buffer, pH 6.0

| | Dissolution Profile | | | |
|---|---|---|---|---|
| T, min | 7S % Cumulative Release | 8S % Cumulative Release | 9S % Cumulative Release | 10S % Cumulative Release |
| 0 | 0.00 | 0.00 | 0.00 | 0.00 |
| 30 | 19.17 | 8.68 | 22.72 | 19.49 |
| 60 | 23.12 | 15.81 | 32.12 | 27.59 |
| 90 | 28.00 | n/t | n/t | n/t |
| 120 | 30.64 | 22.13 | 61.20 | 45.62 |
| 180 | 39.51 | n/t | 86.00 | 69.73 |
| 222 | n/t | 32.97 | n/t | n/t |
| 240 | 48.27 | n/t | 101.33 | 95.31 |
| 267 | n/t | 36.76 | n/t | n/t |
| 300 | 59.40 | 39.38 | 101.46 | 100.30 |
| 360 | 71.86 | 44.76 | n/t | n/t | n/t: not tested

Examples 5: Burst-Release Formulations

In the next round of experiments a formulation 11S was prepared with elevated level of citric acid and a formulation 12S was complemented by a permeation enhancer (a cyclodextrin). The formulation 11S (elevated citric acid, 2.9% vs. 9S) was found to display "release burst" features. This effect of increasing the citric acid level to this amount is an unexpected result and one that has not been previously described for dopamine agonist formulations.

Formulations 11S and 12S were prepared to include: (1) the dopamine agonist, bromocriptine mesylate; (2) hydroxypropyl methylcellulose (HPMC); (3) polyvinyl pyrrolidone (PVP); (3) elevated levels of citric acid; and (4) optionally, a permeation enhancer (12S). The formulation 11S (2.9% citric acid than 9S) was found to display a "release burst" compared to previous formulations. The total release time was still very similar to 9S, (~4 h), however, a greater amount of 11S was released at earlier time points (as much as 36% was released within 30 min and then 46% released by 60 min). A high level of citric acid was employed for the next formulation, 12S with a permeation enhancer from the cyclodextrin family. The 12S formulation (2.5% citric acid and with 14% cyclodextrin compared to 9S) displayed an even more pronounced effect of the "release burst" behavior. Specifically, 40% of bromocriptine was released at 30 min, followed by a slower rate of release (52% at 1 h, 71% at 2 h, 91% at 3 h, and finally full release observed by the 4 h time point).

Formulations

| | | 11S | | 12S | |
|---|---|---|---|---|---|
| Excipient | Type/Function | Amount % | mg | Amount % | mg |
| Bromocriptine | API | 1.43 | 250.00 | 1.43 | 250.00 |
| Polyvinyl Pyrrolidone (PVP) | Bioadhesion Enhancer | 5.71 | 1000.00 | 5.71 | 1000.00 |
| Benecel MP814 | Hydroxypropyl Methylcellulose/ Bioadhesive/API Release Matrix | 7.36 | 1287.50 | 7.36 | 1287.50 |
| Explotab | Modified Starch/Disintegrant | 10.00 | 1750.00 | 10.00 | 1750.00 |
| ProSolv | Microcrystalline Cellulose/Filler | 10.01 | 1750.00 | 10.0 | 1750.00 |
| Citric Acid, Anhydrous | Solubility, Stability | 2.86 | 500.00 | 2.86 | 500.00 |
| Stearic Acid | Glidant | 1.00 | 175.00 | 1.00 | 1750.00 |
| Spray Dried Mannitol | Filler | 61.62 | 9922.00 | 47.32 | 8275.00 |
| Cavitron 82001 | Hydroxtpropyl Cyclodextrin/ Permeation Enhancer | n/a | n/a | 14.30 | 2500.00 |
| Total | | 100.00 | 17487.00 | 100.00 | 15400.00 | n/a: not added

A 50 mL tube blender was charged with bromocriptine, citric acid and polyvinyl pyrrolidone (PVP). The mixture was agitated at 300 rev/min for 10 min. Benecel was added and blended for 10 min. Next, Explotab was added and blended for 10 min followed by addition of the ProSolv (1750 mg) and 15 min of blending. In the case of formulation 12S, Cavitron was dispersed using the ball mill, added, and blended for 20 min. Next, mannitol was added and blended for 30 min. The mixture and separately Mg stearate was pushed through a 40 mesh sieve and then mixed together for 2 min. The dry granulation mixture was pressed into uniform tablets (5 mm die, 70-75 mg) using the TDP press at 4,000 Psi.

Results

| Tablet Characteristics | 11S | 12S |
| --- | --- | --- |
| Hardness | 8.33 kg | 10.49 kg |
| Friability | Pass | Pass |

| | Disintegration Time | |
| --- | --- | --- |
| | 10-11 min | 14-15 min |
| Flowability | Excellent | Passable but needs improvement |
| Tablet Uniformity | Good | Good |

Dissolution
Immersion Media: Citric Acid Buffer, pH 6.0

| | Dissolution Profile | |
| --- | --- | --- |
| T, min | 11S % Cumulative Release | 12S % Cumulative Release |
| 0 | 0.00 | 0.00 |
| 30 | 36.51 | 40.37 |
| 60 | 46.60 | 52.65 |
| 120 | 64.51 | 70.87 |
| 180 | 81.26 | 91.58 |
| 240 | 97.91 | 100.35 |

Example 6: Combination Tablet of Dopamine Agonist Plus a Cholesterol-Lowering Agent The cholesterol-lowering agent simvastatin was added to formulation 11S to create formulation 20S. It was found that the 11S formulation was able to incorporate an additional agent from the statin family without appreciably altering the release profile of the dopamine agonist.

The addition of the simvastatin to the mixture greatly reduced flow properties due to the fact that simvastatin is a fluffy powder able to pick up a static charge. Simvastatin also has a very poor solubility in water. In the dissolution test, the measurable concentration of simvastatin only reached roughly 6% which was more than likely due to its poor solubility in water. This can be overcome by the addition of lipophilic solubilizing agents. More importantly, simvastatin did not appreciably alter the release profile of bromocriptine.

Formulation 20S

| Formulation 20S | | | |
| --- | --- | --- | --- |
| Excipient/Manufacturer | Type/Function | Amount % | mg |
| Bromocriptine | API | 1.43 | 250.00 |
| Simvastatin | API | 7.15 | 1250.00 |
| Polyvinyl Pyrrolidone (PVP) | Bioadhesion Enhancer | 5.71 | 1000.00 |
| Benecel MP814 | Hydroxypropyl Methylcellulose/ Bioadhesive/API Release Matrix | 7.36 | 1287.50 |
| Explotab | Modified Starch/ Disintegrant | 10.00 | 1750.00 |
| ProSolv SMCC/JRC | Microcrystalline Cellulose/Filler | 10.01 | 1750.00 |
| Citric Acid, Anhydrous | Solubility, Stability | 2.86 | 500.00 |
| Stearic Acid | Glidant | 1.00 | 175.00 |
| Spray Dried Mannitol | Filler | 61.62 | 9525.00 |
| Total | | 100.00 | 17487.00 |

The formula preparation was the same as for 11S, with the additional step following the 300 rev/min of blending simvastatin into the mixture for 10 minutes.

Results

| Tablet Characteristics | 20S |
| --- | --- |
| Hardness | 9.0-10.0 kg |
| Friability | Pass |
| Disintegration Time | 14.5-16 min |
| Flowability | Poor |
| Tablet Uniformity | Not determined |

Dissolution
Immersion Media: Citric Acid Buffer, pH 6.0

| Dissolution Rate of Bromocriptine | |
| --- | --- |
| T, min | % Cumulative Release |
| 0 | 0.00 |
| 30 | 19.04 |
| 60 | 43.78 |
| 120 | 72.64 |
| 180 | 88.94 |
| 240 | 105.46 |
| 300 | 110.28 |

| Dissolution Rate of Simvastatin | |
| --- | --- |
| T, min | % Cumulative Release |
| 0 | 0.00 |
| 30 | 6.46 |
| 60 | 5.83 |
| 120 | 6.84 |
| 180 | 5.61 |
| 240 | 6.15 |
| 300 | 6.46 |

Example 7: Combination Tablet of Dopamine Agonist Plus Anti-Hypertensive Agent or Cholesterol-Lowering Agent The anti-hypertensive agent ramipril was added to the formulation of 11S to create formulation 21S. It was found that the 11S formulation was able to incorporate an additional agent from the angiotensin converting enzyme inhibitor family without appreciably altering the release profile of the dopamine agonist.

Formulation 21S

| Excipient/Manufacturer | Type/Function | Amount, % | mg |
|---|---|---|---|
| Bromocriptine | API | 1.43 | 250.00 |
| Ramipril | API | 7.15 | 1250.00 |
| Polyvinyl Pyrrolidone (PVP) | Bioadhesion Enhancer | 5.71 | 1000.00 |
| Benecel MP814 | Hydroxypropyl Methylcellulose/ Bioadhesive/API Release Matrix | 7.36 | 1287.50 |
| Explotab | Modified Starch/ Disintegrant | 10.00 | 1750.00 |
| ProSolv SMCC/JRC | Microcrystalline Cellulose/Filler | 10.01 | 1750.00 |
| Citric Acid, Anhydrous | Solubility, Stability | 2.86 | 500.00 |
| Stearic Acid | Glidant | 1.00 | 175.00 |
| Spray Dried Mannitol | Filler | 61.62 | 9525.00 |
| Total | | 100.00 | 17487.00 |

The formula preparation was the same as for 11S, with the additional step following the 300 rev/min of blending ramipril into the mixture for 10 minutes.

Results

| Tablet Characteristics | 21S |
|---|---|
| Hardness | 9.5-9.8 kg |
| Friability | Pass |
| Disintegration Time | 10.5-11.5 min |
| Flowability | Very Poor |
| Tablet Uniformity | Not determined |

Dissolution

Immersion Media: Citric Acid Buffer, pH 6.0

Dissolution Profile of Bromocriptine

| T, min | % Cumulative Release |
|---|---|
| 0 | 0.00 |
| 30 | 32.23 |
| 60 | 51.73 |
| 120 | 51.37 |
| 180 | 6.82 |
| 240 | 89.15 |
| 300 | 98.09 |

Dissolution Profile of Ramipril

| T, min | % Cumulative Release |
|---|---|
| 0 | 0.00 |
| 30 | 12.47 |
| 60 | 16.83 |
| 120 | 21.16 |
| 180 | 26.16 |
| 240 | 33.23 |
| 300 | 34.92 |

Example 8: Combination Tablet of Dopamine D2 Receptor Agonist Plus Dopamine D1 Receptor Agonist Formulation 22S was a combination of a dopamine D1 receptor agonist, bromocriptine, and a dopamine D2 receptor agonist, SKF-38393, employing the 11S base formulation with the two active agents. The release profiles for each dopamine agonist were remarkably similar and exhibited dissolution profiles very similar to the 11S formulation. A short study has been run to ensure the stability of SKF-38393. We found that no decomposition takes place in water buffered by the acidic acid within 12 h. In contrast, in alcohol solution, the API decomposes rapidly, with >5% of the API already lost within the first hour. Despite the large amount of SKF-38393, the formulation displayed good flow properties and produced quality tablets.

Formulation 22S

| Excipient/Manufacturer | Type/Function | Amount % | mg |
|---|---|---|---|
| Bromocriptine | API | 1.43 | 125.00 |
| SKF-38393 | API | 14.86 | 1250.00 |
| Polyvinyl Pyrrolidone (PVP) | Bioadhesion Enhancer | 5.71 | 500 |
| Benecel MP814 | Hydroxypropyl Methylcellulose/ Bioadhesive/API Release Matrix | 7.36 | 650 |
| Explotab | Modified Starch/ Disintegrant | 10.00 | 875.00 |
| ProSolv SMCC/JRC | Microcrystalline Cellulose/Filler | 10.01 | 875.00 |
| Citric Acid, Anhydrous | Solubility, Stability | 2.86 | 250 |
| Stearic Acid | Glidant | 1.00 | 87.5 |
| Spray Dried Mannitol | Filler | 47.29 | 4137.5 |
| Total | | 100.00 | 8750.00 |

The formula preparation was the same as for 11S, with the additional step following the 300 rev/min of blending SKF-38393 into the mixture for 10 minutes.

Results

| Tablet Characteristics | 22S |
|---|---|
| Hardness | 10.2-10.6 kg |
| Friability | Pass |
| Disintegration Time | 12.5 min |
| Flowability | Good |
| Tablet Uniformity | Not determined |

Dissolution
Immersion Media: Citric Acid Buffer, pH 6.0

Dissolution Profile of Bromocriptine-22S

| T, min | % Cumulative Release |
|---|---|
| 0 | 0.00 |
| 30 | 19.04 |
| 60 | 43.78 |
| 120 | 72.64 |
| 180 | 88.94 |
| 240 | 105.46 |
| 300 | 110.28 |

Dissolution Profile of SKF-38393-22S

| T, min | % Cumulative Release |
|---|---|
| 0 | 0.00 |
| 30 | 44.46 |
| 60 | 62.22 |
| 120 | 85.08 |
| 180 | 102.21 |
| 240 | 108.80 |
| 300 | 110.58 |

Example 9: Accelerated Burst-Release Formulations

Based on the Results of the 11S and 12S formulations, the next series of formulations (23S, 24S) were created to further accelerate both the tablet disintegration time and the dissolution time for the dopamine agonist preparation. This was effectively accomplished by replacing the Explotab® disintegrant with a Pharmaburst® disintegrant, which reduced the disintegration time from 13-15 minutes to about 5 minutes and accelerated the dissolution time for 100% dissolution from about 4 hours to about 1.0-2.0 hours. Formulations 23S and 24S displayed excellent flow properties and generated very robust hard tablets with fast disintegration time with 24S disintegrating a bit faster than 23S. These findings as consistent with our previous observations that Cavitron slows down disintegration time (e.g., 11S vs. 12S).
Formulations A 50 mL tube blender was charged with bromocriptine, citric acid and polyvinyl pyrrolidone (PVP). The mixture was agitated at 300 rev/min for 10 min. Benecel was added and blended for 10 min. In the case of formulation 24S, Caviton was added and blended for 10 min. Next, Pharmaburst was added and blended for 30 min. The mixture and separately Mg stearate was pushed through a 40 mesh sieve and then mixed together for 2 min. The dry granulation mixture was pressed into uniform tablets (5 mm die, 70-75 mg) using the TDP press at 4,000 Psi.
Results

| Tablet Characteristics | 23S | 24S |
|---|---|---|
| Hardness | 12.9 kg | 13.4 kg |
| Friability | Pass | Pass |
| Disintegration Time | 5 min | 7.5 min |
| Flowability | Excellent | Excellent |
| Tablet Uniformity | Good | Good |

Dissolution
Immersion Media: Citric Acid Buffer, pH 6.0

Dissolution Profile

| T, min | 23S % Cumulative Release | 24S % Cumulative Release |
|---|---|---|
| 0 | 0.00 | 0.00 |
| 30 | 80.84 | 34.38 |
| 60 | 102.37 | 60.28 |
| 120 | 105.67 | 106.87 |
| 180 | 105.17 | 114.67 |
| 240 | 105.92 | 116.05 |
| 300 | n/t | 116.05 | n/t: not tested

Example 10: Dual Layer Tablets for Peak-Plateau Dissolution Profiles of Dopamine Agonists Dual layer tablets 30DL were designed to produce a release profile intermediate between 23S and 24S. The tablets were produced using Carver press and displayed the expected release characteristics. This experiment confirms

| | | 23S | | 24S | |
|---|---|---|---|---|---|
| Excipient | Type/Function | Amount % | mg | Amount % | mg |
| Bromocriptine | API | 1.43 | 250.00 | 1.43 | 250.00 |
| Polyvinyl Pyrrolidone (PVP) | Bioadhesion Enhancer | 5.71 | 1000.00 | 5.71 | 1000.00 |
| Benecel MP814 | Hydroxypropyl Methylcellulose/ Bioadhesive/API Release Matrix | 7.36 | 1300.00 | 7.36 | 1300.00 |
| Citric Acid, Anhydrous | Solubility, Stability | 2.86 | 500.00 | 2.86 | 500.00 |
| Stearic Acid | Glidant | 1.00 | 175.00 | 1.00 | 175.00 |
| Pharmaburst | Disintegrant, Filler | 81.64 | 14275.00 | 81.64 | 11785.00 |
| Cavitron 82004 | Hydroxypropyl Cyclodextrin/Permeation Enhancer | n/a | n/a | 14.30 | 2500.00 |
| Total | | 100.00 | 17500.00 | 100.00 | 15400.00 | n/a: not added the possibility of using dual layer tablets for fine tuning of other formulations to achieve (and modify by accelerating the time to peak or slowing the tail plateau times) desired peak-plateau dopamine agonist release profiles.

The tablets (70 mg) were punched one by one into a 5 mm die on a bench-top 20 Ton Carver press using pre-weighted amounts of the two components, A and B (35 mg each) at 2000 Psi pressure. Before applying a press force, the formulation mixture was pre-compressed in a two-step process using manual power. Each tablet was examined for visible irregularities and the quality of the interface layer aided by adding a yellow dye to the component A.

Formulation of Components A and B

|  |  | 30DL A | | 30DL B | |
| --- | --- | --- | --- | --- | --- |
| Excipient | Type/Function | Amount % | mg | Amount % | mg |
| Bromocriptine | API | 1.43 | 250.00 | 1.43 | 250.00 |
| Polyvinyl Pyrrolidone (PVP) | Bioadhesion Enhancer | 5.71 | 1000.00 | 5.71 | 1000.00 |
| Benecel MP814 | Bioadhesive/API Release Matrix | 7.36 | 1300.00 | 7.36 | 1300.00 |
| Citric Acid, Anhydrous | Solubility, Stability | 2.86 | 500.00 | 2.86 | 500.00 |
| Stearic Acid | Glidant | 1.00 | 175.00 | 1.00 | 175.00 |
| Pharmaburst | Disintegrant, Filler | 81.16 | 14191.00 | 81.16 | 11785.00 |
| Al Lake Pigment No. 10 | Dye | 0.48 | 84 | n/a | n/a |
| Cavitron 82004 | Hydroxypropyl Cyclodextrin/Permeation Enhancer | n/a | n/a | 14.3 | 2500.00 |
| Total |  | 100.00 | 17500.00 | 100.00 | 17500.00 | n/a: not added

A 50 mL tube blender was charged with 250 mg of bromocriptine, citric acid, and polyvinyl pyrrolidone (PVP). The mixture was agitated at 300 rev/min for 10 min. Benecel and optionally Lake Pigment (A) were added and blended for 10 min. In the case of component B, Cavitron (2500 mg) was added and blended for 10 min. Next, Pharmaburst was added and blended for 30 min. The mixture and separately Mg stearate was pushed through a 40 mesh sieve and then mixed together for 2 min.

Results

| Tablet Characteristics | 30DL |
| --- | --- |
| Hardness | n/t |
| Friability | Pass |
| Disintegration Time | n/t |
| Flowability | n/t |
| Tablet Uniformity | Good | n/t: not tested

Dissolution

Immersion Media: Citric Acid Buffer, pH 6.0

| Dissolution Profile of Bromocriptine-30DL | |
| --- | --- |
| T, min | % Cumulative Release |
| 0 | 0.00 |
| 30 | 49.30 |
| 60 | 73.54 |
| 120 | 91.04 |
| 240 | 97.32 |
| 300 | 97.88 |

Example 11: Ergocriptine Incorporated into the 12S Formulation

For formulation 25S, the bromocriptine in formulation 12S was replaced by the dopamine agonist ergocriptine. The release profiles for each dopamine agonist were remarkably similar and exhibited dissolution profiles very similar to the 12S formulation.

Formulation 25S

| Formulation 25S | | | |
| --- | --- | --- | --- |
| Excipient/Manufacturer | Type/Function | Amount % | mg |
| Ergocriptine | API | 1.43 | 250.00 |
| Polyvinyl Pyrrolidone (PVP) | Bioadhesion Enhancer | 5.71 | 1000.00 |
| Benecel MP814 | Hydroxypropyl Methylcellulose/ Bioadhesive/API Release Matrix | 7.36 | 1287.50 |
| Explotab | Modified Starch/Disintegrant | 10.00 | 1750.00 |
| ProSolv SMCC/JRC | Microcrystalline Cellulose/Filler | 10.01 | 1750.00 |
| Cavitron 82004 | Hydroxypropyl Cyclodextrin/Permeation Enhancer | 14.30 | 2500.00 |

-continued

| Formulation 25S | | | |
|---|---|---|---|
| Excipient/Manufacturer | Type/Function | Amount % | mg |
| Citric Acid, Anhydrous | Solubility, Stability | 2.86 | 500.00 |
| Stearic Acid | Glidant | 1.00 | 175.00 |
| Spray Dried Mannitol | Filler | 47.32 | 8275.00 |
| Total | | 100.00 | 17487.00 |

The formulation was prepared as described above for formulation 12S, with ergocriptine rather than bromocriptine.

Results

| Tablet Characteristics | 25S |
|---|---|
| Hardness | 10.7-10.9 kg |
| Friability | Pass |
| Disintegration Time | 16-18 min |
| Flowability | Excellent |
| Tablet Uniformity | Good |

Dissolution
Immersion Media: Citric Acid Buffer, pH 6.0

| Dissolution Profile of Ergocriptine- 25S | |
|---|---|
| T, min | % Cumulative Release |
| 0 | 0.00 |
| 30 | 39.12 |
| 60 | 53.53 |
| 120 | 71.12 |
| 240 | 94.09 |

Example 12: Gel Dopamine Agonist Formulations

A series of gel formulations (26S, 31Gel and 34Gel) were constructed to provide for mucosal, transdermal, and/or subcutaneous administration of dopamine agonists with good product stability (i.e., shelf life). Since acrylic based formulations degrade dopamine agonists, particularly those of the ergot-family, a different formulation not employing any acrylic components that still provided the acceptable peak and plateau pharmacokinetic profile was constructed.

The trans-dermal, transmucosal bromocriptine formulation 26S was based on a non-aqueous glycerol-containing composition. Propylene glycol (PEG) provides high solubility of dopamine agonists such as bromocriptine and also is a proven trans-dermal permeation enhancer compliant with FDA and cGMP guidelines. According the U.S. Pat. No. 4,366,145, bromocriptine compositions containing high level of glycerol and propylene glycol have high stability. Additionally citric acid was introduced to increase the stability of API dopamine agonists. Finally, silica, an inorganic material, was used for viscosity control, as it is unlikely to affect stability in contrast to the thickening agents based on acrylic acid derivatives, and even PEG which we have shown to accelerate degradation of ergot-related dopamine agonists.

For the bioadhesive system, a mixture of hydroxypropyl cellulose (Benecel) and Crosspovidone in a 2:1 ratio was added to the tablet formulations. This bioadhesive combination is expected to generate a gel with good API stability. A short-term stability study showed that no decomposition took place within 72 h after storing the gel in the refrigerator at 4° C.

Gel formulation 31Gel was developed using formulation 26S based on the non-aqueous system that included glycerol and propylene glycol with a viscosity controlled by addition of silica. After preliminary experimentation, a HPMC/PVP bioadhesive was added to this gel combination. Aerosil silica allows for an effective control of stability producing a gel that shows good homogeneity after one week of storage. Additionally, no decomposition of bromocriptine was been detected after 3 days when stored at 5° C. As compared to the gel formulation 26S, less silica was required to achieve similar thickening effect due to the addition of the bioadhesive component.

Gel formulation 34Gel was the same as 26S, however with 3% active agent instead of 1% active agent.

These formulations were stable and do not include any acrylic based ingredients which are known to accelerate the degradation of ergot-related dopamine agonists. The viscosity and bioavailability properties of these gels may be adjusted by methods that allow for the maintenance of the bioavailability profile and yet increase the absorption level of the active agent from the formulation.

These preparations can be applied transdermally, subcutaneously, or transmucosally to affect parenteral absorption.

Formulations

| | | 26S | | 31Gel | | 34Gel | |
|---|---|---|---|---|---|---|---|
| Excipient | Type/Function | Amt % | g | Amt % | g | Amt % | g |
| Bromocriptine | API | 1 | 0.9 | 1.03 | 0.9 | 3 | 2.7 |
| Propylene Glycol | Solvent, Trans-dermal delivery USP grade, Spectrum | 20 | 18.0 | 20.7 | 18.0 | 20 | 18.0 |
| Glycerol Avatar | Solvent, Trans-dermal delivery | 68 | 61.2 | 62.2 | 54.15 | 66 | 59.4 |
| Silica 200 Degussa | Thickener | 10 | 9.0 | 6.9 | 6.0 | 10 | 9.0 |
| Citric Acid Anhydrous | Stability control | 1 | 0.9 | 1 | 0.9 | 1 | 0.9 |

-continued

|  |  | 26S | | 31Gel | | 34Gel | |
| --- | --- | --- | --- | --- | --- | --- | --- |
| Excipient | Type/Function | Amt % | g | Amt % | g | Amt % | g |
| Benecel MP814 | Bioadhesive | n/a | n/a | 5.4 | 4.7 | n/a | n/a |
| Polyvinyl Pyrrolidone (PVP) | Bioadhesive | n/a | n/a | 2.7 | 2.35 | n/a | n/a |
| Total | | 100.00 | 90.0 | 100.00 | 90.0 | 100.00 | 90.9 | n/a: not added

For formulations 26S and 34Gel, in a 100 mL screw-cap bottle, citric acid was sonicated in propylene glycol for 10 min resulting in clear colorless solution. Bromocriptine was added and sonicated for 10 min producing slightly translucent liquid. Glycerol was added and the mixture was sonicated for and additional 10 minutes. Silica was gradually added to solution, with a help of manual stirring and sonication. In the initial periods after addition very viscous heterogeneous slurry was generated that gradually clears up. In the case of 31Gel, Benecel and Povidone 29/32 were added to the glycerol and the resulting suspension homogenized using a Polytron homogenizer at 5,000 rpm for 5 min. The resulting slurry was then pushed though the size 40 stainless steel mesh sieve to ensure the absence of the conglomerated particles. The milky creamy suspension (the stock solution slowly separated after several days of subsequent storage in the refrigerator) was added to the polypropylene mixture and sonicated for 5 min. 6 g of silica was gradually added to solution (2×3 g), with a help of manual stirring and sonication. In the initial periods after addition a very viscous heterogeneous slurry was generated that gradually cleared up. As compared to the gel formulation 26S, less silica was required to achieve similar thickening effect. Because of the substantial amount of trapped air bubbles, after ageing the gel formulations for 24 h at 5° C. in the refrigerator, the final formulation was degassed in a vacuum desiccators for 6 h resulting in a clear slightly yellow gel. This final gel was packed into a round bottle equipped with an airless pump.

Example 13: Influence of Bioadhesive System Levels in the Tablet Upon Dissolution and Disintegration Profiles In this example, the amounts of HPMC/PVP bioadhesives in formulation 23S were altered. Formulation 27S contains a 20% higher load of HPMC/PVP bioadhesive system than 23S. As compared to 23S, 27S displayed a substantially slowed release, with 60% of the drug released in 1 h and 94% in 2 h. Using higher levels of bioadhesive components seems to be an inappropriate strategy for providing a quick peak of dopamine agonist followed by a slower tailed release.

Formulation 28F, on the other hand, has 50% less HPMC/PVP bioadhesives as compared to formulation 23S. The release profile, however, was very similar to 23S. Taking into account the release data for 27S, these results indicated that the ratio of bioadhesive components selected for 23S was near the inflection point of transition to a slow initial release of dopamine agonist at higher levels of bioadhesive (i.e., loss of initial rapid peak dissolution).

Formulation 27S

|  |  | 27S | | 28S | |
| --- | --- | --- | --- | --- | --- |
| Excipient | Type/Function | Amount % | mg | Amount % | mg |
| Bromocriptine | API | 1.43 | 250.00 | 1.43 | 250.00 |
| Polyvinyl Pyrrolidone (PVP) | Bioadhesion Enhancer | 6.85 | 1200.00 | 2.86 | 500.00 |
| Benecel MP814 | Hydroxypropyl Methylcellulose/ Bioadhesive/API Release Matrix | 8.83 | 1560.00 | 3.68 | 650.00 |
| Citric Acid, Anhydrous | Solubility, Stability | 2.86 | 500.00 | 2.86 | 500.00 |
| Stearic Acid | Glidant | 1.00 | 175.00 | 1.00 | 175.00 |
| Pharmaburst | Disintegrant, Filler | 79.03 | 13815.00 | 88.18 | 15425.00 |
| Total |  | 100.00 | 17500.00 | 100.00 | 17500.00 |

The formulations were prepared in the same manner as described for 23S.

Results

| Tablet Characteristics | 27S | 28S |
| --- | --- | --- |
| Hardness | 15.0-15.5 kg | 15.0-15.5 kg |
| Friability | Pass | Pass |
| Disintegration Time | 7.5-8.5 min | 6 min |
| Flowability | Good | Excellent |
| Tablet Uniformity | Good | Good |

Dissolution
Immersion Media: Citric Acid Buffer, pH 6.0

| | Dissolution Profile | | |
|---|---|---|---|
| T, min | 23S % Cumulative Release | 27S % Cumulative Release | 28S % Cumulative Release |
| 0 | 0.00 | 0.00 | 0.00 |
| 30 | 80.84 | 30.01 | 91.91 |
| 60 | 102.37 | 60.28 | 93.10 |
| 120 | 105.67 | 93.92 | 96.32 |
| 180 | 105.17 | n/t | n/t |
| 240 | 105.92 | 98.15 | 96.92 |
| 300 | n/t | 101.07 | 97.37 | n/t: not tested

Example 14: The Use of Xanthan Gum as the Bioadhesive System

Formulation 29S incorporated xanthan gum in place of HPMC, at the same ratio to other tablet components as in 23S, to investigate the influence of such gums on tablet disintegration and dopamine agonist dissolution profiles. This change resulted in a significantly slower release of the dopamine agonist. Therefore, xanthan gum can only be considered as an alternative to HPMC/PVP system at reduced levels, or in combination at reduced levels with a "super fast" disintegrating tablet (see formulation 40SuF below) to effectuate the peak-plateau dissolution curve.
Formulation

| | Formulation 29S | | |
|---|---|---|---|
| Excipient/Manufacturer | Type/Function | Amount, % | mg |
| Bromocriptine | API | 1.43 | 250.00 |
| Polyvinyl Pyrrolidone (PVP) | Bioadhesion Enhancer | 5.71 | 1000.00 |
| Xanthan Gum | Bioadhesive/API Release Matrix | 7.36 | 1300.00 |
| Citric Acid, Anhydrous | Solubility, Stability | 2.86 | 500.00 |
| Stearic Acid | Glidant | 1.00 | 175.00 |
| Pharmaburst | Disintegrant, Filler | 81.64 | 14275.00 |
| Total | | 100.00 | 17500.00 |

The formulation was prepared as described above for formulation 23S, with xanthan gum used as the bioadhesive rather than Benecel.

Results

| Tablet Characteristics | 29S |
|---|---|
| Hardness | 14.0-14.5 kg |
| Friability | Pass |
| Disintegration Time | 7.5-8.0 min |
| Flowability | Excellent |
| Tablet Uniformity | Good |

Dissolution
Immersion Media: Citric Acid Buffer, pH 6.0

| | Dissolution of Bromocriptine- 29S |
|---|---|
| T, min | % Cumulative Release |
| 0 | 0.00 |
| 30 | 7.09 |
| 60 | 15.72 |
| 120 | 20.86 |
| 240 | 34.24 |
| 300 | 41.88 |

Example 15: Increase in Active Agent to Bioadhesive Ratio

The effect of increasing the dopamine agonist to bioadhesive ratio in the tablet formulation was explored. Compositions 32F and 33S were made as analogs of the 23S and 24S formulations, respectively, but with ratios of dopamine agonist to bioadhesive system of approximately 2.5/10 versus 1/10. As expected, the 32F formulation displayed a release profile similar to 23S. Although the new composition 33S had 3 times more bromocriptine than 24S, it displayed a significanity different release profile as compared to 24S. In fact, the release profile of 33S was more similar to 23S than 24S, being that all of the drug was released in about 120 min. The increase in active agent to bioadhesive system ration with the addition of cyclodextrin likely overloaded the drug reservoir resulting in more drug being released initially. This formulation can be useful to deliver a fast load of drug followed by a slower release with the addition of a permeation enhancer such as cyclodextrin. One can adjust the rate of initial drug delivery with a cyclodextrin-containing formulation by merely increasing the ratio of drug to cyclodextrin in the formulation so that its initial release was not a factor of its interaction with the cyclodextrin. By reducing the percentage of drug interacting with the cyclodextrin, one can accelerate the initial release of drug from the tablet.
Formulations

| | | 32F | | 33S | |
|---|---|---|---|---|---|
| Excipient | Type/Function | Amount % | mg | Amount % | mg |
| Bromocriptine | API | 4.29 | 750.00 | 4.29 | 750.00 |
| Polyvinyl Pyrrolidone (PVP) | Bioadhesion Enhancer | 5.71 | 1000.00 | 5.71 | 1000.00 |
| Benecel MP814 | Hydroxypropyl Methylcellulose/Bioadhesive/API Release Matrix | 7.36 | 1300.00 | 7.36 | 1300.00 |
| Citric Acid, Anhydrous | Solubility, Stability | 2.86 | 500.00 | 2.86 | 500.00 |

|  |  | 32F |  | 33S |  |
|---|---|---|---|---|---|
| Excipient | Type/Function | Amount % | mg | Amount % | mg |
| Stearic Acid | Glidant | 1.00 | 175.00 | 1.00 | 175.00 |
| Pharmaburst | Disintegrant, Filler | 78.78 | 13775 | 64.48 | 11285.00 |
| Cavitron 82004 | Hydroxypropyl Cyclodextrin/Permeation Enhancer | n/a | n/a | 14.30 | 2500.00 |
| Total |  | 100.00 | 17500.00 | 100.00 | 17500.00 | n/a: not tested

Formulations were preformed as described above for formulations 23S and 24S.

Results

| Tablet Characteristics | 1S | 2S |
|---|---|---|
| Hardness | 14.1-14.8 kg | 8.1-9.1 kg |
| Friability | Pass | Pass |
| Disintegration Time | 8.0-8.5 min | 12.0-12.5 min |
| Flowability | Excellent | Excellent |
| Tablet Uniformity | Good | Good |

Dissolution
Immersion Media: Citric Acid Buffer, pH 6.0

| | Dissolution Profile | |
|---|---|---|
| T, min | 32F % Cumulative Release | 33S % Cumulative Release |
| 0 | 0.00 | 0.00 |
| 30 | 81.76 | 73.74 |
| 60 | 96.06 | 91.64 |
| 120 | 95.68 | 97.69 |
| 180 | 98.16 | 99.50 |
| 240 | 97.95 | 100.52 |

Example 16: Replacement of Citric Acid with Ascorbic Acid in Tablet Formulations Formulation 35F was a 23S analog at 1 mg active agent per tablet and ascorbic acid replaced for citric acid.
Formulation 36S was a 23S analog at 3 mg active agent per tablet and ascorbic acid replaced for citric acid.
Formulation 37F was a 24S analog at 1 mg active agent per tablet and ascorbic acid replaced for citric acid.
Formulation 38S was a 24S analog at 3 mg active agent per tablet and ascorbic acid replaced for citric acid.
In all cases the replacement of citric acid with ascorbic acid resulted in a slower drug release and tablet disintegration time and can be employed as a method to do so without reducing stability of the tablet.

Formulations

|  | 35F |  | 36S |  | 37F |  | 38S |  |
|---|---|---|---|---|---|---|---|---|
| Excipient | Amt % | mg | Amt % | mg | Amt % | mg | Amt % | mg |
| Bromocriptine | 4.29 | 750.0 | 1.43 | 250.0 | 4.29 | 750.0 | 1.43 | 250.0 |
| Polyvinyl Pyrrolidone (PVP) | 5.71 | 1000.0 | 5.71 | 1000.0 | 5.71 | 1000.0 | 5.71 | 1000.0 |
| Benecel MP814 | 7.36 | 1300.0 | 7.36 | 1300.0 | 7.36 | 1300.0 | 7.36 | 1300.0 |
| Ascorbic Acid | 2.86 | 500.0 | 2.86 | 500.0 | 2.86 | 500.0 | 2.86 | 500.0 |
| Stearic Acid | 1.00 | 13775.0 | 1.00 | 175.0 | 1.00 | 175.0 | 1.00 | 175.0 |
| Pharmaburst | 78.78 | 13815.0 | 81.57 | 14275 | 64.48 | 11285 | 67.27 | 11775 |
| Cavitron 82004 | n/a | n/a | n/a | n/a | 14.3 | 2500.0 | 14.3 | 2500.0 |
| Total | 100.00 | 17500 | 100.00 | 17500 | 100.00 | 17500 | 100.00 | 17500 |

Dissolution of formulations were preformed as described above for formulations 23S and 24S.

Results

| Tablet Characteristics | 35F | 36S | 37F | 38S |
|---|---|---|---|---|
| Hardness | 13.2-16.1 kg | 13.7-15.4 kg | 14.5-15.6 kg | 13.9-15.9 kg |
| Friability | Pass | Pass | Pass | Pass |
| Disintegration Time | 7.45-8.15 min | 6.5-7.5 min | 14.5-15.5 min | 14.5-15.5 min |

-continued

| Tablet Characteristics | 35F | 36S | 37F | 38S |
|---|---|---|---|---|
| Flowability | Moderate | Good | Very Poor | Poor |
| Tablet Uniformity | Good | Moderate | Good | Good |

Dissolution
Immersion Media: Citric Acid Buffer, pH 6.0

| | 35F | 36S | 37F | 38S |
|---|---|---|---|---|
| | % Cumulative | % Cumulative | % Cumulative | % Cumulative |
| T, min | Release | Release | Release | Release |
| 0 | 0.00 | 0.00 | 0.00 | 0.00 |
| 30 | 46.68 | 53.60 | 30.19 | 19.84 |
| 60 | 73.43 | 81.69 | 47.22 | 26.99 |
| 120 | 87.78 | 90.85 | 68.93 | 40.57 |
| 180 | 90.50 | 90.52 | 71.05 | 55.40 |
| 240 | 91.45 | 91.28 | 69.35 | 70.71 |

Dissolution Profile

Example 17: Very Rapid Disintegrating Tablets

A very rapid release tablet formulation (40SuF) was made utilizing an effervescent-type disintegrant. In the formulation 40SuF, the level of bioadhesive system was doubled (to roughly 25% total HPMC/PVP). This formulation resulted in rapidly disintegrating tablets (4 min) with highly desirable "burst" release and almost linear subsequent "tailing" of slower release.

Formulation 40SuF

| Excipient/Manufacturer | Type/Function | Amount % | mg |
|---|---|---|---|
| Bromocriptine | API | 1.43 | 250.00 |
| Polyvinyl Pyrrolidone (PVP) | Bioadhesion Enhancer | 11.42 | 2000.00 |
| Benecel MP814 | Bioadhesive/API Release Matrix | 14.86 | 2600.0 |
| Citric Acid, Anhydrous | Solubility, Stability, Component of the Effervescent Mixture | 20.57 | 3600.0 |
| Stearic Acid | Glidant | 1.00 | 175.00 |
| Effersoda-12 | Effervescent Component | 41.21 | 7225.0 |
| Pharmaburst | Disintegrant, Filler | 9.43 | 1650.0 |
| Total | | 100.00 | 17500.00 |

This formulation were prepared as described above for formulations 23S with the addition of Efferesoda along at the time that citric acid was added.

Results

| Tablet Characteristics | 40SuF |
|---|---|
| Hardness | 6.7-7.6 kg |
| Friability | Pass |
| Disintegration Time | 4.0 min |
| Flowability | Poor |
| Tablet Uniformity | Good |

Dissolution
Immersion Media: Citric Acid Buffer, pH 6.0

| | Dissolution Profile of Bromocriptine 40SuF |
|---|---|
| T, min | % Cumulative Release |
| 0 | 0.00 |
| 5 | 43.92 |
| 15 | 66.57 |
| 30 | 73.02 |
| 60 | 82.27 |
| 90 | 89.58 |

Example 18: In Vivo Bioavailability Studies with Solid Parenteral Dopamine Agonist Formulations Parenteral dosage forms of the present invention were administered to Syrian hamsters to demonstrate the in vivo bioavailability of the dopamine agonists. The large food storage pouch of the Syrian hamster is an ideal biological tissue to study mucosal transport of compounds and drug formulations. The Syrian hamster also has a dermal tissue that can be used to study transdermal transport of drug preparations. Dopamine agonist pharmaceutical preparations, of the present invention, were administered to anesthetized Syrian hamsters (n=2-9 per group). Blood samples were taken prior to and at 30, 60, 90, 120, 180, and optionally at 240 and 300 minutes after drug administration, and the plasma level of bromocriptine, the dopamine agonist in these formulations, was measured. Bromocriptine was extracted from plasma and the samples were analyzed against standards via HPLC method. Bioavailability data are presented as % of $C_{max}$.

Plasma Bromocriptine Extraction Method

Two hundred and 50 microliters of plasma was mixed with 125 μl 0.5 M NHCl buffer (PH 9.2), and 900 ul hexane/1-butanol (5/1). The mixture was vortexed (3 min) and centrifuged (1000×g, 3 min). The supernatant was transferred to a set of new tubes, and 250 μl 0.025 M $H_2SO_4$ was then added to the tube. The mixture was vortexed (3 min) and centrifuged (1000×g, 3 min) again. After the top organic phase was aspirated, 500 μl dichloromethane and 150 μl NDCl buffer was added and then vortexed and centrifuged. The top aqueous layer was aspirate off and the bottom layer was evaporated at 55° C. After dry, the residue was stored at −70° C. until analyzed by HPLC.

As demonstrated below, the parenteral dosage forms of the present invention produced peak-plateau bioavailability curves in the animal model system. Further, these bioavailability examples demonstrated that it is possible to manipulate, in a predictive manner, the shape of the bioavailability curve by manipulating specific components of the drug formulation.

HPLC Analysis

The above extract was dissolved in 50 µl 50% Ethanol. 10 or 15 µl was injected into the HPLC for analysis.

Conditions:

Mobile phase: 0.1 M Dibasic potassium phosphate (pH 7.5): Acetonitrile (1:1).

Flow Rate: 0.4 ml/min.

Column: $C_{18}$ 3 ul, 100×2 mm.

Detector: UV at 300 nm.

Run Time: 2× the retention time of bromocriptine.

Bioavailability Data Analysis

Bioavailability is presented as % of Cmax. The data represent the best-fit curve acquired per treatment group.

Bioavailability Results of Formulations 23S and 24S and the Combination 30DL

The bioavailability of the 23S formulation was characterized by a dopamine agonist peak plasma level within 30 minutes of drug mucosal administration with a subsequent reduction in plasma levels shortly thereafter. When cyclodextrin was added to the 23S formulation to enhance bioadhesion and permeation to create the 24S formulation, the bioavailability was characterized by a peak plasma level of dopamine agonist within 30 minutes of drug mucosal administration and a plateau level of dopamine agonist for the ensuing 2.5 to 4.5 hours of approximately >50% of the Cmax concentration thereby resulting in a peak-plateau bioavailability curve with a 2-3 fold greater Cmax than the 23S formulation.

The 30DL formulation was a tablet that is one half of the 23S and one half of the 24S formulation combined together into a single dosage form. This "hybrid" produced a bioavailability much like the 23S, likely because the cyclodextrin to dopamine agonist ratio was too low to effectuate bioadhesion and tissue permeation of the dopamine agonist.

| Experiment Number | Formulation | Dose per Animal | TIME (minutes) Data expressed as % of Cmax | | | | | |
|---|---|---|---|---|---|---|---|---|
| | | | 0 | 30 | 60 | 90 | 120 | 180 |
| 1 | 23S | 2 mg | 0 | 100 | 20 | 7 | 7 | 30 |
| 2 | 23S | 3 mg | 0 | 62 | 100 | 71 | 29 | 26 |
| 3 | 24S | 2 mg | 0 | 100 | 57 | 44 | 77 | n/t |
| 4 | 24S | 2 mg | 0 | 100 | 85 | 73 | 92 | n/t |
| 5 | 30DL | 3 mg | 0 | 100 | 11 | 10 | 5 | 4 | n/t: not tested

Bioavailability Results of Formulations 32F and 33S

The bioavailability of the 32F formulation was characterized by a peak plasma level of dopamine agonist within 30-90 minutes after mucosal administration followed by a plateau of plasma dopamine agonist level at approximately ≥50% Cmax for up to 3.5 hours. This formulation produced a bioavailability curve between that of 23S and 24S as expected from the in vitro dissolution profiles and component characteristics of these formulations due to the dopamine agonist to bioadhesive ratio (32F vs. 23S).

The 33S formulation (the 32F formulation plus cyclodextrin) resulted in a bioavailability curve characterized by a peak plasma level of dopamine agonist within 60-90 minutes of mucosal administration and a subsequent plateau plasma level of dopamine agonist of approximately ≥50% of Cmax for up to 3.5 hours post Tmax. The 33S formulation also increased the Cmax by 2-3 fold relative to the 32F formulation. Such findings were again consistent with the effects of cyclodextrin incorporation into the formulation as it both delays tablet dissolution in vitro and increases active agent penetration of tissues in vivo.

| Experiment Number | Formulation | Dose per Animal | TIME (minutes) Data expressed as % of Cmax | | | | | |
|---|---|---|---|---|---|---|---|---|
| | | | 0 | 30 | 90 | 180 | 240 | 300 |
| 6 | 32F | 3 mg | 0 | 36 | 100 | 23 | 18 | 17 |
| 7 | 32F | 6 mg | 0 | 100 | 100 | 78 | 48 | 16 |
| 8 | 32F | 6 mg | 0 | 100 | 62 | 54 | 34 | n/t |
| 9 | 32F | 6 mg | 0 | 33 | 100 | 99 | 80 | 63 |
| 10 | 33S | 6 mg | 0 | 60 | 100 | 50 | 66 | 67 |
| 11 | 33S | 6 mg | 0 | 35 | 100 | 40 | 33 | 47 |
| 12 | 33S | 6 mg | 0 | 0 | 100 | 64 | 78 | n/t |
| 13 | 33S | 6 mg | 0 | 100 | 72 | 61 | 83 | 100 |
| 14 | 33S | 6 mg | 0 | 100 | 78 | 78 | 22 | 44 | n/t: not tested

Formulations 35F and 40SuF Bioavailability Results

The bioavailability of the 35F formulation was characterized by a peak plasma level of dopamine agonist at 180 minutes after its mucosal administration and a plateau level at approximately >50% Cmax for the next 60 minutes with subsequent decline in plasma dopamine agonist level. The 35F formulation incorporates both a) an increase in the active agent to bioadhesive ratio and b) a substitution of citric acid with ascorbic acid from the 23S formulation. Each of these manipulations to the 23S formulation was known to delay the in vitro dissolution rate of the active agent as described above in this application; thus, the bioavailability curve of the 35F was consistent with its dissolution characteristics in vitro. Such manipulations within the 35F formulation can be made to counter any other additions to the 23S formulation that may overly accelerate the active agent release and absorption in vivo, and the bioavailability was approximately double that of the 23S formulation.

The 40SuF formulation was characterized by a rapid peak dopamine agonist level within 30 minutes of drug mucosal administration followed by a sharp decline (i.e., no plateau level) in the plasma level shortly thereafter. The bioavailability of the 40SuF formulation was approximately 3-5 fold greater than that of the 23S formulation. The 40SuF formulation may be used to reduce the in vivo Tmax of formulations that exhibit a delayed in the time to reach Tmax but otherwise favorable for producing a peak-plateau bioavailability curve and therapeutic effect of dopamine agonist.

| Experiment Number | Formulation | Dose per Animal | TIME (minutes) Data expressed as % of Cmax | | | | | |
|---|---|---|---|---|---|---|---|---|
| | | | 0 | 30 | 90 | 180 | 240 | 300 |
| 15 | 35F | 6 mg | 0 | 0 | 60 | 100 | 95 | 24 |
| 16 | 35F | 6 mg | 0 | 10 | 29 | 83 | 100 | 39 |
| 17 | 40SUF | 4 mg | 0 | 100 | 26 | 49 | 0 | 0 |
| 18 | 40SUF | 4 mg | 0 | 100 | 6 | 15 | 9 | n/t | n/t: not tested

Example 19: Formulation 34Gel Tested for Mucosal, Transdermal, and Subcutaneous Delivery Routes of Administration The bioavailability of the 34gel formulation was characterized by a peak in dopamine agonist level within 60-90 minutes after its parenteral administration (mucosal, transdermal or subcutaneous) followed by a plateau plasma level of approximately ≥50% of Cmax for up to 1.5 to 3 hours thereafter. This formulation exhibits a peak-plateau bioavailability profile whether it was administered mucosally, transdermally, or subcutaneously. Moreover, this formulation of bromocriptine also produced a highly desirable and surprisingly effective improvement in metabolic disorders when administered parenterally at the appropriate time of day compared to a traditional formulation of bromocriptine previously employed to treat metabolic disorders in the same animal model system (see Examples 30-31) The previous formulation was unsuitable for pharmaceutical use for several reasons, including extremely poor stability and untoward side effects at the administration site, thus, making its therapeutic use impossible.

Example 20: Blood Levels of Bromocriptine from Parenteral Formulations in an Animal Model of the Obesity, Glucose Intolerance, and Insulin Resistance The plasma level of intraperitoneal administrated bromocriptine in a ethanol to water solvent ratio of 30:70, at a dose previously demonstrated to reduce the insulin resistant state in Syrian hamsters (5 mg/kg), was compared to the plasma levels of bromocriptine in the same animal model following parenteral (mucosal, transdermal, or subcutaneous) administration of the above described formulations of the present invention. Mucosal, transdermal, or subcutaneous administration of 10-20 mg/kg of bromocriptine of the present invention, particularly 32F, 33S, 26S, 34Gel, 35F, and 40SuF formulations, to Syrian hamsters resulted in blood levels of bromocriptine similar to those of previous formulations (in the ethanol/water vehicle) administered intraperitoneally at 5 mg/kg animals. Therefore, it is possible to deliver the formulations of the present invention via parenteral routes to achieve a therapeutically effective dose of dopamine agonist required to reduce metabolic disorders in animal models of metabolic disease.

Figure 6:
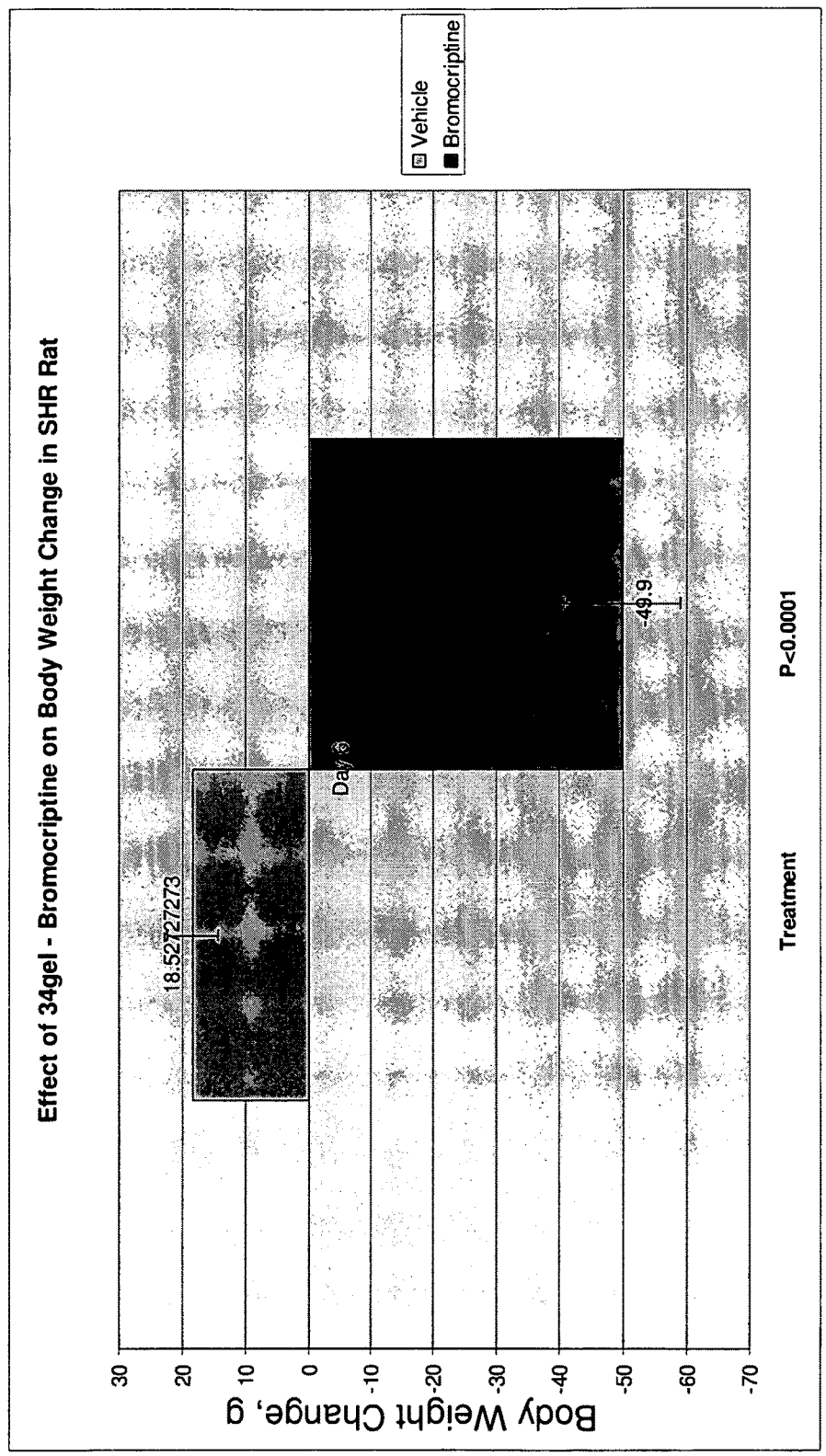
FIG. 6 is a graph showing the effect of 7 day parenteral treatment with the 34 Gel formulation (10 mg/kg) on body weight change in the SHR rat model.
Figure 7:
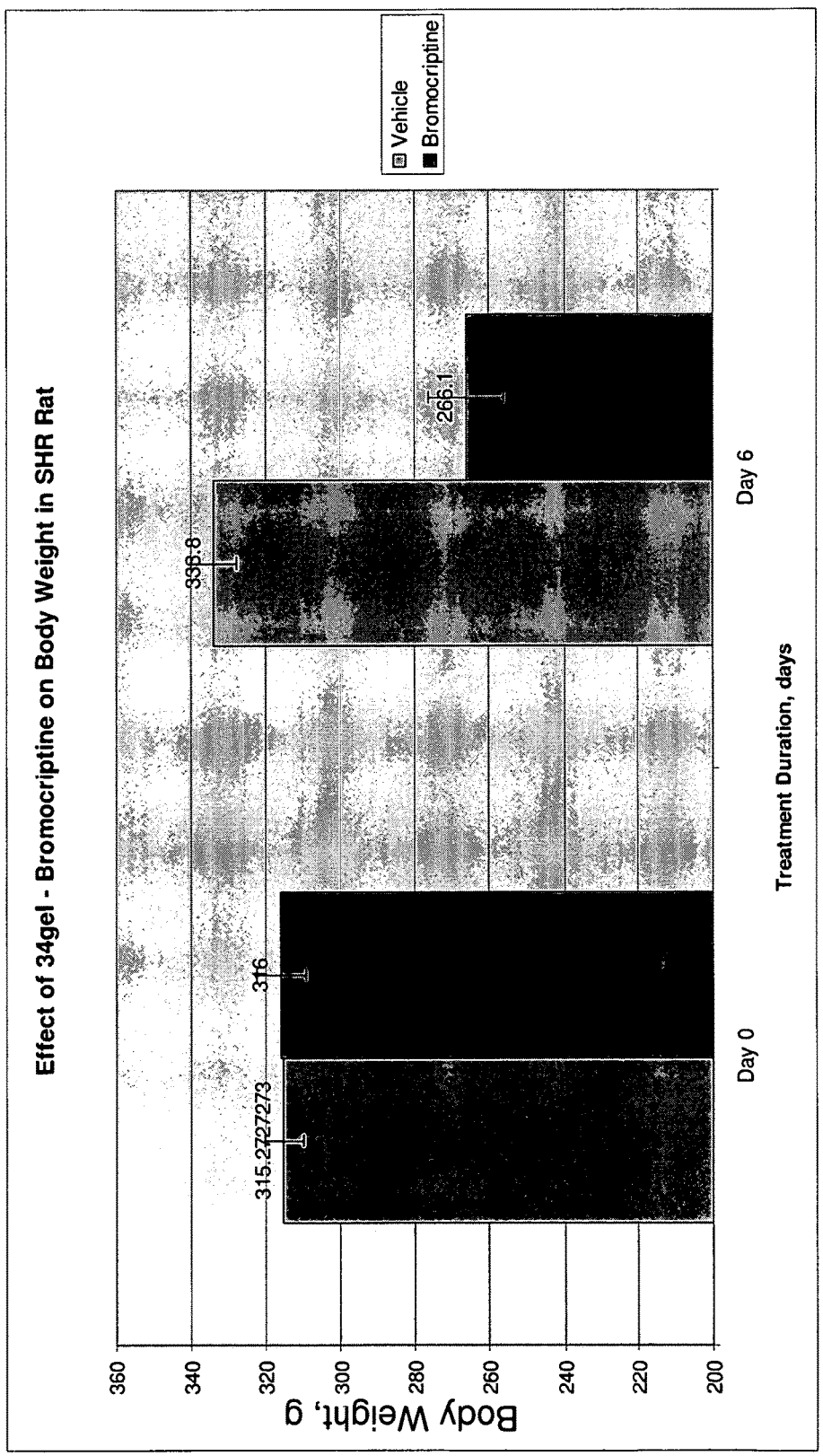
FIG. 7 is a graph showing the effect of 7 day parenteral treatment with the 34 Gel formulation (10 mg/kg) on body weight in the SHR rat model.

Example 21: In Vivo Effects of 34Gel on Body Weight Gain, Plasma Insulin Level, Insulin Sensitivity, and Blood Pressure in 16 Week-Old SHR Rats Sixteen week old male Spontaneous Hypertensive Rats (SHR) were treated daily with either formula 34Gel with an 30% ethanol vehicle via parenteral injection at 10 mg/kg body weight (n=100) or 30% ethanol vehicle (n=10) for a period of 7 days at the daily onset of locomotor activity in these animals (at initial lights off). The measurement of blood pressure, plasma glucose and insulin levels, and the calculation of insulin sensitivity from the plasma glucose and insulin levels were conducted. Relative to vehicle controls, 34Gel treatment resulted in a reduction in insulin resistance (HOMA-IR) from 12 to 2.65 (FIG. 1), a reduction in hyperinsulinemia (from 2.4 to 0.5 ng/ml) (FIG. 2), a reduction in systolic and diastolic blood pressure (each by 25 mm Hg) (FIG. 3), a change from baseline in body weight of 50 grams versus a gain of 18 grams for control animals,

| Experiment Number | Formulation, route | Dose per Animal | TIME (minutes) Data expressed as % of Cmax | | | | | | | |
|---|---|---|---|---|---|---|---|---|---|---|
| | | | 0 | 30 | 60 | 90 | 120 | 180 | 240 | 300 |
| 19 | 26Sgel Mucosal | 3 mg | 0 | 31 | 100 | 100 | 100 | n/t | n/t | n/t |
| 20 | 34gel Transdermal | 10.8 mg | 0 | 26 | 100 | 81 | 71 | 40 | 55 | 67 |
| 21 | 34gel Transdermal | 10.8 mg | 0 | 45 | 100 | 79 | 100 | n/t | n/t | n/t |
| 22 | 34gel SC | 3.3 mg | 0 | 54 | 100 | 67 | 92 | 67 | 96 | 8 |
| 23 | 34gel SC | 3.3 mg | 0 | 100 | 100 | 100 | 100 | 0 | n/t | n/t |
| 24 | 34gel SC | 3.3 mg | 0 | 0 | 0 | 100 | 28 | 50 | 50 | 45 |
| 25 | 34gel SC | 3.3 mg | 0 | 19 | 34 | 100 | 100 | 27 | 26 | n/t |
| 26 | 34gel SC | 3.3 mg | 0 | 100 | 62 | 69 | 81 | 43 | n/t | n/t | n/t: not tested (FIGS. 4 and 5), and a reduction in plasma endothelin-1 levels of 47% (FIG. 6). These results demonstrated that paretneral administration of 34Gel at the pre-determined time of day results in a bioavailability curve for bromocriptine with a plasma peak within 90 minutes followed by ≥50% of Cmax for the following for at least 60-90 minutes and produces improvements (reductions) in metabolic disorders in the well established SHR rat model of metabolic disease.

Compared to a formulation that does not produce the ideal peal-plateau curve as described in this application, at an equal dose, parenterally administered 34Gel had a greater effect on hyperinsulinemia, insulin resistance, and body weight gain when administered at the same time of day in the same animal model of metabolie disease (Diabetes 57Suppl 1, A176, 2008). Simultaneous reductions in multiple risk factors for cardiovascular disease such as hyperinsulinemia, insulin resistance, blood pressure, body weight gain, and plasma endothelin-1 level in the SHR rat can be accomplished by timed daily parenteral administration of a dopamine agonist formulation that produces a peak-plateau bioavailability curve. These results support a role for such therapy in the treatment (reduction) of cardiovascular disease.

Example 22: Stability of Parenteral Formulations of Bromocriptine

Bromocriptine formulations were placed in low density polyethylene containers equipped with a water-absorbing desiccant and maintained at 50° C. and 60% relative humidity for 5 days. These formulations were then prepared for HPLC analysis and analyzed for bromocriptine and bromocriptinine (major degradant of bromocriptine) content against standard preparations of bromocriptine and bromocriptinine.

The bromocriptinine levels in the 24S, 32F, and 33S formulations were all less than 2% following their exposure to the 50° C./60% relative humidity environment for 5 days as tested above. At 4° C., these formulations exhibit less than 1% bromocriptinine formation. Bromocriptine is extremely labile to heat and moisture and such conditions generally induce its degradation and resultantly large levels of bormocriptinine. These bromocriptine formulation stability test results at 50° C. and 60% relative humidity demonstrate that these formulations can potentially be stable for long periods of time under room temperature (25° C.) and humidity conditions.

Discussion

The influence of several excipients upon the dissolution profile of the buccal dopamine agonist formulation can be readily appreciated by comparing the dissolution curves for the various buccal/sublingual/mucosal formulations of tablets from the 7S through 24S formulations below. First, to achieve an in vivo pharmacokinetic profile with a rapid (short) Tmax (between about 1-90 minutes) followed by a sustained plateau at between 50% to 100% of the Cmax (for about 60 to 360 minutes) (desired peak-plateau PK profile), a formulation allows for a rapid dissolution (of slope A) (and absorption) followed by a slower but constant dissolution (of slope <A) (and absorption) (desired release profile). The excipients of Prosolv (microcellulose filler) and Benecel (bioadhesive, dopamine agonist release matrix) slow the (early and late) dissolution rate as their level is increased in the tablet. Contrariwise, the excipients of citric acid and Pharmaburst accelerate the early and overall dissolution rate of the dopamine agonist, respectively. Under these circumstances, we have demonstrated that adding citric acid and reducing the Benecel level to the 7S formulation as in 9S increases the overall dissolution rate of the dopamine agonist while maintaining the desired early fast dissolution followed by a slower constant dissolution. Moreover, if we increase the Prosolv level in the tablet, the overall dissolution rate is slowed substantially (8S formulation). If cyclodextrin is added to the 9S formulation as in 10S, one can further improve this desired release profile while enhancing the absorption characteristics of the formulation. If we increase further the citric acid level in the 9S tablet as in the 11S formulation, then the early burst-release of the formulation is markedly enhanced with about 40% released within the first 30 minutes followed by a slower but constant release for the next 210 minutes. This desired release profile is further improved by the addition of a cyclodextrin, as in 12S, that also enhances the absorption characteristics of the formulation. If one switches the Explotab disintegrant for Pharmaburst, the disintegration time is accelerated (from about 15 to 5 minutes). This accelerated disintegration is a desirable characteristic for buccal/sublingual/mucosal tablet administration that adds to and facilitates patient compliance with use. Also, use of Pharmaburst accelerates the overall dissolution profile of the formulation. It can be appreciated that the exact desired release profile conforming to the general characteristics of an early fast release followed by a slower sustained release of dopamine agonist can be achieved by subtle adjustments to those excipients that influence and regulate the kinetics of release (early-fast or secondary sustained slower release) as described above. The excipients of Prosolv (microcellulose filler) and Benecel (bioadhesive, dopamine agonist release matrix) slow the (early and late) dissolution rate as their level is increased in the tablet. Contrariwise, the excipients of citric acid and Pharmaburst accelerate the early and overall dissolution rate of the dopamine agonist, respectively. The 11S and 12S formulations exhibit the desired release profiles of the formulation. Furthermore, it was demonstrated that this formulation allows for very similar dissolutions of multiple dopamine agonists even in the circumstance of simultaneous combinations of dopamine agonists, such as dopamine D1 and D2 receptor agonists within a single tablet formulation. And, it is possible to add other metabolic disorder treating agents to this dopamine agonist formulation. Such additions may or may not require adjustments to the base formulation to improve or acceleratae the dopamine agonist release profile utilizing methods described below.

The 23S and 24S formulations though different from the 11S and 12S formulations, also exhibit desired release profiles. Relative to 11S and 12S formulations, the 23S and 24S formulations, respectively, exhibit the beneficial characteristic of a reduced disintegration time, that translates into increased active agent availability to the absorbing biological surface during the desired administration window of the day (e.g., mucosal outer layer or cellular membrane) and therefore increasing bioavailability during this time. The more rapid disintegration time also should improve patient compliance with the drug administration. Moreover, it can be appreciated that by altering the ratio of Explotab versus Pharmaburst as well as adjusting the Benecel and Prosolv levels in the tablet, an intermediate release profile of dopamine agonist between that of 11S/12S and 23S/24S formulations can be achieved. Such hybrid formulations allow for "fine-tuning" of the desired formulation of dopamine agonist to produce the desired PK profile.

Utilizing the 23S and 24S formulations, further investigations demonstrated that the bioadhesive level within these tablet formulations is optimized at a maximum level of bioadhesive to support bioadhesion of the active agent that still allows for a quick burst dissolution of active agent. Increasing this level (on a percent of total tablet weight basis) results in a slowing of active agent dissolution time while reducing has no effect on dissolution time. Therefore, the relative amounts of bioadhesive agent, active agent and other components of the 23S and 24S formulations are optimized to produce the desired peak-plateau bioavailability profile and mucosal bioadhesion and to facilitate tissue absorption. It can further be demonstrated that increasing the active agent level within the 23S tablet from 1 to 3 mg per tablet does not alter the dissolution characteristics of the tablet so a range of dosage strengths of parenteral dopamine agonists can be made of this 23S background formulation. However, upon increasing the active agent level from 1 to 3 mg per tablet of the 24S formulation, the dissolution profile is accelerated. In formulations (33S) that contain a cyclodextrin or other permeabilizing agent in conjunction with bioadhesive, it is possible to accelerate the release of active agent by increasing its level relative to the cyclodextrin/bioadhesive level. Once again, this new formulation (33S) exhibits several desirable characteristics including rapid disintegration of the tablet, presence of optimal amount of bioadhesive so the active agent is localized to the desired site of absorption (e.g., reduced gut presentation of active agent for oral-parenteral administration formulations), quick release of active agent followed by a linear slowed release of active agent (peak-plateau dissolution curve) and presence of a permeabilizing agent for increased tissue absorption of active agent. Within this context, the release profile of the active agent within the tablet can be slowed by switching to a different disintegrant with a more potent bioadhesive property, such as xanthan gum.

In an effort to further accelerate the release of the active agent within the formulation, a tablet was constructed with an effervescent/Pharmaburst combination forming constituent in place of the Pharmaburst as the disintegrant, but with the same other ingredients as in the 23S formulation. This particular formulation accelerated the disintegration time of the tablet and the dissolution time for the active agent from the tablet relative to the Pharmaburst comparative formulation (23S). Therefore, it can be appreciated that it is possible to adjust the disintegration and dissolution time of a tablet formulation with the desired bioavailability profile of a quick-burst peak followed by a slowed release of active agent by adjusting the disintegrant of the 11S formulation. If one switches the 11S disintegrant (Explotab) to Pharmaburst (as in 23S), the disintegration and dissolution times are accelerated and if one switches the Pharmaburst disintegrant to EfferSoda/Pharmaburst combination (as in 40SuF) the disintegration and dissolution times are accelerated yet further still. Another method of accelerating the disintegration and dissolution times is the addition of citric acid to the formulation. And yet a third method of accelerating the disintegration and dissolution times of the formulation is to increase the ratio of active agent to cyclodextrin componenet of the formulation. Contraiwise, it is possible to achieve a slower dissolution rate of active agent from the formulation by either adding more cyclodextrin component to the formulation or by switching the citric acid for ascorbic acid within the formulation or by switching the disintegrant/bioadhesive system from Benecel-PVP to xanthan gum.

Such formulation preparations achieve the desired peak-plateau release profile of dopamine agonist, are parenteral and eliminate first pass metabolism as well as initial binding to the gastrointestinal dopamine receptors thereby reducing adverse GI side-effects, can be used for timed administration of dopamine agonist inasmuch as they are not sustained long-term (e.g., 12-24 hour) release formulations, can be employed to treat metabolic disease if administered appropriately and they are stable allowing for practical pharmaceutical use. A basic finding from these investigations is that alterations made to a particular formulation's dissolution profile by the above referenced means of changing the formulation translates into the same alteration in the in vivo pharmacokinetic profile of the active agent. For example, if one accelerates or slows release of active agent in in vitro dissolution, it also accelerates or slows, respectively, the absorption of active agent in vivo, etc. In total, the above examples provide means of adjusting the dissolution profile and disintegration times of a formulation while maintaining the desired quick-burst peak dissolution followed by a slower linear-like release of active agent from the formulation. Such above-described methods may be employed to effectuate adjustments in these formulation dissolution and disintegration parameters that may need to be made to compensate for the effects of any additional ingredients, such as other permeabilizing agents used to speed up or slow down the absorption of the active agent and thereby impacting the bioavailability profile of the formulation. Moreover, it can be appreciated that the above examples teach the basic formulation elements and physical science principles, and manipulations to specific ingredients within the formulation that may be employed, to construct and prepare other formulations that produce the desired dissolution of active agent in vitro and in vivo pharmacokinetic profile of active agent. In other words, these examples describe methods to adjust the time and magnitude of the peak quick burst of active agent (dopamine agonist) and also to adjust the slower release phase of dissolution from the formulation.

Gel Dopamine Agonist Formulations

A series of gel formulations was constructed to provide for mucosal, transdermal, and/or subcutaneous administration of dopamine agonists that also provide for good product stability (i.e., shelf life). Since acrylic based formulations degrade dopamine agonists, particularly those of the ergot-family, a different formulation not employing any acrylic components that still provided the acceptable peak and plateau pharmacokinetic profile had to be constructed.

The present invention is not to be limited in scope by the specific embodiments described herein. Indeed various modifications of the invention in addition to those described herein will be apparent to those skilled in the art from the foregoing description and the accompanying Figures. Such modifications are intended to fall within the scope of the appended claims.

It is further to be understood that all values are approximate and are provided for description. All references cited and discussed in this specification are incorporated herein by reference in their entirety and to the same extent as if each reference was individually incorporated by reference.

What is claimed is:

1. A stable parenteral dosage form comprising at least one dopamine agonist selected from the group consisting of 2-bromo-a-ergocriptine (bromocriptine), terguride, dihydro-ergotoxine (hydergine), erfotoxine, 6-me-thyl 8-carbobenzyloxy-aminoethyl-10-a-ergoline, 8-acy-laminoergoline, 6-methyl-8-a-(N-acyl)amino-9-ergoline, lisuride, dihydro-alpha-ergocriptine, dihydro-alpha-ergotox-ine, 6-methyl-8-a-(N-phenyl-acety)amino-9-ergoline, ergo-cornine, 9,10-di-hydroergocornine, any D-2-halo-6-alkyl-8-substituted ergoline, and D-2-bromo-6-methyl-8-cyanomethylergoline, dopamine, apomorphine, SKF38393, dihydrexidine, SKF 75670, SKF 82957, SKF 81297, SKF 82958, SKF 82598, A77636, A68930, and SKF 82526 (fenoldopam), in particulate form and at least one pharmaceutically acceptable excipient selected from the group consisting of a bioadhesion enhancer, a permeation enhancer and a stabilizer, said particulate dopamine agonist being present in a first portion containing particles of between 0.1 and 5.0 µm and a second portion containing particles of between 10 and 200 µm, said dopamine agonist and said at least one pharmaceutically acceptable excipient being present in amounts that provide the dosage form with a pharmacokinetic profile comprising
a) a Tmax at about 1 to about 90 minutes after administration of the parenteral dosage form;
b) a plasma drug concentration of at least 50% Cmax for a duration of about 90 to about 360 minutes after Tmax when said dosage form is administered parenterally.

2. The parenteral dosage form of claim 1 exhibiting a pharmacokinetic profile wherein at least about 90% of the dopamine agonist is cleared from plasma within about 240 to about 480 minutes of said plasma drug concentration.

3. The parenteral dosage form of claim 1 wherein said Tmax is about 5 to about 90 minutes after administration of the parenteral dosage form.

4. The parental dosage form of claim 1 exhibiting a pharmacokinetic profile wherein said Tmax is about 5 to about 90 minutes after administration of the dosage form and said comprises a post-Cmax level comprising about one-half Cmax within about 30 to about 150 minutes of Tmax.

5. The parental dosage form of claim 1 exhibiting a pharmacokinetic profile wherein said Tmax is about 5 to about 90 minutes after administration of the dosage form and said comprises a post-Cmax level comprising about one-half Cmax within about 90 to about 360 minutes of Tmax.

6. The parenteral dosage form of claim 1 in the form of a nasal, sublingual, buccal, transdermal, or subcutaneous dosage form.

7. The parenteral dosage form of claim 1 comprising a total of about 0.02 to about 50.0 mg of said dopamine agonist.

8. The parenteral dosage form of claim 1 further comprising an anti-hypertensive agent, anti-inflammatory agent, anti-coagulative agent, anti-hypercholesterolemic agent, anti-hypertriglyceridemic agent, anti-hyperglycemic agent or HMGCoA reductase inhibitor.

9. The dosage form of claim 1 wherein the permeation enhancer is a member selected from the group consisting of bile salts, fatty acids, fatty acid derivatives and fatty acid esters.

10. The dosage form of claim 1 wherein the permeation enhancer comprises cyclodextrin and maltodextrin.

* * * * *